US008618266B2

(12) United States Patent
Conradt et al.

(10) Patent No.: US 8,618,266 B2
(45) Date of Patent: *Dec. 31, 2013

(54) HASYLATED POLYPEPTIDES

(75) Inventors: Harald S. Conradt, Braunschweig (DE); Eckart Grabenhorst, Braunschweig (DE); Manfred Nimtz, Wolfenbüttel (DE); Norbert Zander, Meine (DE); Ronald Frank, Meine Grassel (DE); Wolfram Eichner, Butzbach (DE)

(73) Assignee: Fresenius Kabi Deutschland GmbH, Bad Homburg v.d.H., (DE)

( * ) Notice: Subject to any disclaimer, the term of this patent is extended or adjusted under 35 U.S.C. 154(b) by 1625 days.

This patent is subject to a terminal disclaimer.

(21) Appl. No.: 11/078,582

(22) Filed: Mar. 11, 2005

(65) Prior Publication Data

US 2006/0019877 A1 Jan. 26, 2006

Related U.S. Application Data

(63) Continuation-in-part of application No. PCT/EP03/08858, filed on Aug. 8, 2003.

(60) Provisional application No. 60/409,781, filed on Sep. 11, 2002.

(30) Foreign Application Priority Data

Sep. 11, 2002 (EP) ..................... 02020425

(51) Int. Cl.
| C07K 1/107 | (2006.01) |
| C07K 14/505 | (2006.01) |
| C07K 14/53 | (2006.01) |
| C07K 14/535 | (2006.01) |
| C07K 14/54 | (2006.01) |
| C07K 14/55 | (2006.01) |
| C07K 14/56 | (2006.01) |
| C07K 14/565 | (2006.01) |
| A61K 31/715 | (2006.01) |
| A61K 47/36 | (2006.01) |
| A61K 38/16 | (2006.01) |
| C08B 31/00 | (2006.01) |

(52) U.S. Cl.
USPC ............ 530/402; 514/7.7; 514/20.9; 514/60; 530/351; 530/393; 530/395; 530/397; 530/399; 536/102; 536/106; 536/124

(58) Field of Classification Search
None
See application file for complete search history.

(56) References Cited

U.S. PATENT DOCUMENTS

| 3,191,291 A | 6/1965 | Maier |
| 3,226,395 A | 12/1965 | Schimmelschmidt et al. |
| 4,001,200 A | 1/1977 | Bonsen et al. |
| 4,001,401 A | 1/1977 | Bonsen et al. |
| 4,053,590 A | 10/1977 | Bonsen et al. |
| 4,061,736 A | 12/1977 | Morris et al. |
| 4,064,118 A | 12/1977 | Wong |
| 4,125,492 A | 11/1978 | Cuatrecasas et al. |
| 4,179,337 A | 12/1979 | Davis et al. |
| 4,261,973 A | 4/1981 | Lee et al. |
| 4,412,989 A | 11/1983 | Iwashita et al. |
| 4,454,161 A | 6/1984 | Okada et al. |
| 4,496,689 A | 1/1985 | Mitra |
| 4,667,016 A | 5/1987 | Lai et al. |
| 4,703,008 A | 10/1987 | Lin |
| 4,766,106 A | 8/1988 | Katre et al. |
| 4,847,325 A | 7/1989 | Shadle et al. |
| 4,863,964 A | 9/1989 | Hedlund et al. |
| 4,900,780 A | 2/1990 | Cerny |
| 4,904,584 A | 2/1990 | Shaw |
| 4,925,677 A | 5/1990 | Feijen |
| 4,939,239 A | 7/1990 | Matsuhashi et al. |
| 4,952,496 A | 8/1990 | Studier et al. |
| 5,068,321 A | 11/1991 | Buysch et al. |
| 5,073,628 A | 12/1991 | Matsuhashi et al. |
| 5,079,337 A | 1/1992 | Leonard et al. |
| 5,110,909 A | 5/1992 | Dellacherie et al. |
| 5,214,132 A | 5/1993 | Kuga et al. |
| 5,217,998 A | 6/1993 | Hedlund et al. |
| 5,218,092 A | 6/1993 | Sasaki et al. |
| 5,218,108 A | 6/1993 | Sommermeyer et al. |
| 5,281,698 A | 1/1994 | Nitecki |
| 5,342,770 A | 8/1994 | Yamasaki |
| 5,362,853 A | 11/1994 | Kuga et al. |
| 5,420,105 A | 5/1995 | Gustavson et al. |
| 5,470,843 A | 11/1995 | Stahl et al. |
| 5,484,903 A | 1/1996 | Szablikowski et al. |

(Continued)

FOREIGN PATENT DOCUMENTS

| AU | 5238393 | 9/1993 |
| CA | 2110543 | 6/1994 |

(Continued)

OTHER PUBLICATIONS

Dietrich et al. 1998. Anesth Analg. 86: 1123-6.*
Wasley et al, 1991. Blood. 77(12): 2624-2632.*
Heitzmann et al (1974. Proc Natl Acad Sci USA 71: 3537-3561).*
Bayer et al (1979. Methods in Enzymology. 62: 310).*
Abuchowski and Davis, "Soluble Polymer-Enzyme Adducts," *Enzymes as Drugs*, 1981, Holcenberg and Rubberts (eds.), Chapter 13, pp. 367-383, John Wiley & Sons N.Y.
Alayash and Cashon, "Hemoglobin and free radicals: implications for the development of a safe blood substitute," *Molec. Med. Today*, 1995, 1(3):122-127.
Ashwell, "Carbohydrate Antigens: Coupling of Carbohydrates to Proteins by a Mixed Anhydride Reaction," *Meth. Enzymol.*, 1972, 28:219-222.
Avigad, "A Simple Spectrophotometric Determination of Formaldehyde and Other Aldehydes: Application to Periodate-Oxidized Glycol Systems," *Anal. Biochem.*, 1983, 134:499-504.

(Continued)

*Primary Examiner* — Zachary Howard
(74) *Attorney, Agent, or Firm* — Fish & Richardson P.C.

(57) ABSTRACT

The present invention relates to hydroxyalkylstarch (HAS)-polypeptide-conjugate (HAS-polypeptide) comprising one or more HAS molecules, wherein each HAS is conjugated to the polypeptide via a carbohydrate moiety or a thioether as well as to methods for the production thereof. In a preferred embodiment, the polypeptide is erythropoietin (EPO).

52 Claims, 26 Drawing Sheets

(56) References Cited

U.S. PATENT DOCUMENTS

Figure 1:
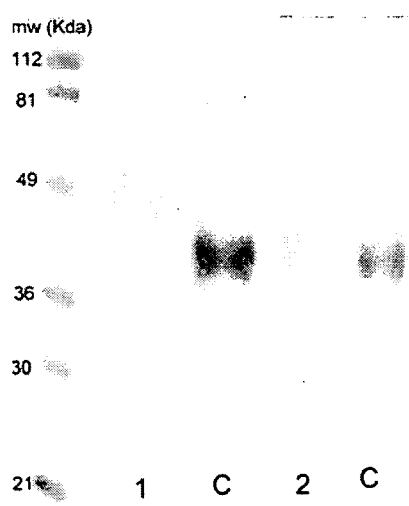

| | | | |
|---|---|---|---|
| 5,543,332 A | 8/1996 | Lihme et al. | |
| 5,581,476 A | 12/1996 | Osslund | |
| 5,622,718 A | 4/1997 | Al-Shamkhani et al. | |
| 5,723,589 A | 3/1998 | Miljkovic et al. | |
| 5,736,533 A | 4/1998 | Simon et al. | |
| 5,770,645 A | 6/1998 | Stamler et al. | |
| 5,824,778 A | 10/1998 | Ishikawa et al. | |
| 5,840,900 A | 11/1998 | Greenwald et al. | |
| 5,847,110 A | 12/1998 | Dragsten et al. | |
| 5,851,984 A | 12/1998 | Matthews et al. | |
| 5,876,980 A | 3/1999 | DeFrees et al. | |
| 5,880,270 A | 3/1999 | Berninger et al. | |
| 5,952,347 A | 9/1999 | Arison et al. | |
| 5,977,163 A | 11/1999 | Li et al. | |
| 5,981,507 A | 11/1999 | Josephson et al. | |
| 5,990,237 A | 11/1999 | Bentley et al. | |
| 6,011,008 A | 1/2000 | Domb et al. | |
| 6,083,909 A | 7/2000 | Sommermeyer et al. | |
| 6,172,208 B1 | 1/2001 | Cook | |
| 6,261,800 B1 * | 7/2001 | Nikolics et al. | 435/69.1 |
| 6,299,881 B1 | 10/2001 | Lees et al. | |
| 6,340,746 B1 | 1/2002 | Roberts et al. | |
| 6,375,846 B1 | 4/2002 | Jarrett et al. | |
| 6,395,266 B1 | 5/2002 | Martinez et al. | |
| 6,417,347 B1 | 7/2002 | Herrmann et al. | |
| 6,451,337 B1 | 9/2002 | Smith et al. | |
| 6,500,930 B2 | 12/2002 | Adamson | |
| 6,544,503 B1 | 4/2003 | Vanderhoff et al. | |
| 6,555,660 B2 | 4/2003 | Nissen et al. | |
| 6,586,398 B1 | 7/2003 | Kinstler et al. | |
| 6,596,135 B1 | 7/2003 | Mitsui | |
| 6,596,861 B1 * | 7/2003 | Moreau | 536/123.1 |
| 6,624,142 B2 | 9/2003 | Greenwald et al. | |
| 6,660,843 B1 | 12/2003 | Feige et al. | |
| 6,875,594 B2 | 4/2005 | Muir et al. | |
| 6,916,962 B2 | 7/2005 | Rosen et al. | |
| 7,115,576 B2 | 10/2006 | Sommermeyer | |
| 7,157,546 B2 | 1/2007 | Kozlowski | |
| 7,179,617 B2 | 2/2007 | DeFrees et al. | |
| 7,279,176 B1 | 10/2007 | West et al. | |
| 7,285,661 B2 * | 10/2007 | Sommermeyer et al. | |
| 7,538,092 B2 | 5/2009 | Orlando et al. | |
| 7,541,328 B2 | 6/2009 | Hemberger et al. | |
| 7,629,456 B2 | 12/2009 | Lange et al. | |
| 7,815,893 B2 | 10/2010 | Zander et al. | |
| 8,017,739 B2 | 9/2011 | Eichner et al. | |
| 2002/0065410 A1 | 5/2002 | Antrim | |
| 2003/0087877 A1 | 5/2003 | Calias et al. | |
| 2003/0191291 A1 | 10/2003 | Kochendoerfer et al. | |
| 2004/0023306 A1 | 2/2004 | Aebersold et al. | |
| 2004/0043446 A1 | 3/2004 | DeFrees et al. | |
| 2004/0180858 A1 | 9/2004 | Sommermeyer | |
| 2005/0063943 A1 * | 3/2005 | Sommermeyer et al. | 424/85.1 |
| 2005/0181985 A1 | 8/2005 | Hemberger et al. | |
| 2005/0238723 A1 | 10/2005 | Zander et al. | |
| 2006/0019877 A1 | 1/2006 | Conradt et al. | |
| 2006/0121062 A1 | 6/2006 | Eichner et al. | |
| 2006/0188472 A1 | 8/2006 | Sommermeyer et al. | |
| 2006/0194940 A1 | 8/2006 | Kozlowski | |
| 2006/0217293 A1 | 9/2006 | Orlando et al. | |
| 2007/0087961 A1 | 4/2007 | Eichner et al. | |
| 2007/0134197 A1 | 6/2007 | Eichner et al. | |
| 2008/0206182 A1 | 8/2008 | Sommermeyer et al. | |
| 2008/0207562 A1 | 8/2008 | Zander et al. | |
| 2008/0274948 A1 | 11/2008 | Eichner et al. | |
| 2009/0091549 A1 | 4/2009 | Matsumoto et al. | |
| 2009/0233847 A1 | 9/2009 | Hemberger et al. | |
| 2010/0062973 A1 | 3/2010 | Frank et al. | |
| 2010/0297078 A1 | 11/2010 | Hacket et al. | |
| 2010/0305033 A1 | 12/2010 | Hacket et al. | |
| 2010/0311670 A1 | 12/2010 | Zander et al. | |
| 2010/0317609 A1 | 12/2010 | Zander et al. | |
| 2011/0054152 A1 | 3/2011 | Zander et al. | |
| 2011/0200555 A1 | 8/2011 | Eichner et al. | |

FOREIGN PATENT DOCUMENTS

| | | |
|---|---|---|
| CA | 2 233 725 | 9/1999 |
| CA | 2 441 442 | 9/2003 |
| CA | 2 478 478 | 1/2004 |
| CA | 2 478 480 | 1/2004 |
| DE | 22 33 977 | 2/1973 |
| DE | 26 16 086 | 11/1977 |
| DE | 30 29 307 | 3/1982 |
| DE | 3501616 | 7/1986 |
| DE | 26 46 854 | 5/1989 |
| DE | 38 36 600 | 5/1990 |
| DE | 279 486 | 6/1990 |
| DE | 41 30 807 | 3/1993 |
| DE | 26 07 706 | 5/1993 |
| DE | 69025920 | 8/1996 |
| DE | 196 28 705 | 1/1998 |
| DE | 198 08 079 | 8/1999 |
| DE | 101 12 825 | 2/2002 |
| DE | 100 41 541 | 3/2002 |
| DE | 101 26 158 | 12/2002 |
| DE | 101 35 694 | 2/2003 |
| DE | 101 29 369 | 3/2003 |
| DE | 101 55 098 | 5/2003 |
| DE | 102 09 821 | 9/2003 |
| DE | 102 17 994 | 11/2003 |
| DE | 102 54 745 | 6/2004 |
| DE | 102 56 558 | 9/2004 |
| EP | 0 019 403 | 11/1980 |
| EP | 0 138 572 | 4/1985 |
| EP | 0 218 825 | 4/1987 |
| EP | 0 243 929 | 11/1987 |
| EP | 0 304 183 | 2/1989 |
| EP | 0 307 827 | 3/1989 |
| EP | 0 315 349 | 5/1989 |
| EP | 0 338 916 | 10/1989 |
| EP | 0 402 724 | 6/1990 |
| EP | 0 148 605 | 7/1990 |
| EP | 0 205 564 | 5/1991 |
| EP | 0 428 267 | 5/1991 |
| EP | 0 411 678 | 1/1992 |
| EP | 0 127 839 | 7/1992 |
| EP | 0 331 471 | 12/1992 |
| EP | 0 549 721 | 4/1994 |
| EP | 0 605 963 | 7/1994 |
| EP | 0 609 968 | 8/1994 |
| EP | 0 342 557 | 11/1994 |
| EP | 0661294 | 12/1994 |
| EP | 0 640 619 | 3/1995 |
| EP | 0 646 130 | 4/1995 |
| EP | 0 418 523 | 6/1995 |
| EP | 0 668 351 | 8/1995 |
| EP | 0 809 996 | 5/1996 |
| EP | 0806140 | 11/1997 |
| EP | 1064951 A2 * | 1/2001 |
| EP | 1 230 935 | 8/2002 |
| EP | 1 400 533 | 9/2002 |
| EP | 1 398 322 | 9/2003 |
| EP | 1 398 327 | 9/2003 |
| EP | 1 398 328 | 9/2003 |
| EP | 1 424 086 | 6/2004 |
| EP | 1496076 | 1/2005 |
| EP | 1591467 | 11/2005 |
| EP | 2070950 | 6/2009 |
| EP | 2 143 736 | 1/2010 |
| EP | 2 154 160 | 2/2010 |
| EP | 1660134 | 12/2010 |
| EP | 1372735 | 10/2011 |
| FR | 2 378 094 | 8/1978 |
| GB | 1 419 080 | 12/1975 |
| GB | 1 549 246 | 10/1976 |
| IL | 166506 | 2/2010 |
| JP | 10-287554 | 10/1998 |
| JP | 2002-003398 | 1/2001 |
| JP | 2001-294601 | 10/2001 |
| WO | WO 80/02374 | 11/1980 |
| WO | WO 90/07939 | 7/1990 |
| WO | WO90/12874 | 11/1990 |
| WO | WO 90/15628 | 12/1990 |

(56) References Cited

FOREIGN PATENT DOCUMENTS

| | | |
|---|---|---|
| WO | WO 92/11037 | 7/1992 |
| WO | WO 93/23062 | 11/1993 |
| WO | 93/24476 | 12/1993 |
| WO | WO 94/01483 | 1/1994 |
| WO | WO 94/05332 | 3/1994 |
| WO | WO 9405332 A2 * | 3/1994 |
| WO | WO 94/07536 | 4/1994 |
| WO | WO 94/13697 | 6/1994 |
| WO | WO 94/28024 | 12/1994 |
| WO | WO 94/29370 | 12/1994 |
| WO | WO 95/06058 | 3/1995 |
| WO | WO 95/13090 | 5/1995 |
| WO | WO 96/11953 | 4/1996 |
| WO | WO 96/19242 | 6/1996 |
| WO | WO 96/40662 | 12/1996 |
| WO | WO 96/41813 | 12/1996 |
| WO | WO 97/21452 | 6/1997 |
| WO | WO 97/30148 | 8/1997 |
| WO | WO 97/33552 | 9/1997 |
| WO | WO 97/38727 | 10/1997 |
| WO | WO 97/42225 | 11/1997 |
| WO | WO 98/01158 | 1/1998 |
| WO | 98/07713 | 2/1998 |
| WO | WO 98/08856 | 3/1998 |
| WO | 98/14212 | 4/1998 |
| WO | 98/14215 | 4/1998 |
| WO | WO 98/20905 | 5/1998 |
| WO | WO 98/32466 | 7/1998 |
| WO | 98/05689 | 12/1998 |
| WO | WO 98/56424 | 12/1998 |
| WO | WO 99/07719 | 2/1999 |
| WO | 99/17783 | 4/1999 |
| WO | WO 99/49897 | 10/1999 |
| WO | WO00/07738 | 2/2000 |
| WO | 00/18893 | 4/2000 |
| WO | WO 00055210 | 9/2000 |
| WO | 00/66633 | 11/2000 |
| WO | WO 00/78355 | 12/2000 |
| WO | WO 01/70272 | 9/2001 |
| WO | 01/78682 | 10/2001 |
| WO | WO 01/83522 | 11/2001 |
| WO | WO01/85799 | 11/2001 |
| WO | WO 01/93862 | 12/2001 |
| WO | WO 02/09766 | 2/2002 |
| WO | WO 02/20033 | 3/2002 |
| WO | WO 02/28841 | 4/2002 |
| WO | WO 02/40057 | 5/2002 |
| WO | WO 02/080979 | 10/2002 |
| WO | WO 03/000738 | 1/2003 |
| WO | WO 03/031464 | 4/2003 |
| WO | WO 03/031581 | 4/2003 |
| WO | 03/049699 | 6/2003 |
| WO | WO 03/059246 | 7/2003 |
| WO | WO 03/070772 | 8/2003 |
| WO | WO 03/074087 | 9/2003 |
| WO | WO 03/074088 | 9/2003 |
| WO | WO 2004/009082 | 1/2004 |
| WO | 2004/022630 | 3/2004 |
| WO | WO 2004/024761 | 3/2004 |
| WO | WO 2004/024776 | 3/2004 |
| WO | WO 2004/024777 | 3/2004 |
| WO | WO 2004/030701 | 4/2004 |
| WO | WO 2004/033651 | 4/2004 |
| WO | WO 2004/050710 | 6/2004 |
| WO | WO 2004/065425 | 8/2004 |
| WO | WO 2005/014024 | 2/2005 |
| WO | WO 2005/014035 | 2/2005 |
| WO | WO 2005/014050 | 2/2005 |
| WO | WO 2005/014655 | 2/2005 |
| WO | 2005/072778 | 8/2005 |
| WO | WO 2005/074993 | 8/2005 |
| WO | 2005/083103 | 9/2005 |
| WO | 2005/092369 | 10/2005 |
| WO | WO 2005/092390 | 10/2005 |
| WO | 2005/112954 | 12/2005 |
| WO | WO 2006/108052 | 10/2006 |
| WO | 2007/053292 | 5/2007 |
| WO | 2010/042638 | 4/2010 |

OTHER PUBLICATIONS

Baldwin et al., "Synthesis of Polymer-Bound Hemoglobin Samples," *Tetrahedron*, 1981, 37:1723-1726.

Balland et al., "Intracellular distribution of ampicillin in murine macrophages infected with *Salmonella typhimurium* and treated with ($^3$H)ampicillin-loaded nanoparticles," *J. Antimicrob. Chemother.*, 1996, 37:105-115.

Barbone et al., "Reticulocyte measurements as a bioassay for erythropoietin," *J. Pharm. Biomed. Anal.*, 1994, 12(4):515-522.

Bårström et al., "New derivatives of reducing oligosaccharides and their use in enzymatic reactions: efficient synthesis of sialyl Lewis a and sialyl dimeric Lewis x glycoconjugates," *Carbohydr. Res.*, 2000, 328:525-531.

Bauer et al., "Synthesis of ω-(Aminooxy)alkanethiols," *J. Org. Chem.*, 1965, 30:949-951.

Bauer and Suresh, "S-[ω-(Aminoöxy)alkyl]isothiuronium Salts, ω,ω'-Bis(aminoöxy)alkanes and Related Compounds," *J. Org. Chem.*, 1963, 28:1604-1608.

Bendele et al., "Short Communication: Renal Tubular Vacuolation in Animals Treated with Polyethylene-Glycol-Conjugated Proteins," *Toxicol. Sci.*, 1998, 42:152-157.

Benesch, "Bis(pyridoxal) Polyphosphates as Specific Intramolecular Cross-Linking Agents for Hemoglobin," *Meth. Enzymol.*, 1994, 231:267-274.

Bepperling et al., "HES 130/0.4, a new HES specification: tissue storage after multiple infusions in rats," *Crit. Care*, 1999, 3(suppl 1):P153.

Berger et al., "Galactosyltransferase-dependent sialylation of complex and endo-N-acetylglucosaminidase H-treated core N-glycans in vitro," *FEBS Lett.*, 1986, 203(1):64-68.

Black et al., "N-Bromoacetyl-glycopyranosylamines as affinity labels for a β-glucosidase and a cellulase," *Carbohydr. Res.*, 1993, 250:195-202.

Blum et al., "Improved silver staining of plant proteins, RNA and DNA in polyacrylamide gels," *Electrophoresis*, 1987, 8:93-99.

Bobbitt, "Periodate Oxidation of Carbohydrates," *Carbohydr. Chem.*, 1956, 11:1-41.

Boissel et al., "Erythropoietin Structure-Function Relationships. Mutant proteins that test a model of tertiary structure," *J. Biol. Chem.*, 1993, 268(21):15983-15993.

Boturyn et al., "Synthesis of Fluorescent Probes for the Detection of Abasic Sites in DNA," *Tetrahedron*, 1997, 53(15):5485-5492.

Bowen et al., "Estimation of Effective and Total Erythropoiesis in Myelodysplasia Using Serum Transferrin Receptor and Erythropoietin Concentrations, with Automated Reticulocyte Parameters," *Leukemia*, 1994, 8(1):151-155.

Bronzino, *The Biomedical Engineering Handbook*, CRC Press, USA, Salem, 1995, (TOC only).

Bunn & Jandl, "The Renal Handling of Hemoglobin. II. Catabolism," *J. Exp. Med.*, 1967, 129:925-934.

Burgess et al., "Stimulation by Human Placental Conditioned Medium of Hemopoietic Colony Formation by Human Marrow Cells," *Blood*, 1977, 49(4):573-583.

Bystrický et al., "Determination of the cross-linking effect of adipic acid dihydrazide on glycoconjugate preparation," *Glycoconj. J.*, 1999, 16:691-695.

Cabacungan et al., "Amine Boranes as Alternative Reducing Agents for Reductive Alkylation of Proteins," *Anal. Biochem.*, 1982, 124:272-278.

Carlsson et al., "Protein Thiolation and Reversible Protein-Protein Conjugation," *Biochem J.*, 1978, 173:723-737.

Cerami, "Beyond Erythropoiesis: Novel Applications for Recombinant Human Erythropoietin," *Semin. Hematol.*, 2001, 38:(3 Suppl 7):33-39.

Cerny et al., "A Hydroxyethyl Starch-Hemoglobin Polymer as a Blood Substitute," *Clinical Hemorheology*, 1982, 2(4):355-365.

Chamow et al., "Conjugation of Soluble CD4 without Loss of Biological Activity via a Novel Carbohydrate-directed Cross-linking Reagent," *J. Biol. Chem.*, 1992, 267(22):15916-15922.

(56) References Cited

OTHER PUBLICATIONS

Chang, "Blood Substitutes Based on Modified Hemoglobin Prepared by Encapsulation or Crosslinking: An Overview," *Biomat., Art. Cells & Immob. Biotech.*, 1992, 20:159-179.

Chagnon et al., "Murine renal cell carcinoma: evaluation of a dendritic-cell tumour vaccine," *BJU Int.*, 2001, 88:418-424.

Chaplin, "Monosaccharides," *Carbohydrate analysis: a practical approach*, 1996, Chaplin and Kennedy (eds.), Chapter 1, "Oligosaccharides," pp. 37-54.

Chaplin, "A Rapid and Sensitive Method for the Analysis of Carbohydrate Components in Glycoproteins Using Gas-Liquid Chromatography," *Anal. Biochem.*, 1982, 123:336-341.

Chapman et al., "Therapeutic antibody fragments with prolonged in vivo half-lives," *Nature Biotech.*, 1999, 17:780-783.

Chow et al., "In vitro Induction of apoptosis of neoplastic cells in low-grade non-Hodgkin's lymphomas using combinations of established cytotoxic drugs with bendamustine," *Haematologica*, 2001, 86:485-493.

Chu et al., "Further Studies on the Immunogenicity of *Haemophilus influenzae* Type b and Pneumococcal Type 6A Polysaccharide-Protein Conjugates," *Infect. Immun.*, 1983, 40:245-256.

Cumber et al., "Preparation of Antibody-Toxin Conjugates," *Meth. Enzymol.*, 1985, 112:207-225.

Davis and Flitsch, "A Novel Method for the Specific Glycosylation of Proteins," *Tetrahed. Lett.*, 1991, 32(46):6793-6796.

Delgado et al., "The Uses and Properties of PEG-Linked Proteins," *Crit. Rev. Ther. Drug Carrier Syst.*, 1992, 9(3,4):249-304.

Delorme et al., "Role of Glycosylation on the Secretion and Biological Activity of Erythropoietin," *Biochemistry*, 1992, 31(41):9871-9876.

Dittmar et al., "Human Glycoproteins and Derived Variants from Recombinant Mammalian Cell Lines," *Advances in Protein Design*, 1989, 12:145-156.

Dorner et al., "Increased Synthesis of Proteins Induces Expression of Glucose-regulated Proteins in Butyrate-treated Chinese Hamster Ovary Cells," *J. Biol. Chem.*, 1989, 264(34):20602-20607.

Dowling and Russell, "Pharmacokinetics of a long-acting oxytetracycline-polyethylene glycol formulation in horses," *J. Vet. Pharmacol. Therap.*, 2000, 23:107-110.

Dreborg and Åkerblom, "Immunotherapy with Monomethoxypolyethylene Glycol Modified Allergens," *Crit. Rev. Ther. Drug Carrier Syst.*, 1990, 6(4):315-365.

Blum et al., "Improved silver staining of plant proteins, RNA and DNA in polyacrylamide gels," *Electrophoresis*, 1987 8:93-99.

Elliott et al., "Mapping of the Active Site of Recombinant Human Erythropoietin," *Blood*, 1997, 89(2): 493-502.

European Pharmacopoeia, "Erythropoietin Concentrated Solution," 3rd Edition, 2000, Monography, pp. 655-660.

European Pharmacopoeia, "Erythropoietin Concentrated Solution," 4th Edition, 2002, Monography, pp. 1123-1128.

Fernández-Santana et al., "Conjugation of 5-azido-3-oxapentyl glycosides with thiolated proteins through the use of thiophilic derivatives," *Glycoconj. J.*, 1998, 15:549-553.

Fibi et al., "Evidence for the Location of the Receptor-Binding Site of Human Erythropoietin at the Carboxyl-Terminal Domain," *Blood*, 1991, 77(6):1203-1210.

Fibi et al., "N- and O-Glycosylation Muteins of Recombinant Human Erythropoietin Secreted From BHK-21 Cells," *Blood*, 1995, 85(5):1229-1236.

Fissekis et al., "*N*-Pantyol-(substituted)amines, Pantothenic Acid Analogues," *J. Med. Pharm. Chem.*, 1960, 2:47-56.

Forno et al., "N- and O-linked carbohydrates and glycosylation site occupancy in recombinant human granulocyte-macrophage colony-stimulating factor secreted by a Chinese hamster ovary cell line," *Eur. J. Biochem.*, 2004, 271:907-919.

Gaertner and Offord, "Site-Specific Attachment of Functionalized Poly(ethylene glycol) to the Amino Terminus of Proteins," *Bioconjugate Chemistry*, 1996, 7(1):38-44.

Gervais et al., "NMR investigations of the role of the sugar moiety in glycosylated recombinant human granulocyte-colony-stimulating factor," *Eur. J. Biochem.*, 1997, 247:386-395.

Gillis et al., "T Cell Growth Factor: Parameters of Production and a Quantitative Microassay for Activity," *J. Immunol.*, 1978, 120(6):2027-2032.

Gonzalez Lio and Thiem, "Chemoenzymatic synthesis of spacer-linked oligosaccharides for the preparation of neoglycoproteins," *Carbohydr. Res.*, 1999, 317:180-190.

Gould et al., "The Development of Hemoglobin Solutions as Red Cell Substitutes: Hemoglobin Solutions," *Transfus. Sci*, 1995, 16:5-17.

Grabenhorst et al., "Construction of stable BHK-21 cells coexpressing human secretory glycoproteins and human Gal($\beta$1-4)GlcNAc-R $\alpha$2,6-sialyltransferase: $\alpha$2,6-Linked NeuAc is preferentially attached to the Gal($\beta$1-4)GlcNAc($\beta$1-2)Man($\alpha$1-3)-branch of diantennary oligosaccharides from secreted recombinant $\beta$-trace protein," *Eur. J. Biochem.*, 1995, 232:718-725.

Grabenhorst and Conradt, "The Cytoplasmic, Transmembrane, and Stem Regions of Glycosyltransferases Specify Their in vivo Functional Sublocalization and Stability in the Golgi," *J. Biol. Chem.*, 1999, 274(51):36107-36116.

Grabenhorst et al., "Biosynthesis and secretion of human interleukin 2 glycoprotein variants from baculovirus-infected Sf21 cells. Characterization of polypeptides and posttranslational modifications," *Eur. J. Biochem.*, 1993, 215:189-197.

Grabenhorst et al., "In Vivo Specificity Human $\alpha$1,3/4-Fucosyltransferases III-VII in the Biosynthesis of Lewis$^x$ and Sialyl Lewis$^x$ Motifs on Complex-type *N*-Glycans. Coexpression studies from BHK-21 cells together with human $\beta$-trace protein," *J. Biol. Chem.*, 1998, 273(47):30985-30994.

Grabenhorst et al., "Genetic engineering of recombinant glycoproteins and the glycosylation pathway in mammalian host cells," *Glycoconj J.*, 1999, 16(2):81-97.

Figure 2:
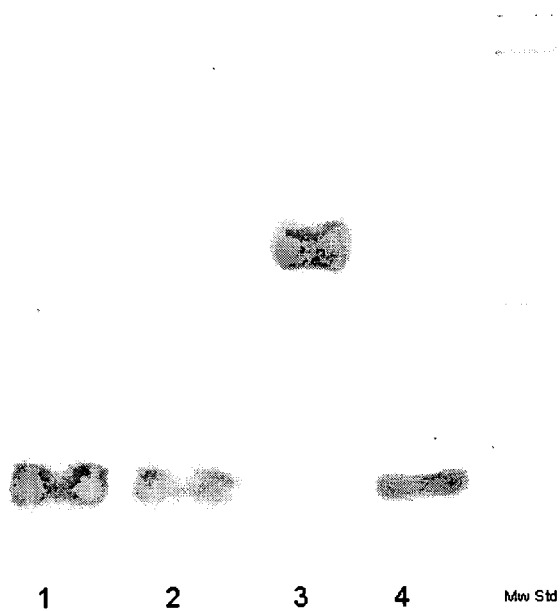

Gray, "The Direct Coupling of Oligosaccharides to Proteins and Derivatized Gels," *Arch. Biochem. Biophys.*, 1974, 163:426-628 (Fig. 2.1a).

Greenfield et al., "Evaluation in Vitro of Adriamycin Immunoconjugates Synthesized Using an Acid-sensitive Hydrazone Linker," *Cancer Research*, 1990, 50:6600-6607.

Grimmecke and Brade, "Studies on the reductive amination of 3-deoxy-D-*manno*-octulosonic acid (Kdo)," *Glycoconj. J.*, 1998, 15:555-562.

Habeeb, "Determination of Free Amino Groups in Proteins by Trinitrobenzenesulfonic Acid," *Anal. Biochem.*, 1996, 14:328-336.

Hai et al., "Diaspirin Crosslinked Hemoglobin (DCLHb™) Polymerization," *Art. Cells, Blood Subs., and Immob. Biotech.*, 1994, 22(3):923-931.

Hallaway et al., "Modulation of Deferoxamine Toxicity and Clearance by Covalent Attachment to Biocompatible Polymers," *Proc. Natl. Acad. Sci. USA*, 1989, 86:10108-10112.

Hamma and Miller et al., "4-(2-Aminooxyethoxy)-2-(ethylureido)quinoline-Oligonucleotide Conjugates: Synthesis, Binding Interactions, and Derivatization with Peptides," *Bioconj. Chem.*, 2003, 14:320-330.

Hartman and Wold, "Cross-Linking of Bovine Pancreative Ribonuclease A with Dimethyl Adipimidate," *Biochemistry*, 1967, 6(8):2439-2448.

Hashimoto et al., "Chemical Modification of the Reducing Chain End in Dextrans and Trimethylsilylation of Its Hydroxyl Groups," *J. Polymer Science: Part A: Polymer Chemistry*, 1991, 29:1271-1279.

Hattori et al., "Reduced Immunogenicity of $\beta$-Lactoglobulin by Conjugation with Carboxymethyl Dextran," *Bioconjug. Chem.*, 2000, 11:84-93.

Herman et al., "Characterization, Formulation, and Stability of Neupogene® (Filgrastim), a Recombinant Human Granulocyte-Colony Stimulating Factor," *Formulation, Characterization, and Stability of Protein Drugs*, Pearlman and Wang (eds.), Plenum Press, Chapter 7, 1996, pp. 303-328.

Hermanson, *Bioconjugate Techniques*, 1996 (TOC only).

Hermentin et al., "A Strategy for the Mapping of *N*-Glycans by High-pH Anion-Exchange Chromatography with Pulsed Amperometric Detection," *Anal. Biochem.*, 1992, 203(2):281-289.

(56) References Cited

OTHER PUBLICATIONS

Higuchi et al., "Role of Sugar Chains in the Expression of the Biological Activity of Human Erythropoietin," *J. Biol. Chem.*, 1992, 267(11):7703-7709.

Sharaf et al., "Studies on Aroyl- and Aryl-Hydrazide Derivatives from D-*glycero*-D-*gulo*-Heptono-1,4-Lactone," *Carbohydrate Res.*, 1981, 91:39-48.

Inoue et al., "An Improved Method for the Purification of Human Erythropoietin with High in Vivo Activity from the Urine of Anemic Patients," *Biol. Pharm. Bull.*, 1994, 17(2):180-184.

Iwamoto et al., "Polysaccharide-Coated Oil Droplets in Oil-in-Water Emulsions as Targetable Carriers for Lipophilic Drugs," *J. Pharm. Sci.*, 1991, 80(3):219-224.

Jia et al., "S-nitrosohaemoglobin: a dynamic activity of blood involved in vascular control," *Nature*, 1996, 380:221-226.

Jones et al., "A convenient synthesis of N-(tert-butyloxycarbonyl)aminooxy ethers," *Tetrahedron Letters*, 2000, 41(10):1531-1533.

Jones et al., "Multivalent Poly(ethylene glycol)-Containing Conjugates for In Vivo Antibody Suppression," *Bioconj. Chem.*, 2003, 14(6):1067-1076.

Kallin, "Coupling of Oligosaccharides to Proteins Using *p*-Trifluoroacetamidoaniline," *Meth. Enzymol.*, 1994, 242:119-123.

Keaney, Jr. et al., "NO Forms an Adduct with Serum Albumin that Has Endothelium-derived Relaxing Factor-like Properties," *J. Clin. Invest.*, 1993, 91:1582-1589.

Keipert et al., "Functional properties of a new crosslinked hemoglobin designed for use as a red cell substitute," *Transfusion*, 1989, 29:768-773.

Kitamura et al., "Establishment and Characterization of a Unique Human Cell Line That Proliferates Dependently on GM-CSF, IL-3, or Erythropoietin," *J. Cell. Phys.*, 1989, 140:323-334.

Kitamura et al., "Chemical Engineering of the Monoclonal Antibody A7 by Polyethylene Glycol for Targeting Cancer Chemotherapy," *Cancer Res.*, 1991, 51:4310-4315.

Kleine-Tebbe et al., "Allergen Immunotherapy—A Position Paper of the German Society for Allergology and Clinical Immunology," *Pneumologie*, 2001, 55:438-444 (w/English summary).

Klemm et al., "Esterification of Cellulose," *Comprehensive Cellulose Chemistry*, 1998, vol. 2 Wiley-VCH, Weinheim, New York, especially chapter 4.4, pp. 99-207.

Kobayashi et al., "Reduced Immunogenicity of β-Lactoglobulin by Conjugation with Carboxymethyl Dextra Differing in Molecular Weight," *J. Agric. Food Chem.*, 2001, 49(2):823-831.

Kojima et al., "Mitomycin C-dextran conjugate: a novel high molecular weight pro-drug of mitomycin C," *J. Pharm. Pharmacol.*, 1980, 32:30-34.

Komatsu et al., "Cloning of granulocyte colony-stimulating factor cDNA from human macrophages and its expression in *Escherichia coli*,"*Jpn. J. Cancer Res.*, 1987, 78(11):1179-1181.

Krantz, "Erythropoietin," *Blood*, 1991, 77(3):419-434.

Krystal, "Physical and Biological Characterization of Erythroblast Enhancing Factor (EEF), a Late Acting Erythropoietic Stimulator in Serum Distinct from Erythropoietin,"*Exp. Hematol.*, 1983, 11(1):18-31.

Krystal, "A Simple Microassay for Erythropoietin Based on $^3$H-Thymidine Incorporation into Spleen Cells from Phenylhydrazine Treated Mice," *Exp. Hematol.*, 1983, 11(7):649-660.

Krystal et al., "Purification of Human Erythropoietin to Homogeneity by a Rapid Five-Step Procedure," *Blood*, 1986, 67(1):71-79.

Kuberan et al., "Preparation and isolation of neoglycoconjugates using biotin-streptavidin complexes," *Glycoconj. J.*, 1999, 16:271-281.

Kurtz and Eckardt, "Assays for Erythropoietin," *Nephron.*, 1989, 51(suppl 1):11-14 (w/English summary).

Larionova et al., "Conjugation of the Bowman-Birk Soybean Proteinase Inhibitor with Hydroxyethylstarch," *Appl. Biochem. Biotech.*, 1997, 62:175-182.

Lee (ed.), "Synthesis of Peptides and Proteins," *Peptide and Protein Drug Delivery*, 1991, p. 65.

Lee and Lee, "Neoglycoproteins," *Glycoproteins II*, 1997, Chapter 17, Elsevier Science B.V., pp. 301-620.

Leenders et al., "β-Glucuronyl Carbamate Based Pro-moieties Designed for Prodrugs in ADEPT," *Tetrahedron Letters*, 1995, 36(10):1701-1704.

Lees et al., "Activation of soluble polysaccharides with 1-cyano-4-dimethylaminopyridinium tetrafluoroborate for use in protein-polysaccharide conjugate vaccines and immunological reagents," *Vaccine*, 1996, 14(3):190-198.

Lesnefsky et al., "High-Dose Iron-Chelator Therapy During Reperfusion with Deferoxamine-Hydroxyethyl Starch Conjugate Fails to Reduce Canine Infarct Size," *J. Cardiovasc. Pharmacol.*, 1990, 16(4):523-528.

Lin et al., "Cloning and expression of the human erythropoietin gene," *Proc. Natl. Acad. Sci. USA*, 1985, 82:7580-7584.

Lindsey at al., "Porphyrin Building Blocks for Modular Construction of Bioorganic Model Systems," *Tetrahedron*, 1994, 50(30):8941-8968, especially p. 8956.

Lomant and Fairbanks, "Chemical Probes of Extended Biological Structures: Synthesis and Properties of the Cleavable Protein Cross-linking Reagent [$^{35}$S]Dithiobis(succinimidyl propionate)," *J. Mol. Biol.*, 1976, 104:243-261.

Lönngren and Goldstein, "Coupling of Aldobionic Acids to Proteins Using Water-Soluble Carbodiimide," *Meth. Enzymol.*, 1994, 242:116-118.

Manger et al., "1-*N*-Glycyl β-Oligosaccharide Derivatives as Stable Intermediates for the Formation of Glycoconjugate Probes," *Biochemistry*, 1992, 31:10724-10732.

Manger et al., "Synthesis of 1-*N*-Glycyl β-Oligosaccharide Derivatives. Reactivity of *Lens culinaris* Lectin with a Fluorescent Labeled Streptavidin Pseudoglycoprotein and Immobilized Neoglycolipid," *Biochemistry*, 1992, 31:10733-10740.

Maout et al., "Hydroxyethylstarch Conjugated to Human Hemoglobin for use in Blood Transfusion: Comparison with Dextran Conjugates," *Carbohydrates and Carbohydrate Polymers—Analysis, Biotechnology, Modification, Antiviral and Other Applications*, 1993, Chapter 12, pp. 132-140.

McMahon et al., "Pharmacokinetics and Effects of Recombinant Human Erythropoietin After Intravenous and Subcutaneous Injections in Healthy Volunteers," *Blood*, 1990, 76(9):1718-1722.

Meinjohanns et al., "Novel sequential solid-phase synthesis of N-linked glycopeptides from natural sources," *J. Chem. Soc., Perkin Trans. 1*, 1998, 1:549-560.

Mikola and Hänninen, "Introduction of Aliphatic Amino and Hydroxy Groups to Keto Steroids Using O-Substituted Hydroxylamines," *Bioconj. Chem.*, 1992, 3(2):182-186.

Minnema et al., "Recombinant human antithrombin III improves survival and attenuates inflammatory responses in baboons lethally challenged with *Escherichia coli*," *Blood*, 2000, 95(4): 1117-1123.

Miyake et al., "Purification of Human Erythropoietin," *J. Biol. Chem.*, 1977, 252(15):5558-5564.

Montreuil et al., "Hexuronic acids," *Carbohydrate analysis: a practical approach*, 1996, Chaplin and Kennedy (eds.), Chapter 5, pp. 175-204.

Mosbech et al., "Hyposensitization in asthmatiCs with mPEG-modified and unmodified house dust mite extract," *Allergy*, 1990, 45(2):130-141.

Mosmann, "Rapid Colorimetric Assay for Cellular Growth and Survival: Application to Proliferation and Cytotoxicity Assays," *J. Immunol. Meth.*, 1983, 65:55-63.

Mueller et al., "Recombinant Glycoprotein Product Quality in Proliferation-Controlled BHK-21 Cells," *Biotechnol. Bioeng.*, 1999, 65(5):529-536.

Davis and Flitsch, "A Novel Method for the Specific Glycosylation of Proteins," *Tetrahedron Lett.*, 1991, 32(46):6793-6796.

Nagata et al., "The chromosomal gene structure and two mRNAs for human granulocyte colony-stimulating factor," *EMBO J.*, 1986, 5(3):575-581.

Nagata et al., "Molecular cloning and expression of cDNA for human granulocyte colony-stimulating factor," *Nature*, 1986, 319:415-418.

(56) References Cited

OTHER PUBLICATIONS

Nakane et al., "The Accumulation Mechanism of Cationic Mitomycin C-dextran Conjugates in the Liver: In-vivo Cellular Localization and In-vitro Interaction with Hepatocytes," *J. Pharm. Pharmacol.*, 1988, 40:1-6.
Nedospasov and Khomutov, "Synthesis and some properties of aminooxyalkylcelluloses," *Bulletin of the Academy of Sciences of the USSR*, 1976, Division of Chemical Science, Consultants Bureau, New York, 25:1105-1110.
Nimtz et al., "Structural characterization of the oligosaccharide chains of native and crystallized boar seminal plasma spermadhesin PSP-I and PSP-II glycoforms," *Eur. J. Biochem.*, 1999, 265:703-718.
Nimtz et al., "Structures of sialylated oligosaccharides of human erythropoietin expressed in recombinant BHK-21 cells," *Eur. J. Biochem.*, 1993, 213:39-56.
Nimtz et al., "Carbohydrate structures of a human tissue plasminogen activator variant expressed in recombinant Chinese hamster ovary cells," *FEBS Lett.*, 1990, 271:14-18.
Nohynek et al., "Comparison of the potency of glycosylated and nonglycosylated recombinant human granulocyte colony-stimulating factors in neutropenic and nonneutropenic CD rats," *Cancer Chemother Pharmacol.*, 1997, 39:259-266.
Nomura et al., "Pharmacokinetic characteristics and therapeutic effects of mitomycin C-dextran conjugates after intratumoural injection," *J. Controlled Release*, 1998, 52:239-252.
O'Shannessy and Wilchek, "Immobilization of Glycoconjugates by Their Oligosaccharides: Use of Hydrazido-Derivatized Matrices," *Analytical Biochemistry*, 1990, 191:1.
Pawlowski et al., "A new method of non-cross-linking conjugates of polysaccharides to protein via thioether bonds for the preparation of saccharide-protein conjugate vaccines," *Vaccine*, 1999, 17:1474-1483.
Pazur, "Neutral polysaccharides," *Carbohydrate analysis: a practical approach*, 1996, Chaplin and Kennedy (eds.), Chapter 3, pp. 55-96.
Pedley et al., "The potential for enhanced tumour localization by poly)ethylene glycol) modification of anti-CEA antibody," *Br. J. Cancer*, 1994, 70:1126-1130.
Peeters et al., "Comparison of four bifunctional reagents for coupling peptides to proteins and the effect of the three moieties on the immunogenicity of the conjugates," *J. Immunol. Meth.*, 1989, 120:133-143.
Peron et al., "Hydroxyethyl starch-induced renal insufficiency after plasma exchange in a patient with polymyositis and liver cirrhosis," *Clin. Nephrol.*, 2001, 55(5):408-411.
*Pharma Business*, Jul./Aug. 2000, pp. 45-60.
Quelle et al., "High-Level Expression and Purification of a Recombinant Human Erythropoietin Produced Using a Baculovirus Vector," *Blood*, 1989, 74(2):652-657.
Rabiner et al., "Evaluation of a stroma-free hemoglobin solution for use as a plasma expander," *J. Exp. Med.*, 1967, 126:1127-1142.
Ragupathi et al., "A novel and efficient method for synthetic carbohydrate conjugate vaccine preparation: synthesis of sialyl Tn-KLH conjugate using a 4-(4-N-maleimidomethyl) cyclohexane-1-carboxyl hydrazide (MMCCH) linker arm," *Glycoconj. J.*, 1998, 15:217-221.
Ramos et al., "Enzymatic Synthesis of Neoglycopeptide Building Blocks," *Angew. Chem. Int. Ed.*, 2000, 39(2):396-398.
Relihan et al., "Clearance Rate and Effect on Renal Function of Stroma-Free Hemoglobin Following Renal Ischemia," *Ann. Surg.*, 1972, 176(6):700-704.
Richter and de Belder, "Antibodies against Hydroxyethylstarch Produced in Rabbits by Immunization with a Protein-Hydroxyethylstarch Conjugate," *Int. Arch. Allergy Appl. Immun.*, 1976, 52:307-314.
Rogers et al., "Effects of polymerization on the oxygen carrying and redox properties of diaspirin cross-linked hemoglobin," *Biochim. Biophys. Acta*, 1995, 1248:135-142.
Rohrling et al., "Synthesis and testing of a novel fluorescene label for carbonyls in carbohydrates and cellulosics," *Synlett*, 2001, 5:682-684.
Rose, "Facile Synthesis of Homogeneous Artificial Proteins," *J. Am. Chem. Soc.*, 1994, 116:30-33.
Rudolph et al., "Circulation persistence and biodistribution of lyophilized liposome-encapsulated hemoglobin: An oxygen-carrying resuscitative fluid," *Crit. Care Med.*, 1994, 22:142-150.
Rudolph, "The Freeze-Dried Preservation of Liposome Encapsulated Hemoglobin: A Potential Blood Substitute," *Cryobiology*, 1988, 25:277-284.
Rush et al., "Microheterogeneity of Erythropoietin Carbohydrate Structure," *Anal. Chem.*, 1995, 67(8):1442-1452.
Ruttmann et al., "In vivo investigation into the effects of haemodilution with hydroxyethylstarch (200/0.5) and normal saline on coagulation," *Br. J. Anaesthesia*, 1998, 80(5):612-616.
Sadamoto et al., "Control of Bacteria Adhesion by Cell-Wall Engineering," *J. Am. Chem. Soc.*, 2004, 126:3755-3761.
Sadrzadeh et al., "The Long-Acting Parenteral Iron Chelator, Hydroxyethyl Starch-Deferoxamine, Fails to Protect Against Alcohol-Induced Liver Injury in Rats," *J. Pharmacol. Exp. Ther.*, 1997, 280(2):1038-1042.
Sakai et al., "Synthesis and Physicochemical Characterization of a Series of Hemoglobin-Based Oxygen Carriers: Objective Comparison between Cellular and Acellular Types," *Bioconj. Chem.*, 2000, 11:56-64.
Sato et al., "Disposition of a Polymeric Prodrug of Mitomycin C, Mitomycin C-Dextran Conjugate, in the Perfused Rat Liver," *J. Pharm. Sci.*, 1989, 78:11-16.
Sawaikar et al., "Products active on mosquitoes. Part VII, Synthesis and biological activity of longifolene derivatives," *Indian Journal of Chemistry*, 1995, 34B:832-835.
Scaglione et al., "A New Model Examining Intracellular and Extracellular Activity of Amoxicillin, Azithromycin, and Clarithromycin in Infected Cells," *Chemotherapie*, 1993, 39:416-423.
Schäfer et al., "Two-year double-blind trial of a monomethoxy polyethylene glycol (mPEG) modified grass pollen extract at different dose levels," *Ann. Allergy*, 1992, 68(4):334-339.
Schlenke et al., "Construction and characterization of stably transfected BHK-21 cells with human-type sialylation characteristic," *Cytotechnology*, 1999, 30:17-25.
Schottelius et al., "Improvement of Pharmacokinetics of Radioiodinated Tyr$^3$-Octreotide by Conjugation with Carbohydrates," *Bioconjugate Chem.*, 2002, 13:1021-1030.
Shafer et al., "Activation of soluble polysaccharides with 1-cyano-4-dimethylaminopyridinium tetrafluoroborate (CDAP) for use in protein-polysaccharide conjugate vaccines and immunological reagents. II. Selective crosslinking of proteins to CDAP-activated polysaccharides," *Vaccine*, 2000, 18:1273-1281.
Shah et al., "Characterization of Colony-stimulating Activity Produced by Human Monocytes and Phytohemagglutinin-stimulated Lymphocytes," 1977, *Blood*, 50(5):811-821.
Shirafuji et al., "A new bioassay for human granulocyte colony-stimulating factor (hG-CSF) using murine myeloblastic NFS-60 cells as targets and estimation of its levels in sera from normal healthy persons and patients with infectious and hematological disorders," *Exp. Hematol.*, 1989, 17:116-119.
Simmons et al., "Potent inhibition of HIV-1 infectivity in macrophages and lymphocytes by a novel CCR5 antagonist," *Science*, 1997, 276:276-279.
Snyder et al., "HbXL99α A hemoglobin derivative that is cross-linked between the α subunits is useful as a blood substitute," *Proc. Natl. Acad. Sci. USA*, 1987, 84:7280-7284.
Shu, "Somogyi Micro Copper Method," *Method in Carbohydride Chemistry*, 1962, 1:383-388.
Song et al., "Toxicity and Antitumor Activity of the Conjugate of Mitomycin C with Carboxymethyl-chitin," *Arch. Pract. Pharm.*, 1993, 53(3):141-147.
Souza et al., "Recombinant human granulocyte colony-stimulating factor: effects on normal and leukemic myeloid cells," *Science* 1986, 232:61-65.

(56) References Cited

OTHER PUBLICATIONS

Soyez et al., "Biological evaluation of mitomycin C bound to a biodegradable polymeric carrier," *J. Controlled Release*, 1997, 47:71-80.
Spivak and Hogans, "The in Vivo Metabolism of Recombinant Human Erythropoietin in the Rat," *Blood*, 1989, 73:90-99.
Staros, "*N*-Hydroxysulfosuccinimide Active Esters: Bis(*N*-hydroxysulfosuccinimide) Esters of Two Dicarboxylic Acids Are Hydrophilic, Membrane-Impermeant, Protein Cross-Linkers," *Biochemistry*, 1982, 21:3950-3955.
Sunamoto and Iwamoto, "Protein-Coated and Polysaccharide-Coated Liposomes as Drug Carriers," *CRC Critical Review in Therapeutic Drug Carrier Systems*, 1986, 2:117-136.
Sytkowski et al., "Human erythropoietin dimers with markedly enhanced in vivo activity," *Proc. Natl. Acad. Sci. USA*, 1998, 95(3):1184-1188.
Sytkowski et al., "An Erythropoietin Fusion Protein Comprised of Identical Repeating Domains Exhibits Enhanced Biological Properties," *J. Biol. Chem.*, 1999, 274(35):24773-24778.
Takeuchi et al., "Relationship between sugar chain structure and biological activity of recombinant human erythropoietin produced in Chinese hamster ovary cells," *Proc. Natl. Acad. Sci. USA*, 1989, 86:7819-7822.
Takeuchi and Kobata, "Structures and functional roles of the sugar chains of human erythropoietin," *Glycobiology*, 1991, 1(4):337-346.
Tam et al., "Soluble Dextran-Hemoglobin Complex as a Potential Blood Substitute," *Proc. Natl. Acad. Sci. USA*, 1976, 73(6):2128-2131.
Tanaka et al., "Pharmacokinetics of recombinant human granulocyte colony-stimulating factor conjugated to polyethylene glycol in rats," *Cancer Research*, 1991, 51:3710-3714.
Thomas et al., "Measuring blood volume with fluorescent-labeled hydroxyethyl starch," *Crit. Care Med.*, 2000, 28(3):627-631.
Thomas, "Carbohydrate Binding Sites," *Meth. Enzymol.*, 1977, 46:362-368.
Thorpe et al., "Blockade of the galactose-binding sites of ricin by its linkage to antibody," *Eur. J. Biochem.*, 1984, 140:63-71.
Toyama et al., "Surface design of SPR-based immunosensor for the effective binding of antigen or antibody mixed polymer matrix," *Sensors and Actuators B*, 1998, 52:65-71.
De Velasco et al., "Synthetic Peptides Representing T-Cell Epitopes Act as Carriers in Pneumococcal Polysaccharide Conjugate Vaccines," *Infect. Immun.*, 1995, 63(3):961-968.
Van Patten et al., "Oxidation of Methionine Residues in Antithrombin," *J. Biol. Chem.*, 1999, 274(15):10268-10276.
Veronese et al., "Surface Modification of Proteins. Activation of Monomethoxy-Polyethylene Glycols by Phenylchloroformates and Modification of Ribonuclease and Superoxide Dismutase," *Appl. Biochem. Biotech.*, 1985, 11:141-152.
Vilaseca et al., "Protein conjugates of defined structure: Synthesis and use of a new carrier molecule," *Bioconjugate Chemistry*, 1993, 4(6):515-520.
Webb II and Kaneko, "Synthesis of 1-(Aminooxy)-4-[(3-nitro-2-pyridyl)dithio]butane and 1-(Aminooxy)-4-[(3-nitro-2-pyridyl)dithio]but-2-ene, Novel Heterobifunctional Cross-Linking Reagents," *Bioconjugate Chem.*, 1990, 1:96-99.
Weidler et al., "Pharmakokinetische Merkmale als Kriterien für den klinischen Einsatz von Hydroxyethylstärke," *Arzneim.-Forsch./Drug Res.*, 1991, 41:494-498 (w/English summary).
White and Kennedy, "Oligosaccharides," *Carbohydrate analysis: a practical approach*, 1996, Chaplin and Kennedy (eds.), Chapter 2, pp. 1-36.
Whitesides et al., "Rates of Thiol-Disulfide Interchange Reactions between Mono- and Dithiols and Ellman's Reagent," *J. Org. Chem.*, 1977, 42(2):332-338.
Wong et al., "Analysis of carbohydrate-protein interactions with synthetic N-linked neoglycoconjugate probes," *Biochem. J.*, 1993, 296:817-825.

Wong et al., "Synthetic glycosylation of proteins using *N*-β-saccharide) iodoacetamides: applications in site-specific glycosylation and solid-phase enzymic oligosaccharide synthesis," *Biochem. J.*, 1994, 300:843-850.
Wong, *Chemistry of protein conjugation and cross-linking*, 1993, CRCS, Inc. (TOC only).
Xue and Wong; "Preparation of Conjugated Hemoglobins," *Meth. Enzymol.*, 1994, 231:308-322.
Yalpani et al., "Selective Chemical Modifications of Dextran," *J. Polymer Science: Polymer Chemistry Edition*, 1985, 23:1395-1405.
Yamaguchi et al., "Effects of site-directed removal of N-glycosylation sites in human erythropoietin on its production and biological properties," *J. Biol. Chem.*, 1991, 266(30):20434-20439.
Yoshida, "Glycamine Formation via Reductive Amination of Oligosaccharides with Benzylamine," *Meth. Enzymol.*, 1994, 247:55-64.
Zalipsky, "Functionalized Poly(ethylene glycol) for Preparation of Biologically Relevant Conjugates," *Bioconjugate Chem.*, 1995, 6:150-165.
Zara et al., "A Carbohydrate-Directed Heterobifunctional Cross-Linking Reagent for the Synthesis of Immunoconjugates," *Anal. Biochem.*, 1991, 194:156-162.
Zettlmeissl et al., "Characterization of Recombinant Human Antithrombin III Synthesized in Chinese Hamster Ovary Cells," *J. Biol. Chem.*, 1989, 264 (35):21153-21159.
Zhou et al., "Application of capillary electrophoresis, liquid chromatography, electrospray-mass spectrometry and matrix-assisted laserdesorption/ionization—time of flight—mass spectrometry to the characterization of recombinant human erythropoietin," *Electrophoresis*, 1998, 19(13):2348-2355.
Zou et al., "Allylmalonamide as a bivalent linker: Synthesis of biantennary $Gm_3$-saccharide-Keyhole limpet hemocyanin glycoconjugate and the immune response in mice," *Glycoconj. J.*, 1999, 16:507-515.
Zucali and Sulkowski, "Purification of human urinary erythropoietin on controlled-pore glass and silicic acid," *Exp. Hematol.*, 1985, 13(3):833-837.
Definition of dimethyl sulfoxide, the Merck Index, 2006, Merck & Co., 14th edition, accessed online http://themerckindex.cambridgesoft.com/TheMerckIndex/index.asp on Sep. 4, 2007.
Sakai et al. "Synthesis and Physicochemical Characterization of a series of Hemoglobin-Based Oxygen Carriers: Objective Comparison between Cellular and Acellular Types," Bioconjugate Chem., 2000, 11:56-64.
Adamczyk and Fishpaugh, "A Solid Supported Synthesis of Thiol Esters," *Tetrahedron Lett.*, 1996, 37(25):4305-4308.
Aly et al., "Hemophilia A due to mutations that create new N-glycosylation sites," *Proc. Natl. Acad. Sci. USA*, 1992, 89:4933-4937.
Andersson et al., "Isolation and characterization commercial factor VIII: Molecular forms in commercial factor VIII concentrate, cryoprecipitate, and plasma," *Proc. Natl. Acad. Sci. USA*, 1986, 83:2979-2983.
Armitage, "Emerging Applications of Recombinant Human Granulocyte-Macrophage Colony-Stimulating Factor," *Blood*, 1998, 92(12):4491-4508.
Balland et al., "Characterisation of two differently processed forms of human recombinant factor IX with synthesised in CHO cells transformed with a polycistronic vector," *Eur. J. Biochem.*, 1988, 172(3):565-572.
Bauer and Rosenberg, "Role of Antithrombin III as a Regulator of In Vivo Coagulation," *Semin. Hematol.*, 1991, 28:10-18.
Berg et al., "Engineering the proteolytic specificity of activated protein C improves its pharmacological properties," *Proc. Natl. Acad. Sci. USA*, 2003, 100(8):4423-4428.
Bhattacharyya et al., "Recombinant Factor VIII for Haemophilia An Overview of Production Technologies," *CRIPS*, 2003, 4(3):2-8.
Björk and Danielsson, "Antithrombin and related inhibitors of coagulation proteinases," *Proteinase Inhibitors*, 1986, Chapter 17, pp. 489-513.
Boorsma et al., "Bioprocess Applications of a Sindbis Virus-Based Temperature-Inducible Expression System," *Biotech. Bioeng.*, 2002, 79(6): 602-609.

(56) References Cited

OTHER PUBLICATIONS

Carrell et al., "Human $\alpha_1$-antitrypsin: carbohydrate attachment and sequence homology," *FEBS Lett.*, 1981, 135(2):301-303.
Carrell et al., "Structural Mobility of Antithrombin and its Modulation by Heparin," *Thromb Haemost.*, 1997, 78:516-519.
Carver et al., "Expression of human α1 antitrypsin in transgenic sheep," *Cytotechnology*, 1992, 9:77-84.
Castillo et al., "Sensitive Substrates for Human Leukocyte and Porcine Pancreatic Elastase: A Study of the Merits of Various Chromophoric and Fluorogenic Leaving Groups in Assays for Serine Proteases," *Anal. Biochem.*, 1979, 99:53-64.
Cebon et al., "Granulocyte-Macrophage Colony Stimulating Factor from Human Lymphocytes. The effect of glycosylation on receptor binding and biological activity," *J. Biol. Chem.*, 1990, 265(8):4483-4491.
Chamow and Ashkenazi, *Antibody Fusion Proteins*, 1999, Wiley & Sons, Inc. (TOC Only).
Chan et al., "Preparation of O-esters from the corresponding thiol esters: *tert*-butyl cyclohexanecarboxylate," *Organic Syntheses, Coll.*, 1990, 7:87-93.
Chen et al., "Purification of $\alpha_1$ Proteinase Inhibitor from Human Plasma Fraction IV-1 by Ion Exchange Chromatography," *Vox Sang*, 1998, 74:232-241.
Choay et al., "Structural studies on a biologically active hexasaccharide obtained from heparin," *Ann. NY Acad. Sci.*, 1981, 370:644-649.
Choay et al., "Structure-activity relationship in heparin: a synthetic pentasaccharide with high affinity for antithrombin III and eliciting high anti-factor Xa activity," *Biochem. Biophys. Res. Commun.*, 1983, 116(2):492-499.
Colman, "Production of therapeutic proteins in the milk of transgenic livestock," *Biochem. Soc. Symp.*, 1998, 63:141-147.
Conradt et al., "Expression of Human Interleukin-2 in Recombinant Baby Hamster Kidney, Ltk, and Chinese Hamster Ovary Cells. Structure of O-linked carbohydrate chains and their location within the polypeptide," *J. Biol. Chem.*, 1989, 264(29):17368-17373.
Corey and Clark, "A new method for the synthesis of 2-pyridinethiol carboxylic esters," *Tetrahedron Lett.*, 1979, 31:2875-2878.
de Koning et al., "An approach to the synthesis of peptide-PNA-peptide conjugates via native ligation," *Tetrahedron Lett.*, 2002, 43(45): 8173-8176.
Denzlinger et al., "Differential Activation of the Endogenous Leukotriene Biosynthesis by Two Different Preparations of Granulocyte-Macrophage Colony-Stimulating Factor in Healthy Volunteers," *Blood*, 1993, 81(8):2007-2013.
Donahue et al., "Effects of N-linked Carbohydrates on the in Vivo Properties of Human GM-CSF," *Cold Spring Harbor Symp. Quant. Biol.*, 1986, 51:685-692.
Edmunds et al., "Transgenically Produced Human Antithrombin: Structural and Functional Comparison to Human Plasma-Derived Antithrombin," *Blood*, 1998, 91(12):4561-4571.
Ernst et al. (eds.), *Carbohydrates in Chemistry and Biology*, 2000, Part I, vol. 1-2, Whiley-VCH Weinheim (TOC only).
European Pharmacopoeia, 2001, 911-917.
Forno et al., "N- and O-linked carbohydrates and glycosylation site occupancy in recombinant human granulocyte-macrophage colony-stimulating factor secreted by a Chinese hamster ovary cell line," *Eur. J. Biochem.*, 2004, 271(5):907-919.
Franzen and Svensson, "Structural Studies on the Carbohydrate Portion of Human Antithrombin III," *J. Biol. Chem.*, 1980, 255(11):5090-5093.
Fujiki et al., "Studies on the disulfide bonds in human pituitary follicle-stimulating hormone," *Biochim. Biophys. Acta*, 1980, 624: 428-435.
Goldstein and Gelb, "An alternate preparation of thioester resin linkers for solid-phase synthesis of peptide C-terminal thioacids," *Tetrahedron Lett.*, 2000, 41(16):2797-2800.
Goronzy et al., "T-Cell Derived Lymphokines as Regulators of Chronic Inflammation: Potential Targets for Immunomodulation?" *Am. J. Ther.*, 1996, 3(2):109-114.

Gribben et al., "Development of antibodies to unprotected glycosylation sites on recombinant GM-CSF," *Lancet*, 1990, 335:434-437.
Harris et al., "Pegylation. A novel process for modifying pharmacokinetics," *Clin. Pharmacokinet*, 2001, 40(7): 539-551.
He et al., "A simplified system for generating recombinant adenoviruses," *Proc. Natl. Acad. Sci. USA*, 1998, 95:2509-2514.
Hodges and Chan, "Locations of Oligosaccharide Chains in Human α1-Protease Inhibitor and Oligosaccharide Structures at Each Site," *Biochemistry*, 1982, 21:2805-2810.
Hodges et al., "Structure of the Oligosaccharide Chains in Human $\alpha_1$-Protease Inhibitor," *J. Biol. Chem.*, 1979, 254(17):8208-8212.
Hovgaard et al., "Clinical pharmacokinetic studies of a human haemopoietic growth factor, GM-CSF," *Eur. J. Clin. Inv.*, 1992, 22:45-49.
Hovinen et al., "Ethyl[2-deoxy-5-0-(4,4'-dimethoxytrityl)-α-and β-D-*erythro*-pentofuranosyl]acetates as versatile intermediates in nucleic acid chemistry," *Nucleosides Nucleotides*, 1999, 18:1263-1264.
Iakovenko et al., "Semi-synthetic Rab proteins as tools for studying intermolecular interactions," *FEBS Letters*, 2000, 468:155-158.
Ingenito et al., "Solid Phase Synthesis of Peptide C-Terminal Thioesters by Fmoc/t-Bu Chemistry," *J. Am. Chem. Soc.*, 1999, 121:11369-11374.
Jaques et al., "N.M.R. spectroscopy and calcium binding of sialic acids: N-glycolylneuraminic acid and periodate-oxidized N-acetylneuraminic acid," *Carb. Res.*, 1980, 83:21-32.
Karpusas et al., The crystal structure of human interferon β at 2.2-Å resolution, *Proc. Natl. Acad. Sci. USA*, 1997, 94:11813-11818.
Kaufman et al., "Synthesis, Processing, and Secretion of Recombinant Human Factor VIII Expressed in Mammalian Cells," *J. Biol. Chem.*, 1988, 263(13):6352-6362.
Kaushansky et al., "Role of Carbohydrate in the Function of Human Granulocyte-Macrophage Colony-Stimulating Factor," *Biochemistry*, 1987, 26:4861-4867.
Keene et al., "Expression of Biologically Active Human Follitropin in Chinese Hamster Ovary Cells," *J. Biol. Chem.*, 1989, 264(9):4769-4775.
Kochendoerfer et al., "Design and Chemical Synthesis of a Homogeneous Polymer-Modified Erythropoiesis Protein," *Science*, 2003, 299(5608):884-887.
Kraehenbuhl et al., "Preparation and characterization of an immuno-electron microscope tracer consisting of a heme-octapeptide coupled to Fab," *J. Exp. Med.*, 1974, 139:208-223.
Lahiri et al., "Antithrombin-Heparin Cofactor: An Inhibitor of Plasma Kallikrein," *Arch. Biochem. Biophys.*, 1976, 175:737-747.
Lapthorn et al., "Crystal structure of human chorionic gonadotropin," *Nature*, 1994, 369:455-461.
Levy et al., "Recombinant Antithrombin: Production and Role in Cardiovascular Disorder," *Sem. Thromb. Hem.*, 2001, 27(4):405-416.
Li et al., "Direct preparation of peptide thioesters using an Fmoc solid-phase method," *Tetrahedron Lett.*, 1998, 39(47):8669-8672.
Lin et al., "L-Cysteine as a water-soluble cation scavenger in the removal of the 2,4,6-trimethoxybenzyl group from thiols," *Tetrahedron Lett.*, 2002, 43:4531-4533.
March, "Delocalized Chemical Bonding," *Adv. Org. Chem.*, 1992, 4th Edition, John Wiley and Sons, New York, Chapter 2 pp. 26-292.
Masamune et al., "A General Selective Synthesis of Thiol Esters," *Can. J. Chem.*, 1975, 53:3693-3695.
Masamune et al., "Tylonolide Hemiacetal, the Aglycone of Tylosin, and Its Partial Synthesis," *J. Am. Chem. Soc.*, 1976, 98:7874-7875.
Masuda et al., "Synthesis and Anti-Influenza Evaluation of Orally Active Bicyclic Ether Derivatives Related to Zanamivir," *Bioorganic & Medicinal Chemistry Letters*, 2003, 13:669-673.
Mega et al., "Studies on the Oligosaccharide Chains of Human $\alpha_1$-Protease Inhibitor. I. Isolation of glycopeptides," *J. Biol. Chem.*, 1980, 255(9):4053-4056.
Mega et al., "Studies on the Oligosaccharide Chains of Human $\alpha_1$-Protease Inhibitor. II. Structure of oligosaccharides," *J. Biol. Chem.*, 1980, 255(9):4057-4061.
Menache, "Antithrombin III: Introduction," *Semin. Hematol.*, 1991, 28:1-2.
Menache et al., "Antithrombin III: physiology, deficiency, and replacement therapy," *Transfusion*, 1992, 32:580-588.

(56) References Cited

OTHER PUBLICATIONS

Ming et al., "Interleukin 6 is the Principal Cytolytic T Lymphocyte Differentiation Factor for Thymocytes in Human Leukocyte Conditioned Medium," *J. Mol. Cell. Immunol.*, 1989, 4:203-212.

Moonen et al., "Increased biological activity of deglycosylated recombinant human granulocyte/macrophage colony-stimulating factor produced by yeast or animal cells," *Proc. Natl. Acad. Sci. USA*, 1987, 84:4428-4431.

Mori et.al., "The Activation of Type 1 and Type 2 Plasminogen by Type I and Type II Tissue Plasminogen Activator," *J. Biol. Chem.*, 1995, 270(7):3261-3267.

Muir et al., "Expressed protein ligation: A general method for protein engineering," *Proc. Natl. Acad. Sci. USA*, 1998, 95:6705-6710.

Mukaiyama et al., "Peptide Synthesis via Oxidation-Reduction Condensation by the Use of Non-metallic Compound as a Mercaptan Scavenger," *Bull. Chem. Soc. Jpn.*, 1970, 43:1271.

Mumberg et al., "Regulatable promoters of *Saccharomyces cerevisiae*: comparison of transcriptional activity and their use for heterologous expression," *Nucl. Acids Res.*, 1994, 22(25):5767-5768.

Murano et al., "Some properties of antithrombin-III and its concentration in human plasma," *Thromb. Res.*, 1980, 18:259-262.

Ohta et al., "Usefulness of Glycopeptide Mapping by Liquid Chromatography/Mass Spectrometry in Comparability Assessment of Glycoprotein Products," *Biologicals*, 2002, 30(3):235-244.

Okamoto et al., "Purification and Characterization of Three Forms of Differently Glycosylated Recombinant Human Granulocyte-Macrophage Colony-Stimulating Factor," *Arch. Biochem. Biophys.*, 1991, 286(2):562-568.

Olson et al., "Role of the Antithrombin-binding Pentasaccharide in Heparin Acceleration of Antithrombin-Proteinase Reactions. Resolution of the antithrombin conformational change contribution to heparin rate enhancement," *J. Biol. Chem.*, 1992, 267(18):12528-12538.

Olson and Björk, "Predominant Contribution of Surface Approximation to the Mechanism of Heparin Acceleration of the Antithrombin-Thrombin Reaction. Elucidation from salt concentration effects," *J. Biol. Chem.*, 1991, 266(10):6353-6364.

Opal et al., "Antithrombin, heparin, and heparan sulfate," *Crit. Care Med.*, 2002, 30(5):S325-S331.

Pelter et al., "Synthesis of Thioesters by Reactions of Carboxylic Acids with Tris-(ethylthio)borane," *J. Am. Chem. Soc., Perkin Trans I*, 1977, 1672-674.

Peterson, *The Physiological Inhibitions of Blood Coagulation and Fibrinolysis*, 1979, Elsevier/North-Holland Biomedical Press, p. 43.

Pike et al., "Heparin-dependent Modification of the Reactive Center Arginine of Antithrombin and Consequent Increase in Heparin Binding Affinity," *J. Biol. Chem.*, 1997, 272_32:19652-19655.

Ragnhammar et al., "Induction of Anti-Recombinant Human Granulocyte-Macrophage Colony-Stimulating Factor (*Escherichia coli*-Derived) Antibodies and Clinical Effects in Nonimmunocompromised Patients," *Blood*, 1994, 84(12):4078-4087.

Rapoport et al., "Protein transport across the eukaryotic endoplasmic reticulum and bacterial inner membranes," *Annu. Rev. Biochem.*, 1996, 65:271-303.

Reddy et al., "Use of peginterferon alfa-2a (40 KD) (Pegasys®) for the treatment of hepatitis C," *Advanced Drug Delivery Reviews*, 2002, 54:571-586.

Reischl (ed)., *Molecular Diagnosis of Infectious Diseases*, 1997, vol. 13, Totowa NJ, Humana Press Inc. (TOC Only).

Reidhaar-Olson et al., "Identification of Residues Critical to the Activity of Human Granulocyte Colony-Stimulating Factor," *Biochemistry*, 1996, 35:9034-9041.

Revoltella et al., "Natural and Therapy-Induced Anti-GM-CSF and Anti-G-CCSF Antibodies in Human Serum," *Leukemia and Lymphoma*, 1997, 26:29-34.

Roemisch et al., "Antithrombin: a new look at the actions of a serine protease inhibitor," *Blood Coagul. Fibrinolysis*, 2002, 13:657-670

Rosenberg, "Role of heparin and heparinlike molecules in thrombosis and atherosclerosis," *Fed. Proc.*, 1985, 44:404-409.

Rosenberg et al., "Antithrombin-III," *Rev. Hematol.*, 1986, 2:351-416.

Schlesinger, "Alphaviruses—vectors for the expression of heterologous genes," *Trends Biotech.*, 1993, 11:18-22.

Schröter et al., "Male-specific Modification of Human CD52," *J. Biol. Chem.*, 1999, 274(42):29862-29873.

Shin et al., "Fmoc-Based Synthesis of Peptide-$\alpha$Thioesters: Application to the Total Chemical Synthesis of a Glycoprotein by Native Chemical Ligation," *J. Am. Chem. Soc.*, 1999, 121:11684-11689.

Spellman et al., "Carbohydrate Structures of Human Tissue Plasminogen Activator Expressed in Chinese Hamster Ovary Cells," *J. Biol. Chem.*, 1989, 264(24):14100-14111.

Stetsenko and Gait, "Efficient Conjugation of Peptides to Oligonucleotides by Native Ligation," *J. Org. Chem.*, 2000, 65:4900-4908.

Stewart et al., "Identification of the Mechanism Responsible for the Increased Fibrin Specificity of TNK-Tissue Plasminogen Activator Relative to Tissue Plasminogen Activator," *J. Biol. Chem.*, 2000, 275(14):10112-10120.

Tebbutt, "Technology evaluation: transgenic $\alpha$-1-antitrypsin (AAT), PPL Therapeutics," *Curr. Opin. Mol. Ther.*, 2000, 2(2):199-204.

Thim et al., "Amino Acid Sequence and Posttranslational Modification of Human Factor VII$_a$ from Plasma and Transfected Baby Hamster Kidney Cells," *Biochemistry*, 1988, 27:7785-7793.

Toole et al., "Molecular cloning of a cDNA encoding human antihaemophilic factor," *Nature*, 1984, 312:342-347.

Travis and Salvesen, "Human plasma proteinase inhibitors," *Ann. Rev. Biochem.*, 1983, 52:655-709.

Veronese et al., "Peptide and Protein PEGylation—A Review of Problems and Solutions," *Biomaterials*, 2001, 22(5):405-417.

Wadhwa et al., "Immunogenic ity of Granulocyte-Macrophage Colony-Stimulating Factor (GM-CSF) Products in Patients Undergoing Combination Therapy with GM-CSF," *Clin. Cancer Res.*, 1999, 5:1351-1361.

Watanabe et al., "A facile synthesis of carboxylic thiol esters from carboxylic acids and thiols," *Chem. Lett.*, 1976, 741-742.

Weisshaar et al., "NMR investigations of the N-linked oligosaccharides at individual glycosylation sites of human lutropin," *Eur. J. Biochem.*, 1991, 195:257-268.

Wright et al., "High level expression of active human alpha-1-antitrypsin in the milk of transgenic sheep," *Biotechnology*, 1991, 9:830-834.

Yoshitake et al., "Nucleotide Sequence of the Gene for Human Factor IX (Antihemophilic factor B)," *Biochemistry*, 1985, 24:3736-3750.

Cera et al., "Water-soluble polysaccharide-anthracycline conjugates: Biological Activity," *Anti-Cancer Drug Design*, 1992, 7(2):143-151.

Gaucher et al., "Stereospecific synthesis and characterization of aminoglycoside ligands from diethylenetriamine," *J. Organic Chem.*, 1999, 64:4012-4015.

Guillaumie et al., "Immobilization of pectin fragments on solid supports: Novel coupling by thiazolidine formation," *Bioconjugate Chem.*, 2002, 13:285-294.

Liu et al., "Characterization of the structural and functional changes of hemoglobin in dimethyl sulfoxide by spectroscopic techniques," *Biochim. Biophys. Acta*, 1998, 138:53-60.

Okamoto et al., "A facile incorporation of the aldehyde function into DNA: 3-formylindole nucleoside as an aldehyde-containing universal nucleoside," *Tetrahedron Lett.*, 2002, 43:4581-4583.

Radomsky and Temeriusz , "Thiazolidine-4(R)-carboxylic acids derived from sugars: part I, C-2-epimerisation in aqueous solutions," *Carb. Res.*, 1989, 187:223-237.

Shao and Tam, "Unprotected peptides as building blocks for the synthesis of peptide dendrimers with oxime, hydrazone and thiazolidine linkages," *J. Am. Chem. Soc.*, 1995, 117(14):3893-3899.

Yang et al., "Functional changes of carboxymethyl potato starch by conjugation with amino acids," *Biosci. Biotechnol. Biochem.*, 1995, 59(12):2203-2206.

Anderson and Meister, "Inhibition of $\gamma$-glutamyl transpeptidase and induction of glutathionuria by $\gamma$-glutamyl amino acids," *Proc. Natl. Acad. Sci. USA*, 1986, 83:5029-5032.

Chaplin and Kennedy (eds.), *Carbohydrate Analysis: a practical approach*, 1994, 2nd Edition, Chapter 1 "Monosaccharides" pp.

(56) References Cited

OTHER PUBLICATIONS 1-41, Chapter 2 "Oligosaccharides" pp. 42-72, Chapter 3 "Neutral Polysaccharides" pp. 73-124, Chapter 5 "Glycoproteins" pp. 181-293, IRL Press.
Dieterich et al., "Hydroxyethyl Starch Antibodies in Humans: Incidence and Clinical Relevance," *Anesth. Analg.*, 1998, 86:1123-1126.
Luo et al., "Controlled DNA delivery systems," *Pharm. Res.*, 1999, 16(8):1300-1308.
*Römpp Chemielexikon*, Thieme Verlag Stuttgart, Germany, 9th edition, 1990, vol. 9, pp. 2281-2285.
Somogyi, "Determination of reducing sugars," *Meth. Carb. Chem.*, 1962, 1:384-386.
Ubeda and Habener, "The large subunit of the DNA replication complex C (DSEB/RF-C140) cleaved and inactivated by caspase-3 (CPP32/YAMA) during Fas-induced apoptosis," *J. Biol. Chem.*, 1997, 272(31):19562-19568.
Cervigni et al., "Synthesis of Glycopeptides and Lipopeptides by Chemoselective Ligation," *Angewandte Chemie International Edition in English*, 1996, 35(11):1230-1232.
Lee and Park, "Conjugation of trypsin by temperature-sensitive polymers containing a carbohydrate moiety: thermal modulation of enzyme activity," *Biotechnol. Prog.*, 1998, 14(3):508-516.
*Dictionary of Chemistry and Chemical Technology*, 2003, p. 769 (English translation provided).
Axèn et al., "Chemical Coupling of Peptides and Proteins to Polysaccharides by Means of Cyanogen Halides," *Nature*, 1967, 214:1302-1304.
Ersdal-Badju et al., "Identification of the Antithrombin III Heparin Binding Site," *J. of Biol. Chem.*, 1997, 272(31):19393-19400.
Gelbrich, "Untersuchungen zur Synthese neuartiger Cellulosematerialien durch topochemische Polymerreaktionen an mikrokristallinen Cellulosen," PhD Dissertation Paper, Vom Fachbereich Gelbrich. "Untersuchungen zur Synthese neuartiger Cellulosematerialien durch topochemische Polymerreaktionen an mikrokristallinen Cellulosen," PhD Dissertation Paper, Vom Fachbereich Chemie, der Technischen Universitat Darmstadt, 1999, 157 pages (English abstract included).
Lonngren et al., "Aldonate Coupling, A Simple Procedure for the Preparation of Carbohydrate-Protein Conjugates for Studies of Carbohydrate-Binding Proteins," *Arch. of BioChem. And BioPhys.*, 1976, 175:661-669.
Orlando, "Modification of proteins and low molecular weight substances with hydroxyethyl starch (HES)," PhD Dissertation Paper, Justus-Liebig Universitat Giessen, 2003, 191 pages.
Chu et al., "Iodine-catalysed Michael addition of mercaptans to α,β-unsaturated ketones under solvent-free conditions," *Tetrahedron Lett*, 2005, 46 (30):4971-4974.
Faith, "Aldehyde-phenol reaction products and derivatives," *J Amer Chem Soc*, 1950, 72(2):837-839.
Iranpoor et al., "Easily prepared azopyridines as potent and recyclable esterification reactions. An efficient modified mitsunobu reaction," *J Org Chem*, 2008, 73(13):4882-4887.
Nakazawa et al., "An efficient synthesis of naphthyl alkyl and aryl sulfides by the reaction of naphthols with alkane- and arenethiols," *Synthesis*, 1989, pp. 955-957.
Caliceti et al., "Immunological properties of unease conjugated to neutral soluble polymers," *Bioconjugate Chern.*, 2001, 12:515-522.
Dorwald, "Side Reactions in Organic Synthesis, A Guide to Successful Synthesis Design," 2005, Wiley-VCH Verlag GmbH & Co., Preface pp. IX-X.
Grieco et al., "Favored Reduction of α-Chlorosilanes vs. α-Chloroalkanes with Tri-n-butyltin Hydride," *J. Org. Chem*, 1978, 43(6):1285.
Heterobifunctional Crosslinkers by Molecular Biosciences, 2000, retrieved on Jun. 6, 2011 from http://web.archive.org/web/20011104182428 / http://www.molbio.com/Heterobi.htm, 13 pages.
"Oxime," in AccessScience, McGraw-Hill Companies, 2008, http://www.accessscience.com, 7 pages.
Pierce Company, "Crosslinking Reagents," 2011, retrieved from http://www.piercenet.com/browse.cfm?fldID=0203, 2 pages.

Reischl (ed.), *Molecular Diagnosis of Infectious Diseases*, 1997, vol. 13, Totowa NJ, Humana Press.Inc. (table of contents only).
Riess, "Oxygen carriers ('blood substitutes')—raison d'etre, chemistry, and some physiology," *Chem. Rev.*, 2001, 101:2797-2919.
Svenson et al., "Oligosaccharide-Protein Conjugate: A Novel Approach for Making Salmonella O-Antigen Immunogens," *FEMS Microbiology Lett.*, 1977, 1: 145-147.
Boyer et al., "Reaction in Biphasic Water/Organic Solvent System in the Presence of Surfactant: Inverse Phase Transfer Catalysis versus Interfacial Catalysis," *Tetrahedron*, 2000, 56:303-307.
Lewis et al., "The phase transfer catalysed synthesis of isoflavone-O-glucosides," *J. Chem. Soc. Perkins Trans. 1*, 1998, pp. 2481-2484.
Lewis and Wähälä, "Regiospecific 4'-O-β-glucosidation of isoflavones," *Tetrahedron Letters*, 1998, 39(51):9559-9562.
Organikum, Organisch-chemisches Grundpraktikum, 1984, VEB Deutscher Verlag der Wissenschaften, p. 472 (with English translation and verification).
Tam et al., "Peptide Synthesis Using Unprotected Peptides Through Orthogonal Coupling Methods," *Proc. Natl. Acad. Sci. USA*, 1995, 92:12485-12489.
Pierce Chemical Technical Library, "cross-linking," 1994, 45 pages.
Carey and Sundberg, "Organische Chemie," VCH Verlagsgesellschaft mbH, Weinheim (DE), 1995, pp. 432-433 and 455 (English translation provided).
Pen et al., "Chemo- and Stereoselective Glycosylation of Hydroxylamino Derivatives: A Versatile Approach to Glycoconjugates," *Tetrahedron*, 1998, 54:12269-12278.
Heindel et al., "Hydrazide Pharmaceuticals as Conjugates to Polyaldehyde Dextran: Syntheses, Characterization, and Stability," *Bioconj. Chem.*, 1990, 1:77-82.
Wilchek and Bayer, "Labeling Glycoconjugates with Hydrazide Reagents," *Meth. Enzymol.*, 1987, 138:429-442.
Anno et al., "Sugar Chemistry," 1995, p. 31 (English translation provided).
Lund et al., "Assessment of methods for covalent binding of nucleic acids to magnetic beads, Dynabeads™, and the characteristics of the bound nucleic acids in hybridization reactions," *Nucl. Acids Res.*, 1988, 16(22):10861-10880.
Wang et al., "Delivery of Antisense Oligonucleotides Using HPMA Polymer: Synthesis of a Thiol Polymer and Its Conjugation to Water-Soluble Molecules," *Bioconj. Chem.*, 1998, 9:749-757.
Cavallaro et al., "Folate-mediated targeting of polymeric conjugates of gemcitabine", International Journal of Pharmaceutics, 307:258-269, (2006).
Grieco et al., "Aryl Selenocyanates and Aryl Thiocyanates: Reagents for the Preparation of Activated Esters," J. Org. Chem. 1978, 43(6):1283-1285.
Harada et al., "Carrier and dose effects on the pharmacokinetics of T-0128, a camptothecin analogue-carboxymethyl dextran conjugate, in non-tumor- and tumor bearing rats ", Journal of controlled release, 71(1):71-86, (2001).
Harada et al., "Determinants for the drug release from T-0128, camptothecin analogue-carboxymethyl dextran conjugate", Journal of controlled release, 69(3):399-412, (2000).
Lee. V.H.L., Ed. Peptide and Protein Drug Delivery, Marcel Dekker, 1991, p. 65.
Pasut et al., "Antitumoral activity of PEG-gemcitabine prodrugs targeted by folic acid", Journal of Controlled Release, 127(3):239-248, (2008).
Peluso et al., "Asparagine surrogates for the assembly of N-linked glycopeptides mimetics by chemoselective ligation" Tetrahedron Letters, 42:2085-2087, (2001).
Rotondaro et al., "Purification and Characterization of Two Recombinant Human Granulocyte Colony-Stimulating Factor Glycoforms", Molecular Biotechnology, 11:117-128, (1999).
Seymour et al., "A phase I study of BAY 38/3441 given as a short infusion daily for five days every 3 weeks. A National Cancer Institute of Canada Clinical Trials Group Study", European Journal of Cancer, 37(1):73, (2001).
Svenson and Lindberg, Journal of Immunological Methods, 25 (1979), 323-335.
Svenson, Journal of Immunology, vol. 120, No. 5 (1978), 1750-1757.

(56) References Cited

OTHER PUBLICATIONS

Zhang, L. et al. "Thiazolidine formation as a general and site-specific conjugation method . . . " Anal. Biochem.. 233:87-93, (1996).

Blackburn and Gait (Eds), "DNA and RNA Structure," in Nucleic Acids in Chemistry and Biology, 2nd Edition, 1996, Oxford University Press, pp. 15-81.

Englisch and Gauss, "Chemically modified oligonucleotides as probes and inhibitors," *Angew. Chem. Int. Ed. Engl.*,1991, 30:613-629.

Ng et al., "Pegaptanib, a targeted anti-VEGF aptamer for ocular vascular disease," *Nature Reviews*, 2005, 5:123-126

Nielsen et al., "Sequence-selective recognition of DNA by strand displacement with a thymidine-substituted polyamide," *Science*, 1991, 254:1497-1500.

Pieve et al., "Modification of thiol functionalized aptamers by conjugation of synthetic polymers," *Bioconjugate Chemistry*, 2012, 21:169-174.

Alagon et al., "Activation of Polysaccharides with 2-Iminothiolane and its Uses", Biochem. 19:4341-4345 (1980).

Balazy et al., "S-Nitroglutathione, a Product of the Reaction between Peroxynitrite and Glutathione That Generates Nitric Oxide", J. Biol. Chem. 273(48):32009-32015 (1998).

Etrych et al., "New HPMA Copolymers containing doxorubicin bound via pH-sensitive linkage: synthesis and preliminary in vitro and in vivo biological properties", Journal of Controlled Release 73:89-102 (2001).

European Pharmacopoeia, Supplemental 2001, "Haemodialysis Solutions" pp. 911-918.

Ganson et al., "Control of Hyperuricemia in Subjects with refractory gout, and induction of antibody against poly (ethylene glycol) (PEG), in a phase I trial of subcutaneous PEGylated urate oxidase", Arthritis Research & Therapy, 8: R12 (2005).

Glederblom et al., "Cremophor EL: the drawbacks and advantages of vehicle selection for drug formulation", European Journal of Cancer, 37:1590-1598 (2001).

Gerwech et al., "Tumor pH controls the in vivo efficacy of weak acid and base chemotherapeutics", Mol. Cancer Ther. 5(5):1275-1279 (2006).

Greenwald et al., "Drug Delivery Systems: Water Soluble Taxol 2'-Poly(ethylene glycol) Ester Prodrugs—Design and in Vivo Effectiveness" J. Med. Chem., 39:424-431 (1996).

Hamilton et al., "Characterization of a Human Ovarian Carcinoma Cell Line (NIH:OVCAR-3) with Androgen and Estrogen Receptors", Cancer Research, 43:5379-5389 (1983).

Jungheinrich et al., "Pharmacokinetics of Hydroxyethyl Starch", Clin Pharmacokinet, 44(7):681-699 (2005).

Katsumi et al., "Development of Polyethylene Glycol-Conjugated Poly-S-Nitrosated Serum Albumin, a Novel S-Nitrosothiol for Prolonged Delivery of Nitric Oxide in the Blood Circulation in Vivo", Journal of Pharmacology and Experimental Therapeutics, 314(3):1117-1124 (2005).

Kinstler et al., "Characterization and Stability of N-terminally PEGylated rhG-CSF", Pharmaceutical Research, 13(7):996-1002 (1996).

Kulicke et al., "Measurements of the Refractive Index Increment on Hydroxyethyl Starch as a Basis for Absolute Molecutlar Weight Determinations", Starch, 43(10):392-396 (1991).

Laine et al., "Polyethylene Glycol Nephrotoxicity secondary to prolonged High-Dose Intravenous Lorazepam", Annals of Pharmacotherapy, 29:1110-1114 (1995).

Bernardes et al., "The Direct Formation of Glycosyl Thiols from Reducing Sugars Allows One-Pot Protein Glycoconjugation", Angew. Chem. 118:4111-4115 (2006).

Besheer et al., "Enzymatically Catalyzed HES Conjugation Using Microbial Transglutaminase:Proof of Feasibility", Journal of Pharmaceutical Sciences, 98(11):4420-4428 (2009).

Lee et al., "Functional Polymers for Layer-by-Layer Construction of Multilayer via Chemoselective Immobilization", Macromolecules, 37:1849-1856, (2004).

Lieber et al., "A Continuous Tumor-Cell Line From a Human Lung Carcinoma with Properties of Type II Alveolar Epithelial Cells", Int. J. Cancer, 17:62-70, (1976).

Lipke et al., "Localized Delivery of Nitric Oxide from Hydrogels Inhibits Neointima Formation in Rat Cartoid Ballon Injury Model", Acta Biomaterialia, 1:597-606, (2005).

Megson et al., "Inhibition of Human Platelet Aggregation by a Novel S-Nitrosothiol is Abolished by Haemoglobin and Red Blood Cell in vitro: Implications for Anti-Thrombotic Therapy", British Journal of Pharmacology, 131:1391-1398, (2000).

Nathan et al., "Strategies for Covalent Attachment of Doxorubicin to Poly(PEG-Lys), a New Water Soluble Poly(ether urethane)", Journal of Bioactive and Compatible Polymers, 9:239-251 (1994).

Naundorf et al., "Characterization of two human mammary carcinomas, MT-1 and MT-3, suitable for in vivo testing of either lipids and their dirivatives", Breast Cancer Research and Treatment, 23:87-95, (1992).

Ph. Eur. Nachtrag, "Erythropoietini solutio concentrata", pp. 780, (2000).

Ph. Eur. Nachtrag, "Erythropoietini solutio concentrata", pp. 911, (2001).

Pharmeuropa, "erythropoietin Concentrated Solution", 8(3):371. (1996).

Thermo Scientific Pierce "Crosslinking Technical Handbook", 48pgs. (2009).

Reynolds et al., "S-nitrosohemoglobin deficiency: A mechanism for loss of physiological activity in banked blood", PNAS, 104(43):17058-17062, (2007).

Rodrigues et al., "Correlation of the acid-sensitivity of polyethylene glycol daunorubicin conjugates with their in vitro antiproliferative activity", Bioorganic & Medicinal Chemistry, 14:4110-4117, (2006).

Salo et al., "Aminooxy Functionalized Oligonucleotides: Preparation, On-Support Derivatization, and Postsynthetic Attachment to Polymer Support", Bioconjugate Chem., 10:815-823, (1999).

Schneerson et al., "Preparation, characterization and immunogenicity of haemophilus influenzae type b polysaccharide-protein conjugates", Journal of Experimental Medicine, 152:361-376 (1980).

Skopp et al., "Fingerprinting of proteins cleaved in solution by cyanogen bromide", Appl. and Theoret. Electrophoresis, 1:61-64, (1989).

Skwarczynski et al., "Paclitaxel Prodrugs Toward Smarter Delivery of Anticancer Agents", Journal of Medicinal Chemistry, 49(25):7253-7269, (2006).

Stien et al., "Development and characterisation of novel human multidrug resistant mammary carcinoma lines in vitro and in vivo", Int. J. Cancer, 72:885-891, (1997).

Tomasik et al., "Chemical Modification of Starch", Advaces in Carbohydrate Chemistry and Biochemistry, 59:179-403, (2004).

Velasco et al., "Synthetic Peptides Representing T-Cell Epitopes Act as Carriers in Pneumococcal Polysaccharide Conjugate Vaccines", Infection and Immunity, 63(3):961-968, (1995).

Vasey et al., :Phase I Clinical and Pharmacokinetic Study of PKI [N-(2-Hydroxypropyl)methacrylamide Copolymer Doxorubicin]: First Member of a New Class of Chemotherapeutic Agents-Drug-Polymer Conjugates, Clinial Cancer Research, 5:83-94, (1999).

Waltzinger et al., "Pharmacokinetics and Tolerability of a New Hydroxyethyl Starch (HES) Specification [HES (130/0.4)] after Single-Dose Infusion of 6% or 10% Solutions in Healthy Volunteers", Pharmacokinetics, 16(2):151-160, (1998).

Wong, Chemical Dictionary Entry Concerning Carbohydrates, *Chemistry of Protein Conjugation and Cross-Linking*, 1993, CRCS, Inc., 6 pages including English-language Abstract.

Frie, "Evaluating a Novel Method for Coupling of Low Molecular Hydroxyethylstarch with Model Compounds and Application of this Method to further Selected Proteins," Diploma Thesis dated Feb. 2, 1998, Diplomarbeit, Fachhochschule, Hamburg, Germany, 82 pages including English-language Abstract.

Schmoll et al. (eds.), "Summary of Basics of Oncology and Current Therapeutic Approaches," *Compendium for Internistic Oncology*, 1996, Table of Contents with English Summary.

(56) References Cited

OTHER PUBLICATIONS

Sommermeyer et al., "Hydroxyethylstarch for Clinical Application: Physical and Chemical Characterisation," *Krankenhauspharmazie*, 1987, 8:271-278.

Klimek et al., "Specific Immunotherapy (Hyposensibilisation)," *Allergologie and Umweltmedizin*, Chapter 15, pp. 157-195, 1997.

Staab, "New Methods in Preparatory Organic Chemistry IV. Synthesis using heterocyclic amides (azolides)," *Angew. Chem.*, 1962, 74(12):407-422.

Stille et al., "Atherosclerosis as Consequence of Chronic Infection by *Chlamydia pneumoniae*," *Herz*, 1998, 23:185-192 (w/English summary).

* cited by examiner 1    2    3    4    Mw Std

A   B   C

EPO GT-1 no acid treatment.;
+ mild periodate ox

EPO GT-1 5 min H$^+$ and mild periodate ox

EPO GT-1 10 min H$^+$ and mild periodate ox

EPO GT-1 no acid and no periodate treatment

Samples before and after digestion with N-glycosidase

HASYLATED POLYPEPTIDES

This application is a continuation-in-part and claims benefit under 35 U.S.C. §120 of International Application No. PCT/EP03/08858 having an International Filing Date of Aug. 8, 2003, which published in English as International Publication Number WO 2004/024761, and which claims the benefit of priority of European Patent Application No. 02020425.1, having a filing date of Sep. 11, 2002, and U.S. Provisional Application Ser. No. 60/409,781 having a filing date of Sep. 11, 2002.

The present invention relates to polypeptides, especially erythropoietin conjugated to hydroxyalkylstarch (HAS), especially to hydroxyethylstarch.

The application of polypeptides, especially enzymes or cytokines, to the circulatory system in order to obtain a particular physiological effect is a well-known tool in modern medicine.

Erythropoietin (EPO) is a glycoprotein hormone necessary for the maturation of erythroid progenitor cells into erythrocytes. In human adults, it is produced in the kidney. EPO is essential in regulating the level of red blood cells in the circulation. Conditions marked by low levels of tissue oxygen provoke an increased biosynthesis of EPO, which in turn stimulates erythropoiesis. A loss of kidney function as it is seen in chronic renal failure, for example, typically results in decreased biosynthesis of EPO and a concomitant reduction in red blood cells.

Erythropoietin is an acid glycoprotein hormone of approximately 34,000 Da. Human erythropoietin is a 166 amino acid polypeptide that exists naturally as a monomer (Lin et al., 1985, PNAS 82, 7580-7584, EP 148 605 B2, EP 411 678 B2). The identification, cloning and expression of genes encoding erythropoietin are described, e.g., in U.S. Pat. No. 4,703,008. The purification of recombinant erythropoietin from cell culture medium that supported the growth of mammalian cells containing recombinant erythropoietin plasmids, for example, is described in U.S. Pat. No. 4,667,016.

It is generally believed in this technical field that the biological activity of EPO in vivo mainly depends on the degree of sialic acids bound to EPO (see e.g. EP 428 267 B1). Theoretically, 14 molecules of sialic acid can be bound to one molecule EPO at the terminal ends of the carbohydrate side chains linked to N- and O-glycosylation sites. Highly sophisticated purification steps are necessary to obtain highly sialylated EPO preparations.

For further detailed information on erythropoietin see Krantz, Erythropoietin, 1991, Blood, 77(3):419-34 (Review) and Cerami, Beyond erythropoiesis: novel applications for recombinant human erythropoietin, 2001, Semin Hematol., (3 Suppl 7):33-9 (Review).

A well-known problem with the application of polypeptides and enzymes is that these proteins often exhibit an unsatisfactory stability. Especially, erythropoietin has a relatively short plasma half live (Spivak and Hogans, 1989, Blood 73, 90; McMahon et al., 1990, Blood 76, 1718). This means that therapeutic plasma levels are rapidly lost and repeated intravenous administrations must be carried out. Furthermore, in certain circumstances an immune response against the peptides is observed.

It is generally accepted that the stability of polypeptides can be improved and the immune response against these polypeptides is reduced when the polypeptides are coupled to polymeric molecules. WO 94/28024 discloses that physiologically active polypeptides modified with polyethyleneglycol (PEG) exhibit reduced immunogenicity and antigenicity and circulate in the bloodstream considerably longer than unconjugated proteins, i.e. have a longer clearance rate.

However, PEG-drug conjugates exhibit several disadvantages, e.g. they do not exhibit a natural structure which can be recognized by elements of in vivo degradation pathways. Therefore, apart from PEG-conjugates, other conjugates and protein polymerates have been produced. A plurality of methods for the cross-linking of different proteins and macromolecules such as polymerase have been described in the literature (see e.g. Wong, Chemistry of protein conjugation and cross-linking, 1993, CRCS, Inc.).

Hydroxyethylstarch (HES) is a derivative of naturally occurring amylopektine and is degraded by α-Amylase in the body. The preparation of HES-protein-conjugates is described in the state of the art (see, e.g., HES-hemoglobin-conjugates in DE 26 16 086 or DE 26 46 854).

DE 26 46 854 discloses methods for the conjugation of hemoglobin to HES. In these methods, HES is reacted with sodiumperiodate, which results in the production of dialdehydes which are linked to hemoglobin. In contrast to this, DE 26 16 086 discloses the conjugation of hemoglobin to HES according to a procedure wherein first a cross-linking agent (e.g. bromocyane) is bound to HES and subsequently hemoglobin is linked to the intermediate product.

HES is a substituted derivative of the carbohydrate polymer amylopektine, which is present in corn starch at a concentration of up to 95% per weight. HES exhibits advantageous biological properties and is used as a blood volume replacement agent and in hemodilution therapy in the clinics (Sommermeyer et al., 1987, Krankenhauspharmazie, 8(8), 271-278; and Weidler et al., 1991, Arzneim.-Forschung/Drug Res., 41, 494-498).

Amylopektine consists of glucose moieties, wherein in the main chain α-1,4-glycosidic bonds are present and at the branching sites α-1,6-glycosidic bonds are found. The physical-chemical properties of this molecule are mainly determined by the type of glycosidic bonds. Due to the nicked α-1,4-glycosidic bond, helical structures with about six glucose-monomers per turn are produced.

The physical-chemical as well as the biochemical properties of the polymer can be modified via substitution. The introduction of a hydroxyethyl group can be achieved via alkaline hydroxyethylation. By adapting the reaction conditions it is possible to exploit the different reactivity of the respective hydroxy group in the unsubstituted glucose monomer with respect to a hydroxyethylation. Owing to this fact, the skilled person is able to influence the substitution pattern to a limited extent.

Consequently, HES is mainly characterized by the molecular weight distribution and the degree of substitution. There are two possibilities of describing the substitution degree:

1. The substitution degree can be described relative to the portion of substituted glucose monomers with respect to all glucose moieties (DS).
2. The substitution degree can be described as the "molar substitution" (MS), wherein the number of hydroxyethyl groups per glucose moiety are described.

HES solutions are present as polydisperse compositions, wherein each molecule differs from the other with respect to the polymerisation degree, the number and pattern of branching sites and the substitution pattern. HES is therefore a mixture of compounds with different molecular weight. Consequently, a particular HES solution is determined by average molecular weight with the help of statistical means. In this context, $M_n$ is calculated as the arithmetic mean depending on the number of molecules. Alternatively, $M_w$, the weight mean, represents a unit which depends on the mass of the HES.

The HES-drug conjugates disclosed in the art suffer from the disadvantage that HES is not conjugated site-specifically to the drug. Consequently, the conjugation results in a very heterogenous product having many components that may be inactive due to the destruction of the 3-dimensional structure during the conjugation step.

In summary, there is still a need for further improved polypeptides with improved stability and/or bioactivity. This applies especially to erythropoietin where isoforms with a high degree of sialic acids and therefore high activity have to be purified from isoforms with a low degree of sialic acids (see EP 428 267 B1). Therefore, it would be highly advantageous if production methods were available which provide highly active polypeptides without requiring extensive purification. Unfortunately, the production of polypeptides in bacteria or insect cells is often difficult, because the polypeptides are often not produced in a properly folded, native confirmation and lack proper glycosylation.

Consequently, it is an object of the present invention to provide polypeptide derivatives, especially erythropoietin derivatives, having a high biological activity in vivo which can be easily produced and at reduced costs. Furthermore, it is a further object of the present invention to provide a method for the production of polypeptide derivatives which is easy to perform and yields in products with high biological activity. It is a further object of the invention to provide pharmaceutical compositions comprising polypeptide derivatives with high biological activity.

According to one aspect of the present invention, the problem is solved by a hydroxyalkylstarch (HAS)-erythropoietin (EPO)-conjugate (HAS-EPO) comprising one or more HAS molecules, wherein each HAS is conjugated to the EPO via a) a carbohydrate moiety; or b) a thioether.

The HAS-EPO of the invention has the advantage that it exhibits an improved biological stability when compared to the erythropoietin before conjugation. Furthermore, it exhibits a higher biological activity than standard BRP EPO. This is mainly due to the fact that HAS-EPO is less or even not recognized by the removal systems of the liver and kidney and therefore persists in the circulatory system for a longer period of time. Furthermore, since the HAS is attached site-specifically, the risk of destroying the in vivo biological activity of EPO by conjugation of HAS to EPO is minimized.

The HAS-EPO of the invention has mainly two components, namely the erythropoietin (EPO)-polypeptide and the hydroxyalkylstarch (HAS) linked thereto.

The EPO can be of any human (see e.g. Inoue, Wada, Takeuchi, 1994, An improved method for the purification of human erythropoietin with high in vivo activity from the urine of anemic patients, Biol Pharm Bull. 17(2), 180-4; Miyake, Kung, Goldwasser, 1977, Purification of human erythropoietin., J Biol. Chem., 252(15), 5558-64) or another mammalian source and can be obtained by purification from naturally occurring sources like human kidney, embryonic human liver or animal, preferably monkey kidney. Furthermore, the expression "erythropoietin" or "EPO" encompasses also an EPO variant wherein one or more amino acids (e.g. 1 to 25, preferably 1 to 10, more preferred 1 to 5, most preferred 1 or 2) have been exchanged by another amino acid and which exhibits erythropoietic activity (see e.g. EP 640 619 B1). The measurement of erythropoietic activity is described in the art (for measurement of activity in vitro see e.g. Fibi et al., 1991, Blood, 77, 1203 ff; Kitamura et al, 1989, J. Cell Phys., 140, 323-334; for measurement of EPO activity in vivo see Ph. Eur. 2001, 911-917; Ph. Eur. 2000, 1316 Erythropoietini solutio concentrata, 780-785; European Pharmacopoeia (1996/2000); European Pharmacopoeia, 1996, Erythropoietin concentrated solution, Pharmaeuropa., 8, 371-377; Fibi, Hermentin, Pauly, Lauffer, Zettlmeissl., 1995, N- and O-glycosylation muteins of recombinant human erythropoietin secreted from BHK-21 cells, Blood, 85(5), 1229-36; (EPO and modified EPO forms were injected into female NMRI mice (equal amounts of protein 50 ng/mouse) at day 1, 2 and 3 blood samples were taken at day 4 and reticulocytes were determined)). Further publications where tests for the measurement of the activity of EPO are Barbone, Aparicio, Anderson, Natarajan, Ritchie, 1994, Reticulocytes measurements as a bioassay for erythropoietin, J. Pharm. Biomed. Anal., 12(4), 515-22; Bowen, Culligan, Beguin, Kendall, Villis, 1994, Estimation of effective and total erythropoiesis in myelodysplasia using serum transferrin receptor and erythropoietin concentrations, with automated reticulocyte parameters, Leukemi, 8(1), 151-5; Delorme, Lorenzini, Giffin, Martin, Jacobsen, Boone, Elliott, 1992, Role of glycosylation on the secretion and biological activity of erythropoietin, Biochemistry, 31(41), 9871-6; Higuchi, Oh-eda, Kuboniwa, Tomonoh, Shimonaka, Ochi, 1992; Role of sugar chains in the expression of the biological activity of human erythropoietin, J. Biol. Chem., 267(11), 7703-9; Yamaguchi, Akai, Kawanishi, Ueda, Masuda, Sasaki, 1991, Effects of site-directed removal of N-glycosylation sites in human erythropoietin on its production and biological properties, J. Biol. Chem., 266(30), 20434-9; Takeuchi, Inoue, Strickland, Kubota, Wada, Shimizu, Hoshi, Kozutsumi, Takasaki, Kobata, 1989, Relationship between sugar chain structure and biological activity of recombinant human erythropoietin produced in Chinese hamster ovary cells, Proc. Natl. Acad. Sci. USA, 85(20), 7819-22; Kurtz, Eckardt, 1989, Assay methods for erythropoietin, Nephron., 51(1), 114 (German); Zucali, Sulkowski, 1985, Purification of human urinary erythropoietin on controlled-pore glass and silicic acid, Exp. Hematol., 13(3), 833-7; Krystal, 1983, Physical and biological characterization of erythroblast enhancing factor (EEF), a late acting erythropoetic stimulator in serum distinct from erythropoietin, Exp. Hematol., 11(1), 18-31.

Preferably, the EPO is recombinantly produced. This includes the production in eukaryotic or prokaryotic cells, preferably mammalian, insect, yeast, bacterial cells or in any other cell type which is convenient for the recombinant production of EPO. Furthermore, the EPO may be expressed in transgenic animals (e.g. in body fluids like milk, blood, etc.), in eggs of transgenic birds, especially poultry, preferred chicken, or in transgenic plants.

The recombinant production of a polypeptide is known in the art. In general, this includes the transfection of host cells with an appropriate expression vector, the cultivation of the host cells under conditions which enable the production of the polypeptide and the purification of the polypeptide from the host cells. For detailed information see e.g. Krystal, Pankratz, Farber, Smart, 1986, Purification of human erythropoietin to homogeneity by a rapid five-step procedure, Blood, 67(1), 71-9; Quelle, Caslake, Burkert, Wojchowski, 1989, High-level expression and purification of a recombinant human erythropoietin produced using a baculovirus vector, Blood, 74(2), 652-7; EP 640 619 B1 and EP 668 351 B1.

In a preferred embodiment, the EPO has the amino acid sequence of human EPO (see EP 148 605 B2).

The EPO may comprise one or more carbohydrate side chains (preferably 14, preferably 4) attached to the EPO via N- and/or O-linked glycosylation, i.e. the EPO is glycosylated. Usually, when EPO is produced in eukaryotic cells, the polypeptide is posttranslationally glycosylated. Consequently, the carbohydrate side chains may have been attached to the EPO during biosynthesis in mammalian, especially human, insect or yeast cells. The structure and properties of glycosylated EPO have been extensively studied in the art (see EP 428 267 B1; EP 640 619 B1; Rush, Derby, Smith, Merry, Rogers, Rohde, Katta, 1995, Microheterogeneity of erythropoietin carbohydrate structure, Anal Chem., 67(8), 1442-52; Takeuchi, Kobata, 1991, Structures and functional roles of the sugar chains of human erythropoietins, Glycobiology, 1(4), 337-46 (Review).

The HAS may be directly conjugated to the EPO or, alternatively, via a linker molecule. The nature of the linker molecule depends on the way how the HAS is linked to the EPO. Possible functional groups of linkers are described in Table 1 and below. Several linkers are commercially available (e.g. from Pierce, available from Perbio Science Deutschland GmbH, Bonn, Germany)). Some suitable linkers are described in Table 2. The nature of the linker and its purpose are described in detail below in the section concerning the method for the production of HES-EPO.

According to a preferred embodiment of the HAS-EPO conjugate of the invention, the HAS is conjugated to the EPO via a carbohydrate moiety.

In the context of the present invention, the term "carbohydrate moiety" refers to hydroxyaldehydes or hydroxyketones as well as to chemical modifications thereof (see Römpp Chemielexikon, Thieme Verlag Stuttgart, Germany, 9$^{th}$ edition 1990, Volume 9, pages 2281-2285 and the literature cited therein). Furthermore, it also refers to derivatives of naturally occuring carbohydrate moieties like glucose, galactose, mannose, sialic acid and the like. The term also includes chemically oxidized naturally occuring carbohydrate moieties wherein the ring structure has been opened.

The carbohydrate moiety may be linked directly to the EPO polypeptide backbone. Preferably, the carbohydrate moiety is part of a carbohydrate side chain. In this case, further carbohydrate moieties may be present between the carbohydrate moiety to which HAS is linked and the EPO polypeptide backbone. More preferably, the carbohydrate moiety is the terminal moiety of the carbohydrate side chain.

In a more preferred embodiment, the HAS is conjugated to a galactose residue of the carbohydrate side chains, preferably the terminal galactose residue of the carbohydrate side chain. This galactose residue can be made available for conjugation by removal of terminal sialic acids, followed by oxidation (see below).

In a further more preferred embodiment, the HAS is conjugated to a sialic acid residue of the carbohydrate side chains, preferably the terminal sialic acid residue of the carbohydrate side chain.

Furthermore, the HAS may be conjugated to the EPO via a thioether. As explained in detail below, the S atom can be derived from any SH group attached to the EPO, both naturally or non naturally occurring.

In a preferred embodiment, the S atom may be derived from a SH group which has been introduced in an oxidized carbohydrate moiety of HES, preferably an oxidized carbohydrate moiety which is part of a carbohydrate side chain of EPO (see below).

Preferably, the S atom in the thioether is derived from a naturally-occurring cysteine or from an added cysteine. More preferably, the EPO has the amino acid sequence of human EPO and the naturally occurring cysteines are cysteine 29 and/or 33. In a more preferred embodiment, HAS is conjugated to cysteine 29 and cysteine 33 is replaced by another amino acid. Alternatively, HAS may be conjugated to cysteine 33 and cysteine 29 is replaced by another amino acid.

In the context of the present invention, by the term "added cysteines" it is meant that the polypeptides, preferably EPO, comprise a cysteine residue which is not present in the wild-type polypeptide.

In the context of this aspect of the invention, the cysteine may be an additional amino acid added at the N- or C-terminal end of EPO.

Furthermore, the added cysteine may have been added by replacing a naturally occuring amino acid by a cysteine. Suitable methods are known in the art (see above). Preferably, in the context of this aspect of the invention, the EPO is human EPO and the replaced amino acid residue is serine 126.

The second component of the HAS-EPO is hydroxyalkylstarch (HAS).

In the context of the present invention, the term "hydroxyalkylstarch" is used to indicate starch derivatives which have been substituted by hydroxyalkylgroups. In this context, the alkyl group may be substituted. Preferably, the hydroxyalkyl contains 2-10 carbon atoms, more preferably 24 carbon atoms. "Hydroxyalkylstarch" therefore preferably comprises hydroxyethylstarch, hydroxypropylstarch and hydroxybutylstarch, wherein hydroxyethylstarch and hydroxypropylstarch are preferred.

The hydroxyalkylgroup(s) of HAS contain at least one OH-group.

The expression "hydroxyalkylstarch" also includes derivatives wherein the alkyl group is mono- or polysubstituted. In this context, it is preferred that the alkyl group is substituted with an halogen, especially flourine, or with an aryl group, provided that the HAS remains water soluble. Furthermore, the terminal hydroxy group of hydroxyalkyl may be esterified or etherified. In addition, the alkyl group of the hydroxyalkylstarch may be linear or branched.

Furthermore, instead of alkyl, also linear or branched substituted or unsubstituted alkene groups may be used.

Hydroxyethylstarch (HES) is most preferred for all embodiments of the present invention.

In the context of the present invention, hydroxyethylstarch may have a mean molecular weight (weight mean) of 1-300 kDa, wherein a mean molecular weight of 5-100 kDa is more preferred. Hydroxyethylstarch can further exhibit a molar degree of substitution of 0.1 to 0.8 and a ratio between $C_2$:$C_6$-substitution in the range of 2-20, with respect to the hydroxyethylgroups.

The HAS-EPO may comprise 1-12, preferably 1-9, 1-6 or 1-3, most preferred 1-4 HAS molecules per EPO molecule. The number of HAS-molecules per EPO molecule can be determined by quantitative carbohydrate compositional analysis using GC-MS after hydrolysis of the product and derivatisation of the resulting monosaccharides (see Chaplin and Kennedy (eds.), 1986, Carbohydrate Analysis: a practical approach, IRL Press Practical approach series (ISBN 0-947946-44-3), especially Chapter 1, Monosaccharides, page 1-36; Chapter 2, Oligosaccharides, page 37-53, Chapter 3, Neutral Polysaccharides, page 55-96).

The HAS-EPO conjugate of the invention may exhibit essentially the same in-vitro biological activity as recombinant native EPO, since the in-vitro biological activity only measures binding affinity to the EPO receptor. Methods for determining the in-vitro biological activity are known in the art (see above).

Furthermore, the HAS-EPO exibits a greater in vivo activity than the EPO used as a starting material for conjugation (unconjugated EPO). Methods for determining the in vivo biological activity are known in the art (see above). Furthermore, assays for the determination of in vivo and in vitro EPO activity are given in Examples 9 and 10.

The HAS-EPO conjugate may exhibit an in vivo activity of 110 to 500%, preferably 300 to 400%, or 110% to 300%, preferably 110% to 200%, more preferred 110% to 180% or 110 to 150%, most preferred 110% to 140%, if the in vivo activity of the unconjugated EPO is set as 100%.

Compared to the highly sialylated EPO of Amgen (see EP 428 267 B1), the HAS-EPO exibits preferably at least 50%, more preferred at least 70%, even more preferred at least 85% or at least 95%, at least 150%, at least 200% or at least 300% of the in vivo activity of the highly sialylated EPO, if the in vivo activity of highly sialylated EPO is set as 100%. Most preferred, it exhibits at least 95% of the in vivo activity of the highly sialylated EPO.

The high in vivo biological activity of the HAS-EPO conjugate of the invention mainly results from the fact that the HAS-EPO conjugate remains longer in the circulation than the unconjugated EPO, because it is less recognized by the removal systems of the liver and because renal clearance is reduced due to the higher molecular weight. Methods for the determination of the in vivo half life time of EPO in the circulation are known in the art (Sytkowski, Lunn, Davis, Feldman, Siekman, 1998, Human erythropoietin dimers with markedly enhanced in vivo activity, Proc. Natl. Acad. Sci. USA, 95(3), 1184-8).

Consequently, it is a great advantage of the present invention that a HAS-EPO is provided that may be administered less frequently than the EPO preparations commercially available at present. While standard EPO preparations have to be administered at least all 3 days, the HAS-EPO conjugate of the invention is preferable adminstered twice a week, more preferably once a week.

All embodiments disclosed below with respect of the method of the invention to produce a HAS-EPO concerning properties of EPO or HAS apply also to the HAS-EPO conjugate of the invention.

Hydroxyalkylstarch is an ether derivative of starch. Besides of said ether derivatives, also other starch derivatives can be used in the context of the present invention. For example, derivatives are useful which comprise esterified hydroxy groups. These derivatives may be e.g. derivatives of unsubstituted mono- or dicarboxylic acids with 2-12 carbon atoms or of substituted derivatives thereof. Especially useful are derivatives of unsubstituted monocarboxylic acids with 2-6 carbon atoms, especially of acetic acid, In this context, acetylstarch, butylstarch or propylstarch are preferred.

Furthermore, derivatives of unsubstituted dicarboxylic acids with 2-6 carbon atoms are preferred.

In the case of derivatives of dicarboxylic acids, it is useful that the second carboxy group of the dicarboxylic acid is also esterified. Furthermore, derivatives of monoalkyl esters of dicarboxylic acids are also suitable in the context of the present invention.

For the substituted mono- or dicarboxylic acids, the substitute groups may be preferably the same as mentioned above for substituted alkyl residues.

Techniques for the esterification of starch are known in the art (see e.g. Klemm D. et al, Comprehensive Cellulose Chemistry Vol. 2, 1998, Whiley-VCH, Weinheim, N.Y., especially chapter 4.4, Esterification of Cellulose (ISBN 3-527-29489-9).

In a further aspect, the present invention relates to a method for the production of a hydroxyalkylstarch (HAS)-erythropoietin (EPO)-conjugate (HAS-EPO), comprising the steps of:
a) providing EPO being capable of reacting with modified HAS,
b) providing modified HAS being capable of reacting with the EPO of step a), and
c) reacting the EPO of step a) with the HAS of step b), whereby an HAS-EPO is produced comprising one or more HAS molecules, wherein each HAS is conjugated to the EPO via
   i) a carbohydrate moiety; or
   ii) a thioether.

The method of the invention has the advantage that a HAS-EPO conjugate is produced which exhibits a high biological activity. Furthermore, the method of the invention has the advantage that an effective EPO derivative can be produced at reduced costs since the method does not comprise extensive and time consuming purification steps resulting in low final yield, e.g. it is not necessary to purify away undersialylated EPO forms which are known to exhibit low or no in-vivo biological activity. Especially Example 20 demonstrates that a HES-EPO produced with few modifications steps exhibits a 3-fold activity over standard BRP EPO.

Accordingly, in the first step of the method of the invention, an EPO is provided which is capable of reacting with modified HAS.

As used in the present invention, the term "providing" has to be interpreted in the way that after the respective step a molecule (in step a) EPO, in step b) HAS) with the desired properties is available.

In the case of step a), this includes the purification of EPO from natural sources as well as the recombinant production in host cells or organisms, and, if necessary, the modification of the EPO so obtained.

With respect to the EPO being the starting material of the present invention, the same applies as for the erythropoietin being part of the HAS-EPO conjugate of the invention. In this context, the preferred embodiments disclosed above apply also for the method of the invention.

Consequently, in a preferred embodiment, the EPO has the amino acid sequence of human EPO.

Preferably, the EPO is recombinantly produced. This includes the production in eukaryotic or prokaryotic cells, preferably mammalian, insect, yeast, bacterial cells or in any other cell type which is convenient for the recombinant production of EPO. Furthermore, the EPO may be expressed in transgenic animals (e.g. in body fluids like milk, blood, etc.), in eggs of transgenic birds, especially poultry, preferred chicken, or in transgenic plants.

The recombinant production of a polypeptide is known in the art. In general, this includes the transfection of host cells with an appropriate expression vector, the cultivation of the host cells under conditions which enable the production of the polypeptide and the purification of the polypeptide from the host cells (Krystal, Pankratz, Farber, Smart, 1986, Purification of human erythropoietin to homogeneity by a rapid five-step procedure, Blood, 67(1), 71-9; Quelle, Caslake, Burkert, Wojchowski, 1989, High-level expression and purification of a recombinant human erythropoietin produced using a baculovirus vector, Blood, 74(2), 652-7; EP 640 619 B1 and EP 668 351 B1).

The EPO may comprise one or more carbohydrate side chains attached to the EPO via N- and/or O-linked glycosylation, i.e. the EPO is glycosylated. Usually, when EPO is produced in eukaryotic cells, the polypeptide is posttranslationally glycosylated. Consequently, the carbohydrate side chains may have been attached to the EPO during production in mammalian, especially human, insect or yeast cells, which may be cells of a transgenic animal (see above), either extracted from the animal or still in the animal.

These carbohydrate side chains may have been chemically or enzymatically modified after the expression in the appropriate cells, e.g. by removing or adding one or more carbohydrate moieties (see e.g. Dittmar, Conradt, Hauser, Hofer, Lindenmaier, 1989, Advances in Protein design; Bloecker, Collins, Schmidt, and Schomburg eds., GBF-Monographs, 12, 231-246, VCH Publishers, Weinheim, N.Y., Cambridge)

It is the object of the method of the invention to provide an HAS-EPO comprising one or more HAS molecules where the HAS is conjugated to the EPO via a carbohydrate moiety (i) or via a thioether (ii). Consequently, the EPO provided in step a) should have the properties that a conjugation via a carbohydrate moiety and/or via a thioether is possible. Therefore the EPO after step a) may preferably contain either (1) at least one reactive group linked, either directly or via a linker molecule, to sulfide groups or carbohydrate moieties, which is capable to react with HES or modified HES,
(2) at least one carbohydrate moiety to which modified HAS can be conjugated, and/or
(3) at least one free SH-group.

With respect to possibility (1) above, the EPO of step a) is preferably obtainable by conjugating an appropriate linker molecule to the SH-group(s) or carbohydrate moieties of EPO. An example for such a modified EPO is provided in Example 4, 2.1. It is important to ensure that the addition of the linker molecule does not damage the EPO. However, this is known to the person skilled in the art.

With respect to possibility (2) above, in a preferred embodiment, the modified HAS is conjugated to the EPO via a carbohydrate moiety.

The carbohydrate moiety may be linked directly to the EPO polypeptide backbone. Preferably, the carbohydrate moiety is part of a carbohydrate side chain. In this case, further carbohydrate moieties may be present between the carbohydrate moiety to which HAS is linked and the EPO polypeptide backbone. More preferably, the carbohydrate moiety is the terminal moiety of the carbohydrate side chain.

Consequently, in a preferred embodiment, the modified HAS is attached (via a linker or not, see below) to carbohydrate chains linked to N- and/or O-glycosylation sites of EPO.

However, it is also included within the present invention that the EPO contains (a) further carbohydrate moiet(y)ies to which the modified HAS is conjugated. Techniques for attaching carbohydrate moieties to polypeptides, either enzymatically or by genetic engineering, followed by expression in appropriate cells, are known in the art (Berger, Greber, Mosbach, 1986, Galactosyltransferase-dependent sialylation of complex and endo-N-acetylglucosaminidase H-treated core N-glycans in vitro, FEBS Lett., 203(1), 64-8; Dittmar, Conradt, Hauser, Hofer, Lindenmaier, 1989, Advances in Protein design; Bloecker, Collins, Schmidt, and Schomburg eds., GBF-Monographs, 12, 231-246, VCH Publishers, Weinheim, N.Y., Cambridge).

In a preferred embodiment of the method of the invention, the carbohydrate moiety is oxidized in order to be able to react with the modified HAS. This oxidation can be performed either chemically or enzymatically.

Methods for the chemical oxidation of carbohydrate moieties of polypeptides are known in the art and include the treatment with perjodate (Chamow et al., 1992, J. Biol. Chem., 267, 15916-15922).

By chemically oxidizing, it is principally possible to oxidize any carbohydrate moiety, being terminally positioned or not. However, by choosing mild conditions (1 mM perjodate, 0° C. in contrast to harsh conditions: 10 mM perjodate 1 h at room temperature), it is possible to preferably oxidize the terminal carbohydrate moiety, e.g. sialic acid or galactose, of a carbohydrate side chain.

Alternatively, the carbohydrate moiety may be oxidized enzymatically. Enzymes for the oxidation of the individual carbohydrate moieties are known in the art, e.g. in the case of galactose the enzyme is galactose oxidase.

If it is intended to oxidize terminal galactose moieties, it will be eventually necessary to remove terminal sialic acids (partially or completely) if the EPO has been produced in cells capable of attaching sialic acids to carbohydrate chains, e.g. in mammalian cells or in cells which have been genetically modified to be capable of attaching sialic acids to carbohydrate chains. Chemical or enzymatic methods for the removal of sialic acids are known in the art (Chaplin and Kennedy (eds.), 1996, Carbohydrate Analysis: a practical approach, especially Chapter 5 Montreuill, Glycoproteins, pages 175-177; IRL Press Practical approach series (ISBN 0-947946-44-3)).

However, it is also included within the present invention that the carbohydrate moiety to which the modified HAS is to be attached is attached to the EPO within step a). In the case it is desired to attach galactose, this can be achieved by the means of galactosyltransferase. The methods are known in the art (Berger, Greber, Mosbach, 1986, Galactosyltransferase-dependent sialylation of complex and endo-N-acetylglucosaminidase H-treated core N-glycans in vitro, FEBS Lett., 203(1), 64-8).

In a most preferred embodiment, in step a) the EPO is modified by oxidizing at least one terminal saccharide unit, preferably galactose, of the one or more carbohydrate side chains of the EPO, preferably after partial or complete (enzymatic and/or chemical) removal of the terminal sialic acid, if necessary (see above).

Consequently, preferably the modified HAS is conjugated to the oxidized terminal saccharide unit of the carbohydrate chain, preferably galactose.

Furthermore, the modified HAS may be preferably conjugated to a terminal sialic acid, which is preferably oxidized in step a) of the method of the invention.

In a further preferred embodiment (see point (3) above), the EPO comprises at least one free SH-group.

According to a preferred embodiment, this SH group may be linked to a preferably oxidized carbohydrate moiety, e.g. by using a hydroxylamine derivative, e.g. 2-(aminooxy)ethylmercaptan hydrochloride (Bauer L. et al., 1965, J. Org. Chem., 30, 949) or by using a hydrazide derivative, e.g. thioglycolic acid hydrazide (Whitesides et al., 1977, J. Org. Chem., 42, 332.) The methods for conjugating these molecules to the oxidized carbohydrate moiety of EPO may be analogous to those described in Example Protocols 8 and 9.

According to a further preferred embodiment, the free SH-group is part of a naturally-occurring cysteine or of an added cysteine.

Mammalian EPO has several cysteines which normally form disulfide bonds. However, by replacing at least one of the cysteines by another amino acid (e.g. by recombinant means), it is possible to obtain an EPO where at least one of the naturally occurring cysteines comprises a free SH-group. Methods for the replacement of amino acids are known in the art (Elliott, Lorenzini, Chang, Barzilay, Delorme, 1997, Mapping of the active site of recombinant human erythropoietin, Blood, 89(2), 493-502; Boissel, Lee, Presnell, Cohen, Bunn, 1993, Erythropoietin structure-function relationships. Mutant proteins that test a model of tertiary structure, J Biol. Chem., 268(21), 15983-93)).

Preferably, the EPO has the amino acid sequence of human EPO and the naturally occurring cysteines are cysteine 29 and/or 33.

Accordingly, in a preferred embodiment, cysteine 33 is replaced by another amino acid and in step c) the modified HAS is conjugated to cysteine 29.

In a further preferred embodiment, cysteine 29 is replaced by another amino acid and in step c) the modified HAS is conjugated to cysteine 33.

In the context of the present invention, by the term "added cysteines" it is meant that the polypeptides, preferably EPO, comprise a cysteine residue which is not present in the wild type polypeptide. This can be achieved by adding (e.g. by recombinant means) a cysteine residue either at the N- or at the C-terminus of the polypeptide or by replacing (e.g. by recombinant means) a naturally-occurring amino acid by cysteine. The respective methods are known to the person skilled in the art (see above).

Preferably, the added cysteine has been added by replacing a naturally occuring amino acid by a cysteine.

In a preferred embodiment, the EPO is human EPO and the replaced amino acid residue is serine 126.

Preferably, the modified HAS is conjugated in step c) to the added cysteine.

In step b) of the method of the invention, modified HAS is provided which is capable of reacting with the EPO of step a).

In this context, the HAS may be preferably modified at its reducing end. This has the advantage that the chemical reaction can be controlled easily and that the skilled person can be sure which group of HAS is modified during the reaction. Since only one group is introduced into the HAS, crosslinking between different EPO molecules by multifunctional HAS molecules and other side reactions can be prevented.

Accordingly, the modified HAS may be capable of reacting either with
(1) at least one group linked, either directly or via a linker molecule, to sulfide groups or carbohydrate moieties of EPO,
(2) at least one carbohydrate moiety, which is preferably oxidized, and/or
(3) at least one free SH-group.

With respect to point (1) above, the modification of HAS will depend on the group linked to EPO. The underlying mechanism are known in the art. An example is given in Example 4, 2.1.

With respect to points (2) and (3) above, several methods are known in the art to modify HAS. The basic principle underlying these methods is that either a reactive group of HAS is modified in order to be capable of reacting with the carbohydrate moiety or SH-group or a linker molecule is conjugated to HAS which contains a reactive group being capable of reacting with the carbohydrate moiety or SH-group.

In case of point (2), the modified HAS may be capable of reacting with oxidized carbohydrate moieties, preferably a terminal saccharide residue, more preferably galactose, or a terminal sialic acid.

Several ways are known to modify HAS such that it is capable of reacting with an oxidized, preferably terminal saccharide residue. As mentioned above, this modification may be introduced regioselectively at the reducing end of the HES-chain.

In this case, in a first step, the aldehyde group is oxidized to a lactone. The modifications include, but are not limited to the addition of hydrazide, amino (also hydroxylamino), semicarbazide or thiol functions to HAS, either directly or via a linker. These techniques are explained in further detail in Examples 2-4. Furthermore, the mechanisms per se are known in the art (see e.g. DE 196 28 705 A1; Hpoe et al., 1981, Carbohydrate Res., 91, 39; Fissekis et al., 1960, Journal of Medicinal and Pharmaceutical Chemistry, 2, 47; Frie, 1998, diploma thesis, Fach-hochschule Hamburg, Del.).

Within the present invention, the addition of a hydrazide or hydroxylamino function is preferred. In this case, by preferably conducting the reaction of step c) of the method of the present invention at a pH of 5.5, it is ensured that the modified HAS reacts selectively with the oxidized carbohydrate moiety of EPO without inter- or intramolecular EPO cross-linking by imine formation of lysin side chains with the oxidized saccharide residue.

In the case of point (3), also several ways are known to modify HAS such that it is capable of reacting with a free SH-group. Preferentially, this modification is introduced regioselectively at the reducing end of the HES-chain. The methods include, but are not limited to, the addition of maleimide, disulfide or halogen acetamide functions to HAS. These techniques are explained in further detail in Examples 2-4.

Further details about these techniques can be obtained from Chamov et al., 1992, J. Biol. Chem., 267, 15916; Thorpe et al., 1984, Eur. J. Biochem., 140, 63; Greenfield et al., 1990, Cancer Research, 50, 6600 as well as from the literature cited in Example 2, 1.3.

Further possible functions are listed in Table 1, providing a systematic overview over possible linker molecules. Furthermore, the mechanisms per se are known in the art.

Several linker molecules which are useful in the context of the present invention are known in the art or commercially available (e.g. from Pierce, available from Perbio Science Deutschland GmbH, Bonn, Germany). Examples are given in Table 2.

In step c) of the method of the present invention, the EPO of step a) with the HAS of step b) is reacted, whereby an HAS-EPO is produced comprising one or more HAS molecules, wherein the HAS is conjugated to the EPO via a carbohydrate moiety or via a thioether.

In principle, the detailed methods how to react the EPO with the modified HAS depend on the individual modification of the EPO and/or the HAS and are known in the art (see e.g. Rose, 1994, J. Am. Chem. Soc., 116, 30, O'Shannessay and Wichek, 1990, Analytical Biochemistry, 191, 1; Thorpe et al., 1984, Eur. J. Biochem., 140, 63; Chamov et al., 1992, J. Biol. Chem. 267, 15916).

For the methods exemplified in the present invention, the details are given in Examples 2-4, especially 4.

Step c) may be performed in a reaction medium comprising at least 10% per weight $H_2O$.

The reaction medium in this preferred embodiment of the method of the invention comprises at least 10% per weight water, preferred at least 50%, more preferred at least 80%, e.g. 90% or up to 100%. The degree of organic solvents is calculated respectively. Consequently, the reaction takes place in an aqueous phase. The preferred reaction medium is water.

One advantage of this embodiment of the method of the invention is, that it is not necessary to use toxicologically critical solvents and that therefore it is not necessary to remove these solvents after the production process, in order to avoid the contamination with the solvent. Furthermore, it is not necessary to perform additional quality controls with respect to residual toxicologically critical solvents. It is preferred to use as organic solvents toxicologically not critical solvents like ethanol or propylenglycol.

Another advantage of the method of the invention is that irreversible or reversible structural changes are avoided which are induced by organic solvents. Consequently, polypeptides obtained according to the method of the invention are different from those prepared in organic solvents such as DMSO.

Furthermore, it has been surprisingly observed that the conjugation of HAS to drugs in an aqueous solution minimizes or avoids side reactions. Consequently, this embodiment of the method of the invention leads to improved products with great purity.

In the context of the present invention, the term "hydroxyalkylstarch" is used to indicate starch derivatives which have been substituted by hydroxyalkylgroups. In this context, the alkyl group may be substituted. Preferably, the hydroxyalkyl contains 2-10 carbon atoms, more preferably 24 carbon atoms. "Hydroxyalkylstarch" therefore preferably comprises hydroxyethylstarch, hydroxypropylstarch and hydroxybutylstarch, wherein hydroxyethylstarch and hydroxypropylstarch are preferred.

The hydroxyalkylgroup(s) of HAS contain at least one OH-group.

Hydroxyethylstarch (HES) is most preferred for all embodiments of the present invention.

The expression "hydroxyalkylstarch" also includes derivatives wherein the alkyl group is mono- or polysubstituted. In this context, it is preferred that the alkyl group is substituted with a halogen, especially flourine, or with an aryl group, provided that the HAS remains water soluble. Furthermore, the terminal hydroxy group of hydroxyalkyl may be esterified or etherified. In addition, the alkyl group of the hydroxyalkylstarch may be linear or branched.

Furthermore, instead of alkyl, also linear or branched substituted or unsubstituted alkylene groups may be used.

In the context of the present invention, hydroxyethylstarch may have a mean molecular weight (weight mean) of 1-300 kDa, wherein a mean molecular weight of 5-100 kDa is more preferred. Hydroxyethylstarch may further exhibit a molar degree of substitution of 0.1 to 0.8 and a ratio between $C_2:C_6$-substitution in the range of 2-20, with respect to the hydroxyethylgroups.

The HAS-EPO produced by the method of the invention can be purified and characterized as follows:

Isolation of the HAS-EPO can be performed by using known procedures for the purification of natural and recombinant EPO (e.g. size exclusion chromatography, ion-exchange chromatography, RP-HPLC, hydroxyapatite chromatography, hydrophobic interaction chromatography, the procedure described in Example 20.8 or combinations thereof).

The covalent attachment of HAS to the EPO polypetide can be verified by carbohydrate compositional analysis after hydrolysis of the modified protein (ratio of hydroxyethylglucose and mannose present on the three N-glycosylation sites of EPO).

Demonstration of HAS modification at N-linked oligosaccharides of EPO can be accomplished by removal of the HAS modified N-glycans and observation of the predicted shift to higher mobility in SDS-PAGE +/− Western Blotting analysis.

HAS modification of EPO at cysteine residues can be demonstrated by the failure to detect the corresponding proteolytic Cys-peptide in RP-HPLC and MALDI/TOF-MS in the proteolytic fragments of the HAS-modified product (Zhou et al., 1998, Application of capillary electrophoresis, liquid chromatography, electrospray-mass spectrometry and matrix-assisted laserdesorption/ionization—time of flight—mass spectrometry to the characterization of recombinant human erythropoietin. Electrophoresis, 19(13), 2348-55). The isolation of the HAS-containing fraction after proteolytic digestion of the Cys-modified EPO enables the verification in this fraction of the corresponding peptide by conventional amino acid compositional analysis.

All embodiments disclosed above with respect of the HAS-EPO of the invention concerning properties of EPO or HAS apply also to the method of the invention for preparing a HAS-EPO.

The invention further relates to a HAS-EPO, obtainable by the method of the invention. Preferably, this HAS-EPO has the features as defined for the above HAS-EPO of the invention.

The invention further relates to a HAS-EPO according to the invention for use in a method for treatment of the human or animal body.

Furthermore, the present invention relates to a pharmaceutical composition comprising the HAS-EPO of the invention. In a preferred embodiment, the pharmaceutical composition comprises further at least one pharmaceutically acceptable diluent, adjuvant and/or carrier useful in erythropoietin therapy.

The pharmaceutical composition is preferably used for the treatment of anemic disorders or hematopoietic dysfunction disorders or diseases related thereto.

A "therapeutically effective amount" as used herein refers to that amount which provides therapeutic effect for a given condition and administration regimen. The administration of erythropoietin isoforms is preferably by parenteral routes. The specific route chosen will depend upon the condition being treated. The administration of erythropoietin isoforms is preferably done as part of a formulation containing a suitable carrier, such as human serum albumin, a suitable diluent, such as a buffered saline solution, and/or a suitable adjuvant. The required dosage will be in amounts sufficient to raise the hematocrit of patients and will vary depending upon the severity of the condition being treated, the method of administration used and the like.

The object of the treatment with the pharmaceutical composition of the invention is preferably an increase of the hemoglobin value of more than 6.8 mmol/l in the blood. For this, the pharmaceutical composition may be administered in a way that the hemoglobin value increases between 0.6 mmol/l and 1.6 mmol/l per week. If the hemoglobin value exceeds 8.7 mmol/l, the therapy should be preferably interrupted until the hemoglobin value is below 8.1 mmol/l.

The composition of the invention is preferably used in a formulation suitable for subcutaneous or intravenous or parenteral injection. For this, suitable excipients and carriers are e.g. sodium dihydrogen phosphate, disodium hydrogen phosphate, sodium chlorate, polysorbate 80, HSA and water for injection. The composition may be administered three times a week, preferably two times a week, more preferably once a week, and most preferably every two weeks.

Preferably, the pharmaceutical composition is administered in an amount of 0.01-10 μg/kg body weight of the patient, more preferably 0.1 to 5 μg/kg, 0.1 to 1 μg/kg, or 0.2-0.9 μg/kg, most preferably 0.3-0.7 μg/kg, and most preferred 0.4-0.6 μg/kg body weight.

In general, preferably between 10 μg and 200 μg, preferably between 15 μg and 100 μg are administered per dose.

The invention further relates to the use of a HAS-EPO of the invention for the preparation of a medicament for the treatment of anemic disorders or hematopoietic dysfunction disorders or diseases related hereto.

According to a further aspect of the present invention, the problem is solved by a hydroxyalkylstarch (HAS)-polypeptide-conjugate (HAS-polypeptide) comprising one or more HAS molecules, wherein each HAS is conjugated to the polypeptide via a) a carbohydrate moiety; or
    b) a thioether.

The HAS-polypeptide of the invention has the advantage that it exhibits an improved biological stability when compared to the polypeptide before conjugation. This is mainly due to the fact that HAS-polypeptide is less or not recognized by the removal systems of the liver and kidney and therefore persists in the circulatory system for a longer period of time. Furthermore, since the HAS is attached site-specifically, the risk of destroying the in vivo biological activity of the polypeptide by conjugation of HAS to the polypeptide is minimized.

The HAS-polypeptide of the invention has mainly two components, namely the polypeptide and the hydroxyalkyl-starch (HAS) linked thereto.

The polypeptide can be of any human or animal source. In a preferred embodiment, the polypeptide is of human source.

The polypeptide may be a cytokine, especially erythropoietin, an antithrombin (AT) such as AT III, an interleukin, especially interleukin-2, IFN-beta, IFN-alpha, G-CSF, CSF, interleukin-6 and therapeutic antibodies.

According to a preferred embodiment, the polypeptide is an antithrombin (AT), preferably AT III (Levy J H, Weisinger A, Ziomek C A, Echelard Y, Recombinant Antithrombin: Production and Role in Cardiovascular Disorder, Seminars in Thrombosis and Hemostasis 27, 4 (2001) 405-416; Edmunds T, Van Patten S M, Pollock J, Hanson E, Beenasconi R, Higgins E, Manavalan P, Ziomek C, Meade H, McPherson J, Cole E S, Transgenically Produced Human Antithrombin: Structural and Functional Comparison to Human Plasma-Derived Antithrombin, Blood 91, 12 (1998) 4661-4671; Minnema M C, Chang A C K, Jansen P M, Lubbers Y T P, Pratt B M, Whittaker B G, Taylor F B, Hack C E, Friedman B, Recombinant human antithrombin III improves survival and attenuates inflammatory responses in baboons lethally challenged with *Escherichia coli*, Blood 95, 4 (2000) 1117-1123; Van Patten S M, Hanson E H, Bernasconi R, Zhang K, Manavaln P, Cole E S, McPherson J M, Edmunds T, Oxidation of Methionine Residues in Antithrombin, J. Biol. Chemistry 274, 15 (1999) 10268-10276).

According to another preferred embodiment, the polypeptide is human IFN-beta, in particular IFN-beta 1a (cf. Avonex®, REBIF®) and IFN-beta 1b (cf. BETASERON®).

A further preferred polypeptide is human G-CSF (granulocyte colony stimulating factor). See, e.g., Nagata et al., The chromosomal gene structure and two mRNAs for human granulocyte colony-stimulating factor, EMBO J. 5: 575-581, 1986; Souza et al., Recombinant human granulocyte colony-stimulating factor: effects on normal and leukemic myeloid cells, Science 232 (1986) 61-65; and Herman et to al., Characterization, formulation, and stability of Neupogen® (Filgrastim), a recombinant human granulocyte-colony stimulating factor, in: Formulalion, characterization, and stability of protein drugs, Rodney Pearlman and Y. John Wang, eds., Plenum Press, New York, 1996, 303-328.

With respect to erythropoictin, all embodiments disclosed above also apply here.

Preferably, the polypeptide is recombinantly produced. This includes the production in eukaryotic or prokaryotic cells, preferably mammalian, insect, yeast, bacterial cells or in any other cell type which is convenient for the recombinant production of the polypeptide. Furthermore, the polypeptide may be expressed in transgenic animals (e.g. in body fluids like milk, blood, etc.), in eggs of transgenic birds, especially poultry, preferred chicken, or in transgenic plants.

The recombinant production of a polypeptide is known in the art. In general, this includes the transfection of host cells with an appropriate expression vector, the cultivation of the host cells under conditions which enable the production of the polypeptide and the purification of the polypeptide from the host cells. For detailled information see e.g. Krystal, Pankratz, Farber, Smart, 1986, Purification of human erythropoietin to homogeneity by a rapid five-step procedure, Blood, 67(1), 71-9; Quelle, Caslake, Burkert, Wojchowski, 1989, High-level expression and purification of a recombinant human erythropoietin produced using a baculovirus vector, Blood, 74(2), 652-7; EP 640 619 B1 and EP 668 351 B1.

The polypeptide may comprise one or more carbohydrate side chains attached to the polypetide via N- and/or O-linked glycosylation, i.e. the polypeptide is glycosylated. Usually, when a polypeptide is produced in eukaryotic cells, the polypeptide is posttranslationally glycosylated. Consequently, the carbohydrate side chains may have been attached to the polypeptide during biosynthesis in mammalian, especially human, insect or yeast cells.

The HAS may be directly conjugated to the polypeptide or, alternatively, via a linker molecule. The nature of the linker molecule depends on the way how the HAS is linked to the polypeptide. Several linkers are commercially available (e.g. from Pierce, see above). The nature of the linker and its purpose are described in detail below in the section concerning the method for the production of HES-polypeptide is discussed.

According to a preferred embodiment of the HAS-polypeptide conjugate of the invention, the HAS is conjugated to the polypeptide via a carbohydrate moiety. Preferably, this applies if the polypeptide is an antithrombin, preferably AT III.

In the context of the present invention, the term "carbohydrate moiety" refers to hydroxyaldehydes or hydroxyketones as well as to chemical modifications thereof (see Römpp Chemielexikon, 1990, Thieme Verlag Stuttgart, Germany, $9^{th}$ edition, 9, 2281-2285 and the literature cited therein). Furthermore, it also refers to derivatives of naturally occuring carbohydrate moieties like glucose, galactose, mannose, sialic acid, and the like. The term also includes chemically oxidized naturally occuring carbohydrate moieties wherein the ring structure has been opened.

The carbohydrate moiety may be linked directly to the polypeptide backbone. Preferably, the carbohydrate moiety is part of a carbohydrate side chain. In this case, further carbohydrate moieties may be present between the carbohydrate moiety to which HAS is linked and the polypeptide backbone. More preferably, the carbohydrate moiety is the terminal moiety of the carbohydrate side chain.

In a more preferred embodiment, the HAS is conjugated to a galactose residue of the carbohydrate side chains, preferably the terminal galactose residue of the carbohydrate side chain. This galactose residue can be made available for conjugation by removal of terminal sialic acids, followed by oxidation (see below).

In a further more preferred embodiment, the HAS is conjugated to a sialic acid residue of the carbohydrate side chains, preferably the terminal sialic acid residue of the carbohydrate side chain.

Furthermore, the HAS may be conjugated to the polypeptide via a thioether. As explained in detail below, the S atom can be derived from any SH group attached to the polypeptide, both naturally or non naturally occurring.

In a preferred embodiment, the S atom may be derived from a SH group which has been introduced in an oxidized carbohydrate moiety of HES, preferably an oxidized carbohydrate moiety which is part of a carbohydrate side chain of the polypeptide (see below).

Preferably, the S atom in the thioether is derived from a naturally-occurring cysteine or from an added cysteine.

In the context of the present invention, by the term "added cysteines" it is meant that the polypeptides comprise a cysteine residue which is not present in the wild-type polypeptide.

In the context of this aspect of the invention, the cysteine may be an additional amino acid added at the N- or C-terminal end of the polypeptide.

Furthermore, the added cysteine may have been added by replacing a naturally occuring amino acid by a cysteine.

The second component of the HAS-polypeptide is HAS.

In the context of the present invention, the term "hydroxyalkylstarch" is used to indicate starch derivatives which have been substituted by hydroxyalkylgroups. In this context, the alkyl group may be substituted. Preferably, the hydroxyalkyl contains 2-10 carbon atoms, more preferably 2-4 carbon atoms. "Hydroxyalkylstarch" therefore preferably comprises hydroxyethylstarch, hydroxypropylstarch and hydroxybutylstarch, wherein hydroxyethylstarch and hydroxypropylstarch are preferred.

The hydroxyalkylgroup(s) of HAS contain at least one OH-group.

The expression "hydroxyalkylstarch" also includes derivatives wherein the alkyl group is mono- or polysubstituted. In this context, it is preferred that the alkyl group is substituted with an halogen, especially flourine, or with an aryl group, provided that the HAS remains water soluble. Furthermore, the terminal hydroxy group of hydroxyalkyl may be esterified or etherified. In addition, the alkyl group of the hydroxyalkylstarch may be linear or branched.

Furthermore, instead of alkyl, also linear or branched substituted or unsubstituted alkene groups may be used.

Hydroxyethylstarch (HES) is most preferred for all embodiments of the present invention.

In the context of the present invention, hydroxyethylstarch may have a mean molecular weight (weight mean) of 1-300 kDa, wherein a mean molecular weight of 5-100 kDa is more preferred. Hydroxyethylstarch can further exhibit a molar degree of substitution of 0.1 to 0.8 and a ratio between $C_2:C_6$-substitution in the range of 2-20, with respect to the hydroxyethylgroups.

The HAS-polypeptide may comprise 1-12, preferably 1-9, 1-6 or 1-3, most preferred 1-4 HAS molecules per polypeptide molecule. The number of HAS-molecules per polypeptide molecule can be determined by quantitative carbohydrate compositional analysis using GC-MS after hydrolysis of the product and derivatisation of the resulting monosaccharides (Chaplin and Kennedy, 1986, Carbohydrate Analysis (eds.): a practical approach ed., Chapter 1. Monosaccharides page 1-36; Chapter 2. Oligosaccharides page 37-53; Chapter 3. Neutral Polysaccharides; 55-96; IRL Press Practical approach series (ISBN 0-947946-44-3).

All embodiments disclosed below with respect of the method of the invention to produce a HAS-polypeptide concerning properties of the polypeptide or HAS apply also to the HAS-polypeptide of the invention. Furthermore, all embodiments disclosed above with respect to HAS-EPO or the preparation thereof which relate to peptides in general or to HAS apply also to the HAS-polypeptide of the invention.

Hydroxyalkylstarch is an ether derivative of starch. Besides of said ether derivatives, also other starch derivatives can be used in the context of the present invention. For example, derivatives are useful which comprise esterified hydroxy groups. These derivatives may be e.g. derivatives of unsubstituted mono- or dicarboxylic acids with 2-12 carbon atoms or of substituted derivatives thereof. Especially useful are derivatives of unsubstituted monocarboxylic acids with 2-6 carbon atoms, especially of acetic acid, In this context, acetylstarch, butylstarch or propylstarch are preferred.

Furthermore, derivatives of unsubstituted dicarboxylic acids with 2-6 carbon atoms are preferred.

In the case of derivatives of dicarboxylic acids, it is useful that the second carboxy group of the dicarboxylic acid is also esterified. Furthermore, derivatives of monoalkyl esters of dicarboxylic acids are also suitable in the context of the present invention.

For the substituted mono- or dicarboxylic acids, the substitute groups may be preferably the same as mentioned above for substituted alkyl residues.

Techniques for the esterification of starch are known in the art (see e.g. Klemm D. et al, Comprehensive Cellulose Chemistry Vol. 2, 1998, Whiley-VCH, Weinheim, N.Y., especially chapter 4.4, Esterification of Cellulose (ISBN 3-527-29489-9).

In a further aspect, the present invention relates to a method for the production of a hydroxyalkylstarch (HAS)-polypeptide-conjugate (HAS-polypeptide), comprising the steps of:
a) providing a polypeptide being capable of reacting with modified HAS,
b) providing modified HAS being capable of reacting with the polypeptide of step a), and
c) reacting the polypeptide of step a) with the HAS of step b), whereby an HAS-polypeptide is produced comprising one or more HAS molecules, wherein the HAS is conjugated to the polypeptide via
i) a carbohydrate moiety; or
ii) a thioether.

The method of the invention has the advantage that a HAS-polypeptide conjugate is produced which exhibits a high biological activity. Furthermore, the method of the invention has the advantage that an effective polypeptide derivative can be produced at reduced cost since the method does not comprise extensive and time consuming purification steps resulting in low final yield.

Accordingly, in the first step of the method of the invention, a polypeptide is provided which is capable of reacting with modified HAS.

As used in the present invention, the term "providing" has to be interpreted in the way that after the respective step a molecule (in step a) a polypeptide, in step b) HAS) with the desired properties is available.

In the case of step a), this includes the purification of the polypeptide from natural sources as well as the recombinant production in host cells or organism, and, if necessary, the modification of the polypeptide so obtained.

With respect to the polypeptide being the starting material of the present invention, the same applies as for the erythropoietin being part of the HAS-polypeptide conjugate of the invention. In this context, the preferred embodiments disclosed above apply also for the method of the invention.

Preferably, the polypeptide is recombinantly produced. This includes the production in eukaryotic or prokaryotic cells, preferably mammalian, insect, yeast, bacterial cells or in any other cell type which is convenient for the recombinant production of the polypeptide. Furthermore, the polypeptide may be expressed in transgenic animals (e.g. in body fluids like milk, blood, etc.), in eggs of transgenic birds, especially poultry, preferred chicken, or in transgenic plants.

The recombinant production of a polypeptide is known in the art. In general, this includes the transfection of host cells with an appropriate expression vector, the cultivation of the host cells under conditions which enable the production of the polypeptide and the purification of the polypeptide from the host cells (Krystal, Pankratz, Farber, Smart, 1986, Purification of human erythropoietin to homogeneity by a rapid five-step procedure, Blood, 67(1), 71-9; Quelle, Caslake, Burkert, Wojchowski, 1989, High-level expression and purification of a recombinant human erythropoietin produced using a baculovirus vector, Blood, 74(2), 652-7; EP 640 619 B1 and EP 668 351 B1).

The polypeptide may comprise one or more carbohydrate side chains attached to the polypeptide via N- and/or O-linked glycosylation, i.e. the polypeptide is glycosylated. Unsually, when the polypeptide is produced in eukaryotic cells, the polypeptide is posttranslationally glycosylated. Consequently, the carbohydrate side chains may have been attached to the polypeptide during production in mammalian, especially human, insect or yeast cells, wherein the cells may be those of a transgenic animal or plant (see above).

These carbohydrate side chains may have been chemically or enzymatically modified after the expression in the appropriate cells, e.g. by removing or adding one or more carbohydrate moieties (see e.g. Dittmar, Conradt, Hauser, Hofer, Lindenmaier, 1989, Advances in Protein design; Bloecker, Collins, Schmidt, and Schomburg eds., GBF-Monographs, 12, 231-246, VCH Publishers, Weinheim, N.Y., Cambridge).

It is the object of the method of the invention to provide an HAS-polypeptide comprising one or more HAS molecules wherein the HAS is conjugated to the polypeptide via a carbohydrate moiety (i) or via a thioether (ii). Consequently, the polypeptide provided in step a) should have the properties that a conjugation via a carbohydrate moiety and/or via a thioether is possible. Therefore the polypeptide after step a) may preferably contain either (1) at least one reactive group linked, either directly or via a linker molecule, to sulfide groups or carbohydrate moieties, which is capable to react with HES or modified HES,
(2) at least one carbohydrate moiety to which modified HAS can be conjugated, and/or
(3) at least one free SH-group.

With respect to possibility (1) above, the polypeptide of step a) is preferably obtainable by conjugating an appropriate linker molecule to the SH-group(s) or carbohydrate moieties of the polypeptide. An example for such a modified polypeptide is provided in Example 4, 2.1. It is important to ensure that the addition of the linker molecule does not damage the polypeptide. However, this is known to the person skilled in the art.

With respect to possibility (2) above, in a preferred embodiment, the modified HAS is conjugated to the polypeptide via a carbohydrate moiety.

The carbohydrate moiety may be linked directly to the polypeptide backbone. Preferably, the carbohydrate moiety is part of a carbohydrate side chain. In this case, further carbohydrate moieties may be present between the carbohydrate moiety to which HAS is linked and the polypeptide backbone. More preferably, the carbohydrate moiety is the terminal moiety of the carbohydrate side chain.

Consequently, in a preferred embodiment, the modified HAS is attached (via a linker or not, see below) to carbohydrate chains linked to N- and/or O-glycosylation sites of the polypeptide.

However, it is also included within the present invention that the polypeptide contains (a) further carbohydrate moiet(y)ies to which the modified HAS is conjugated. Techniques for attaching carbohydrate moieties to polypeptides, either enzymatically or by genetic engineering, followed by expression in appropriate cells, are known in the art (Berger, Greber, Mosbach, 1986, Galactosyltransferase-dependent sialylation of complex and endo-N-acetylglucosaminidase H-treated core N-glycans in vitro, FEBS Lett., 203(1), 64-8; Dittmar, Conradt, Hauser, Hofer, Lindenmaier, 1989, Advances in Protein design; Bloecker, Collins, Schmidt, and Schomburg eds., GBF-Monographs, 12, 231-246, VCH Publishers, Weinheim, N.Y., Cambridge).

In a preferred embodiment of the method of the invention, the carbohydrate moiety is oxidized in order to be able to react with the modified HAS. This oxidation can be performed either chemically or enzymatically.

Methods for the chemical oxidation of carbohydrate moieties of polypeptides are known in the art and include the treatment with perjodate (Chamow et al., 1992, J. Biol. Chem., 267, 15916-15922).

By chemically oxidizing, it is principally possible to oxidize any carbohydrate moiety, being terminally positioned or not. However, by choosing mild conditions (1 mM periodate, 0° C. in contrast to harsh conditions: 10 mM periodate 1 h at room temperature), it is possible to preferably oxidize the terminal carbohydrate moiety, e.g. sialic acid or galactose, of a carbohydrate side chain.

Alternatively, the carbohydrate moiety may be oxidized enzymatically. Enzymes for the oxidation of the individual carbohydrate moieties are known in the art, e.g. in the case of galactose the enzyme is galactose oxidase.

If it is intended to oxidize terminal galactose moieties, it will be eventually necessary to remove terminal sialic acids (partially or completely) if the polypeptide has been produced in cells capable of attaching sialic acids to carbohydrate chains, e.g. in mammalian cells or in cells which have been genetically modified to be capable of attaching sialic acids to carbohydrate chains. Chemical or enzymatic methods for the removal of sialic acids are known in the art (Chaplin and Kennedy (eds.), 1996, Carbohydrate Analysis: a practical approach, especially Chapter 5 Montreuill, Glycoproteins, pages 175-177; IRL Press Practical approach series (ISBN 0-947946-44-3)).

However, it is also included within the present invention that the carbohydrate moiety to which the modified HAS is to be attached is attached to the polypeptide within step a). In the case it is desired to attach galactose, this can be achieved by the means of galactose transferase. The methods are known in the art (Berger, Greber, Mosbach, 1986, Galactosyltransferase-dependent sialylation of complex and endo-N-acetylglucosaminidase H-treated core N-glycans in vitro, FEBS Lett., 203(1), 64-8).

In a most preferred embodiment, in step a) the polypeptide is modified by oxidizing at least one terminal saccharide unit, preferably galactose, of the one or more carbohydrate side chains of the polypeptide, preferably after partial or complete (enzymatic and/or chemical) removal of the terminal sialic acid, if necessary (see above).

Consequently, preferably the modified HAS is conjugated to the oxidized terminal saccharide unit of the carbohydrate chain, preferably galactose.

In a further preferred embodiment (see point (3) above), the polypeptide comprises at least one free SH-group.

According to a preferred embodiment, the free SH-group is part of a naturally-occurring cysteine or of an added cysteine.

Methods for the replacement of amino acids are known in the art (Elliott, Lorenzini, Chang, Barzilay, Delorme, 1997, Mapping of the active site of recombinant human erythropoietin, Blood, 89(2), 493-502; Boissel, Lee, Presnell, Cohen, Bunn, 1993, Erythropoietin structure-function relationships. Mutant proteins that test a model of tertiary structure, J Biol. Chem., 268(21), 15983-93)).

In the context of the present invention, by the term "added cysteines" it is meant that the polypeptides comprise a cysteine residue which is not present in the wild type polypeptide. This can be achieved by adding (e.g. by recombinant means) a cysteine residue either at the N- or at the C-terminus of the polypeptide or by replacing (e.g. by recombinant means) a naturally-occurring amino acid by cysteine. The respective methods are known to the person skilled in the art (see above).

Preferably, the added cysteine has been added by replacing a naturally occuring amino acid by a cysteine.

Preferably, the modified HAS is conjugated in step c) to the added cysteine.

In step b) of the method of the invention, modified HAS is provided which is capable of reacting with the polypeptide of step a).

In this context, the HAS may be preferably modified at its reducing end. This has the advantage that the chemical reaction can be controlled easily and that the skilled person can be sure which group of HAS is modified during the reaction. Since only one group is introduced into the HAS, crosslinking between different polypeptide molecules by multifunctional HAS molecules and other side reactions can be prevented.

Accordingly, the modified HAS may be capable of reacting either with
(1) at least one group linked, either directly or via a linker molecule, to sulfide groups or carbohydrate moieties of the polypeptide,
(2) at least one carbohydrate moiety, which is preferably oxidized, and/or
(3) at least one free SH-group.

With respect to point (1) above, the modification of HAS will depend on the group linked to the polypeptide. The underlying mechanism are known in the art. An example is given in Example 4, 2.1.

With respect to points (2) and (3) above, several methods are known in the art to modify HAS. The basic principle underlying these methods is that either a reactive group of HAS is modified in order to be capable of reacting with the carbohydrate moiety or SH-group or a linker molecule is conjugated to HAS which contains a reactive group being capable of reacting with the carbohydrate moiety or SH-group.

In case of point (2), the modified HAS may be capable of reacting with oxidized carbohydrate moieties, preferably a terminal saccharide residue, more preferably galactose, or with a terminal sialic acid.

Several ways are known to modify HAS such that it is capable of reacting with an oxidized, preferably terminal saccharide residue. As mentioned above, this modification may be introduced regioselectively at the reducing end of the HES-chain. In this case, in a first step, the aldehyde group is oxidized to a lactone. The modifications include, but are not limited to the addition of hydrazide, amino (also hydroxylamino), semicarbazide or thiol functions to HAS, either directly or via a linker. These techniques are explained in further detail in Examples 24. Furthermore, the mechanisms per se are known in the art (see e.g. DE 196 28 705 A1; Hpoe et al., 1981, Carbohydrate Res., 91, 39; Fissekis et al., 1960, Journal of Medicinal and Pharmaceutical Chemistry, 2, 47; Frie, 1998, diploma thesis, Fach-hochschule Hamburg, Del.).

Within the present invention, the addition of a hydrazide or hydroxylamino function is preferred. In this case, by preferably conducting the reaction of step c) of the method of the present invention at a pH of 5.5, it is ensured that the modified HAS reacts selectively with the oxidized carbohydrate moiety of the polypeptide without inter- or intramolecular polypeptide cross-linking by imine formation of lysine side chains with the oxidized saccharide residue.

In the case of point (3), also several ways are known to modify HAS such that it is capable of reacting with a free SH-group. Preferentially, this modification is introduced regioselectively at the reducing end of the HES-chain. The methods include, but are not limited to the addition of maleimide, disulfide or halogen acetamide functions to HAS. These techniques are explained in further detail in Examples 2-4.

Further details about these techniques can be obtained from Chamov et al., 1992, J. Biol. Chem., 267, 15916; Thorpe et al., 1984, Eur. J. Biochem., 140, 63; Greenfield et al., 1990, Cancer Research, 50, 6600 as well as from the literature cited in Example 2, 1.3.

Further possible functions are listed in Table 1, providing a systematic overview over possible linker molecules. Furthermore, the mechanisms per se are known in the art.

Several linker molecules which are useful in the context of the present invention are known in the art or commercially available (e.g. from Pierce, available from Perbio Science Deutschland GmbH, Bonn, Germany).

In step c) of the method of the present invention, the polypeptide of step a) with the HAS of step b) is reacted, whereby an HAS-polypeptide is produced comprising one or more HAS molecules wherein the HAS is conjugated to the polypeptide via a carbohydrate moiety or via a thioether.

In principle, the detailed methods how to react the polypeptide with the modified HAS depend on the individual modification of the polypeptide and/or the HAS and are known in the art (see e.g. Rose, 1994, J. Am. Chem. Soc., 116, 30; O'Shannessay and Wichek, 1990, Analytical Biochemistry, 191, 1; Thorpe et al., 1984, Eur. J. Biochem., 140, 63; Chamov et al., 1992, J. Biol. Chem., 267, 15916).

For the methods exemplified in the present invention, the details are given in Examples 2-4, especially 4.

Step c) may be performed in a reaction medium comprising at least 10% per weight $H_2O$.

The reaction medium in this preferred embodiment of the method of the invention comprises at least 10% per weight water, preferred at least 50%, more preferred at least 80%, e.g. 90% or up to 100%. The degree of organic solvents is calculated respectively. Consequently, the reaction takes place in an aqueous phase. The preferred reaction medium is water.

One advantage of this embodiment of the method of the invention is, that it is not necessary to use toxicologically critical solvents and that therefore it is not necessary to remove these solvents after the production process, in order to avoid the contamination with the solvent. Furthermore, it is not necessary to perform additional quality controls with respect to residual toxicologically critical solvents. It is preferred to use as organic solvents toxicologically not critical solvents like ethanol or propylenglycol.

Another advantage of the method of the invention is that irreversible or reversible structural changes are avoided which are induced by organic solvents. Consequently, polypeptides obtained according to the method of the invention are different from those prepared in organic solvents such as DMSO.

Furthermore, it has been surprisingly observed that the conjugation of HAS to drugs in an aqueous solution avoids side reactions. Consequently, this embodiment of the method of the invention leads to improved products with great purity.

In the context of the present invention, the term "hydroxyalkylstarch" is used to indicate starch derivatives which have been substituted by hydroxyalkylgroups. In this context, the alkyl group may be substituted. Preferably, the hydroxyalkyl contains 2-10 carbon atoms, more preferably 24 carbon atoms. "Hydroxyalkylstarch" therefore preferably comprises hydroxyethylstarch, hydroxypropylstarch and hydroxybutylstarch, wherein hydroxyethylstarch and hydroxypropylstarch are preferred.

The hydroxyalkylgroup(s) of HAS contain at least one OH-group.

Hydroxyethylstarch (HES) is most preferred for all embodiments of the present invention.

The expression "hydroxyalkylstarch" also includes derivatives wherein the alkyl group is mono- or polysubstituted. In this context, it is preferred that the alkyl group is substituted with an halogen, especially flourine, or with an aryl group, provided that the HAS remains water soluble. Furthermore, the terminal hydroxy group of hydroxyalkyl may be esterified or etherified. In addition, the alkyl group of the hydroxyalkylstarch may be linear or branched.

Furthermore, instead of alkyl, also linear or branched substituted or unsubstituted alkylene groups may be used.

In the context of the present invention, hydroxyethylstarch may have a mean molecular weight (weight mean) of 1-300 kDa, wherein a mean molecular weight of 5-100 kDa is more preferred. Hydroxyethylstarch may further exhibit a molar degree of substitution of 0.1 to 0.8 and a ratio between $C_2:C_6$-substitution in the range of 2-20, with respect to the hydroxyethylgroups.

The HAS-polypeptide produced by the method of the invention can be purified and characterized as follows:

Isolation of the HAS-polypeptide can be performed by using known procedures for the purification of natural and recombinant polypeptides (e.g. size exclusion chromatography, ion-exchange chromatography, RP-HPLC, hydroxyapatite chromatography, hydrophobic interaction chromatography, the procedure described in Example 20.8 or combinations thereof).

The covalent attachment of HAS to the polypetide can be verified by carbohydrate compositional analysis after hydrolysis of the modified protein.

Demonstration of HAS modification at N-linked oligosaccharides of the polypeptide can be accomplished by removal of the HAS modified N-glycans and observation of the predicted shift to higher mobility in SDS-PAGE +/− Western Blotting analysis.

HAS modification of the polypeptide at cysteine residues can be demonstrated by the failure to detect the corresponding proteolytic Cys-peptide in RP-HPLC and MALDI/TOF-MS in the proteolytic fragments of the HAS-modified product (Zhou et al., 1998, Application of capillary electrophoresis, liquid chromatography, electrospray-mass spectrometry and matrix-assisted laserdesorption/ionization—time of flight—mass spectrometry to the characterization of recombinant human erythropoietin, Electrophoresis, 19(13), 2348-55). The isolation of the HAS-containing fraction after proteolytic digestion of the Cys-modified polypeptide enables the verification in this fraction of the corresponding peptide by conventional amino acid compositional analysis.

All embodiments disclosed above with respect of the HAS-polypeptide of the invention concerning properties of the polypeptide or HAS apply also to the method of the invention for the production of a HAS-polypeptide conjugate. Furthermore, all embodiments disclosed above with respect to HAS-EPO or the preparation thereof which relate to peptides in general or to HAS apply also to the method of the invention for the production of a HAS-polypeptide conjugate.

The invention further relates to a HAS-polypeptide, obtainable by the method of the invention. Preferably, this HAS-polypeptide has the features as defined for the above HAS-polypeptide of the invention.

According to a preferred embodiment of the present invention, the HAS used has the following formula (I)

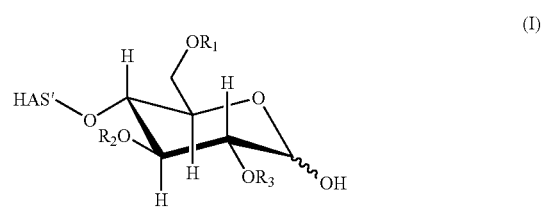

(I)

wherein $R_1$, $R_2$ and $R_3$ are independently hydrogen or a linear or branched hydroxyalkyl group. The term "hydroxyalkyl starch" as used in the present invention is not limited to compounds where the terminal carbohydrate moiety comprises hydroxyalkyl groups $R_1$, $R_2$, and/or $R_3$ as depicted, for the sake of brevity, in formula (I), but also refers to compounds in which at least one hydroxy group present anywhere, either in the terminal carbohydrate moiety and/or in the remaining part of the starch molecule, HAS', is substituted by a hydroxyalkyl group $R_1$, $R_2$, or $R_3$. In this context, the alkyl group may be a linear or branched alkyl group which may be suitably substituted. Preferably, the hydroxyalkyl group contains 1 to 10 carbon atoms, more preferably from 1 to 6 carbon atoms, more preferably from 1 to 4 carbon atoms, and even more preferably 2-4 carbon atoms. "Hydroxyalkyl starch" therefore preferably comprises hydroxyethyl starch, hydroxypropyl starch and hydroxybutyl starch, wherein hydroxyethyl starch and hydroxypropyl starch are particularly preferred, hydroxyethyl starch being especially preferred.

HAS and preferably HES may be reacted with a crosslinking compound which reacts with HAS, preferably HES, and the polypeptide such as the polypeptides described above.

The reaction between HAS and the crosslinking compound may take place at the reducing end of HAS or at the oxidised reducing end of HAS. Therefore, HAS may be reacted having a structure according to formula (I)

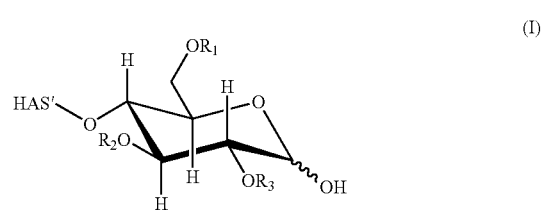

(I)

and/or, in case the reducing end is oxidised, according to formula (IIa)

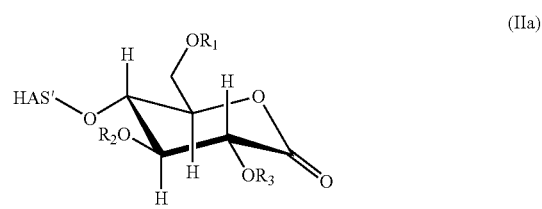

(IIa)

and/or according to formula (IIb)

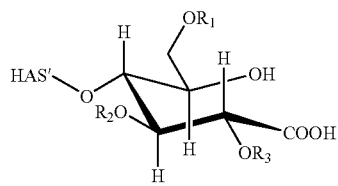

If HAS according to formula (I) is reacted with a crosslinking compound, the reaction preferably takes place in an aqueous medium. If HAS according to formula (IIa) and/or (IIb) is reacted with a crosslinking compound, the reaction preferably takes place in a non-aqueous medium such as in a polar aprotic solvent or solvent mixture such as DMSO and/or in DMF.

If the HAS-polypeptide conjugate of the present invention is produced via reaction of a HAS derivative, comprising HAS and a crosslinking compound, with the oxidised carbohydrate moiety of the polypeptide, the crosslinking compound is preferably a compound

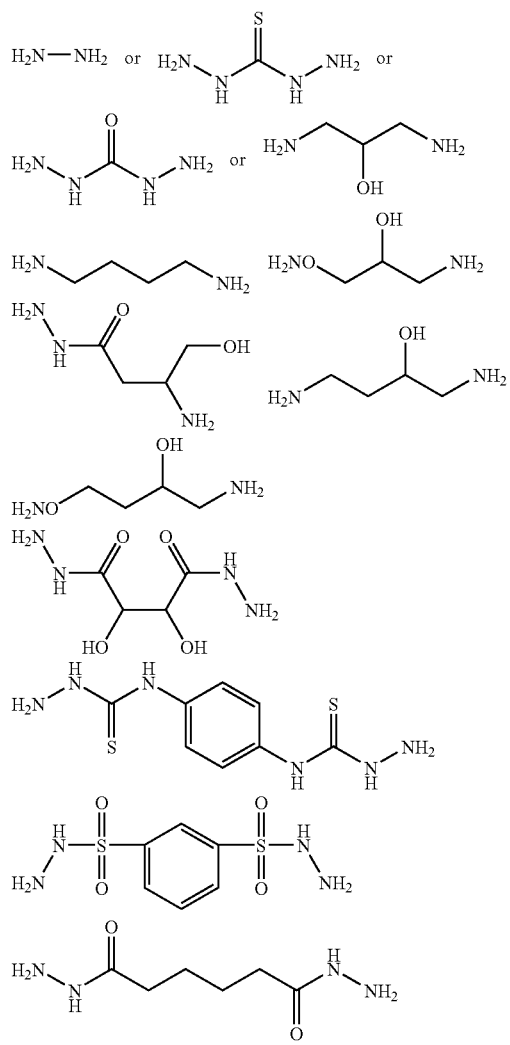

-continued

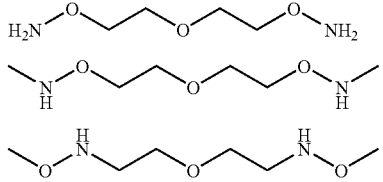

If the HAS-polypeptide conjugate of the present invention is produced via reaction of a HAS derivative, comprising HAS and at least one crosslinking compound, with the thio group of the polypeptide, it is preferred to react HAS at its optionally oxidized reducing end with a first crosslinking compound which is preferably a compound

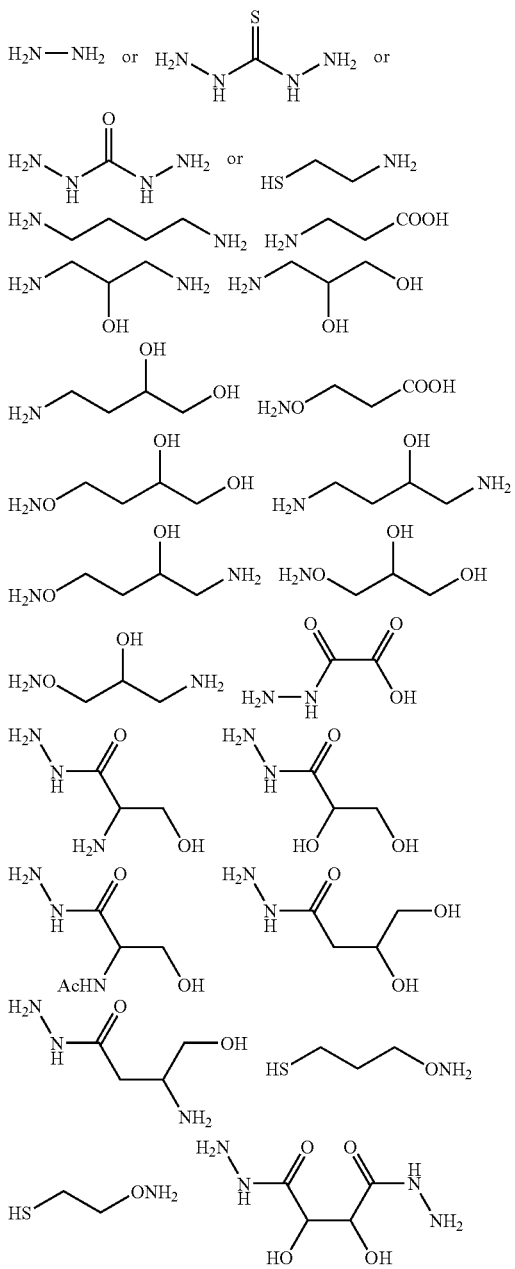

-continued

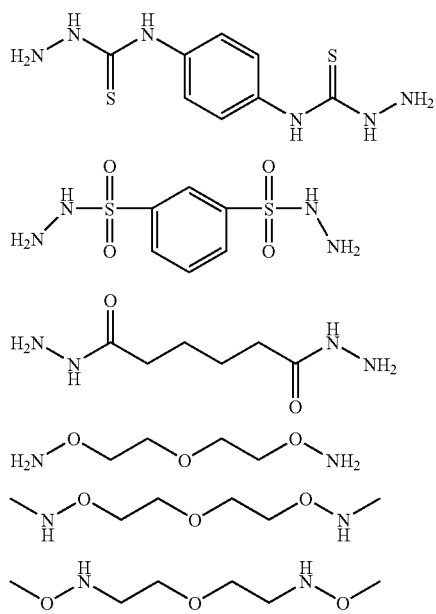

and react the resulting HAS derivative with a second crosslinking compound which is capable of reacting with the HAS derivative and the thio group of the polypeptide. If, e.g., the HAS derivative comprises, as functional group which is reacted with the second crosslinking compound, the structure —NH—, as described above in detail, the following types of second crosslinking compounds with functional groups F1 and F2 are, among others, preferred:

| Type of compound (L) | F1 | F2 |
|---|---|---|
| C | Iodoalkyl | N-succinimide ester |
| D | Bromoalkyl | N-succinimide ester |
| E | Maleimido | N-succinimide ester |
| F | Pydridyldithio | N-succinimide ester |
| G | Vinylsulfone | N-succinimide ester |

Especially preferred examples of the first crosslinking compound are

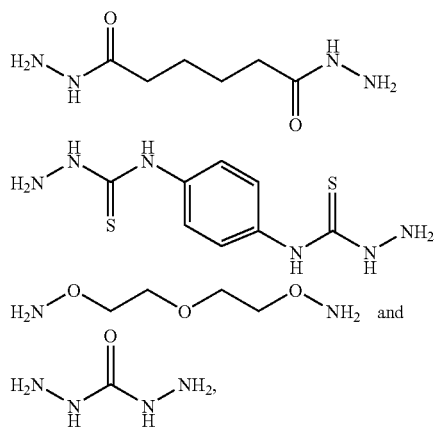

the compounds

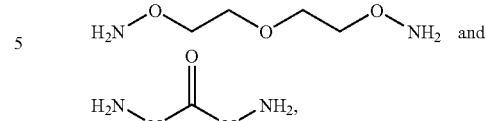

being particularly preferred, and the following second crosslinking compounds

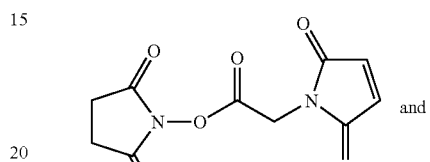

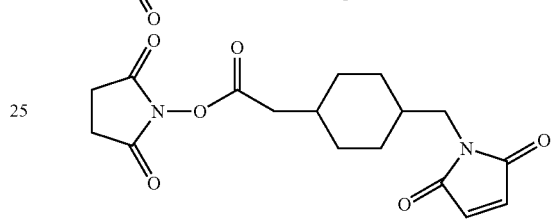

are preferred, the compound

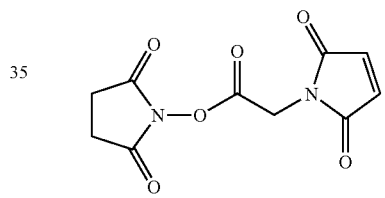

being especially preferred.

Depending on the respective reaction conditions, the solvent or solvent mixture used and/or the residues R' and/or R" of a compound R'—NH—R" the HAS is reacted with in an aqueous medium, it is possible that the hydroxyalkyl starch derivate obtainable by the method or methods described above may have the following constitutions (IIIa):

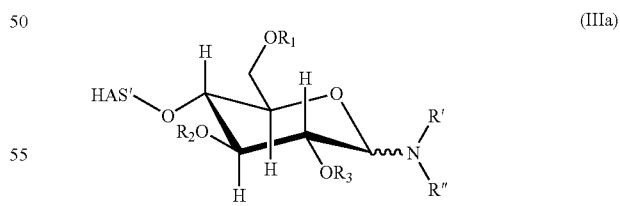

Therefore, the present invention also relates to a hydroxyalkyl starch derivative as described above having a constitution according to formula (IIIa).

It is also possible that, e.g. in the case where R' is hydrogen that the hydroxyalkyl starch derivate obtainable by the method or methods described above may have the following constitutions (IIIa) or (IIIb) where (IIIa) and (IIIb) may be both present in the reaction mixture having a certain equilibrium distribution:

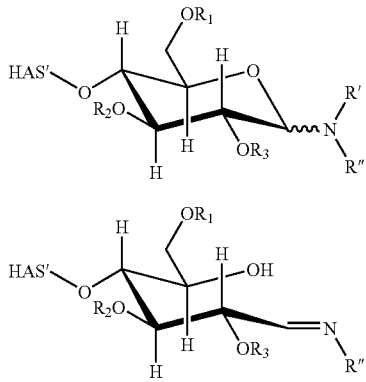

(IIIa)

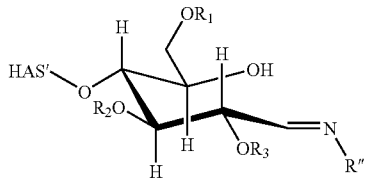

(IIIb)

Therefore, the present invention also relates to a hydroxyalkyl starch derivative as described above having a constitution according to formula (IIIb).

Moreover, the present invention also relates to a hydroxyalkyl starch derivative as described above being present in a mixture of constitutions according to formulae (IIIa) and (IIIb).

Depending on the reaction conditions and/or the chemical nature of the compound R'—NH—R" used for the reaction, the compounds according to formula (IIIa) may be present with the N atom in equatorial or axial position where also a mixture of both forms may be present having a certain equilibrium distribution.

Depending on the reaction conditions and/or the chemical nature of compound R'—NH—R" used for the reaction, the compounds according to formula (IIIb) may be present with the C—N double bond in E or Z conformation where also a mixture of both forms may be present having a certain equilibrium distribution.

In some cases it may be desirable to stabilize the compound according to formula (IIIa). This is especially the case where the compound according to formula (IIIa) is produced and/or used in an aqueous solution. As stabilizing method, acylation of the compound according to formula (IIIa) is particularly preferred, especially in the case where R' is hydrogen. As acylation reagent, all suitable reagents may be used which result in the desired hydroxyalkyl starch derivative according to formula (IVa)

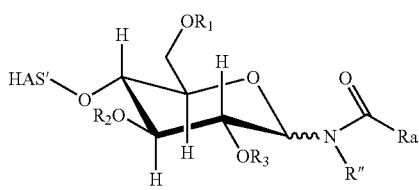

(IVa)

According to especially preferred embodiments of the present invention, the residue Ra being part of the acylation reagent is methyl. As acylation reagents, carboxylic acid anhydrides, carboxylic acid halides and carboxylic acid activated esters are preferably used.

Therefore, the present invention also relates to a hydroxyalkyl starch derivate obtainable by a method as described above wherein said derivative has a constitution according to formula (IVa).

The acylation is carried at a temperature in the range of from 0 to 30° C., preferably in the range of from 2 to 20° C. and especially preferably in the range of from 4 to 10° C.

In other cases it may be desirable to stabilize the compound according to formula (IIIb). This is especially the case where the compound according to formula (IIIb) is produced and/or used in an aqueous solution. As stabilizing method, reduction of the compound according to formula (IIIb) is particularly preferred, especially in the case where R' is hydrogen. As reduction reagent, all suitable reagents may be used which result in the desired hydroxyalkyl starch derivative according to formula (IVb)

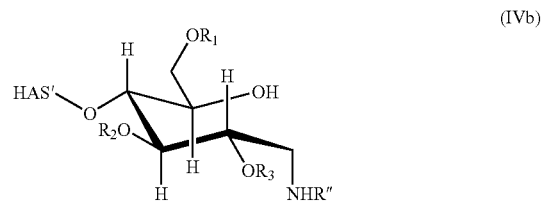

(IVb)

According to especially preferred embodiments of the present invention, as reduction reagents boro hydrides such as $NaCNBH_3$ or $NaBH_4$ are used.

Therefore, the present invention also relates to a hydroxyalkyl starch derivate obtainable by a method as described above wherein said derivative has a constitution according to formula (IVb).

The reduction is carried at a temperature in the range of from 4 to 100° C., preferably in the range of from 10 to 90° C. and especially preferably in the range of from 25 to 80° C.

The present invention further relates to mixtures of compounds (IIIa) and (IIIb), (IVa) and (IVb), (IIIa) and (IVa), (IIIa) and (IVb), (IIIb) and (IVa), (IIIb) and (IVb), (IIIa) and (IIIb) and (IVa), (IIIa) and (IIIb) and (IVb), (IVa) and (IVb) and (IIIa), and (IVa) and (IVb) and (IIIb) wherein (IIIa) and/or (IVa) may be independently present in a conformation where the N atom in equatorial or axial position and/or wherein (IIIb) may be present with the C—N double bond in E or Z conformation.

The invention further relates to a HAS-polypeptide according to the invention for use in a method for treatment of the human or animal body.

Furthermore, the present invention relates to a pharmaceutical composition comprising the HAS-polypeptide of the invention. In a preferred embodiment, the pharmaceutical composition comprises further at least one pharmaceutically acceptable diluent, adjuvant and/or carrier useful in erythropoietin therapy.

The invention further relates to the use of a HAS-polypeptide of the invention for the preparation of a medicament for the treatment of anemic disorders or hematopoietic dysfunction disorders or diseases related hereto.

The invention is further illustrated by the following figures, tables and examples, which are in no way intended to restrict the scope of the present invention.

SHORT DESCRIPTION OF THE FIGURES

FIG. 1

FIG. 1 shows an SDS page analysis of two HES-EPO conjugates
mw: marker
Lane 1: HES-EPO produced according to example protocol 8B: EPO is conjugated to hydrazido-HES 12KD L Lane 2: HES-EPO produced according to example protocol 9B: EPO is conjugated to hydroxylamino HES12KD K
C: control (unconjugated EPO); the upper band represents EPO dimer

FIG. 2

FIG. 2 demonstrates that the HES is conjugated to a carbohydrate moiety of a carbohydrate side chain by showing a digestion of HAS modified EPO forms with polypeptide N-glycosidase Lane 1: HES-EPO produced according to example protocol 8B after digestion with N-glycosidase
Lane 2: HES-EPO produced according to example protocol 9B after digestion with N-glycosidase
Lane 3: BRP EPO standard
Lane 4: BRP EPO standard after digestion with N-glycosidase
mw: marker (Bio-Rad SDS-PAGE Standards Low range Catalog No 161-0305, Bio-Rad Laboratories, Hercules, Calif., USA)

FIG. 3

Figure 3:
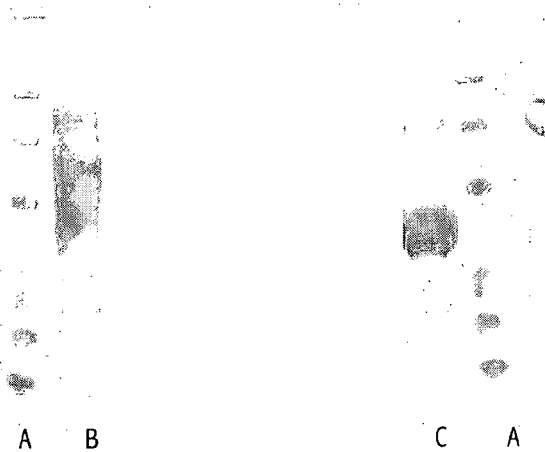

FIG. 3 shows an SDS page analysis of the HES-EPO conjugate, produced according to example 17.1.
Lane A: Protein marker Roti®-Mark PRESTAINED (Carl Roth GmbH+Co, Karlsruhe, D); molecular weights (in kD) of the protein marker from top to bottom: 245, 123, 77, 42, 30, 25.4, and 17.
Lane B: Crude product after conjugation according to example 17.1.
Lane C: EPO starting material.

FIG. 4

Figure 4:

FIG. 4 shows an SDS page analysis of the HES-EPO conjugate, produced according to example 17.3.
Lane A: Crude product after conjugation according to example 17.3.
Lane B: EPO starting material.
Lane C: Protein marker Roti®-Mark PRESTAINED (Carl Roth GmbH+Co, Karlsruhe, D); molecular weights (in kD) of the protein marker from top to bottom: 245, 123, 77, 42, 30, 25.4, and 17.

FIG. 5

Figure 5:
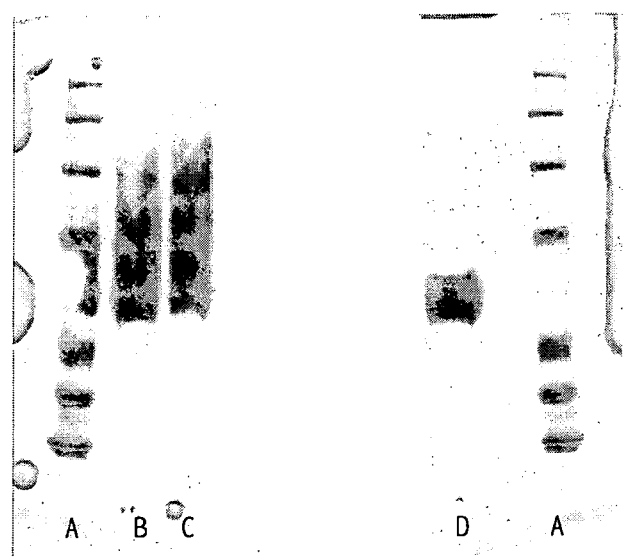

FIG. 5 shows an SDS page analysis of the HES-EPO conjugate, produced according to example 17.4 and 17.5.
Lane A: Protein marker Roti®-Mark PRESTAINED (Carl Roth GmbH+Co, Karlsruhe, D); molecular weights (in kD) of the protein marker from top to bottom: 245, 123, 77, 42, 30, 25.4, and 17.
Lane B: Crude product after conjugation according to example 17.4.
Lane C: Crude product after conjugation according to example 17.5.
Lane D: EPO starting material.

FIG. 6

Figure 6:
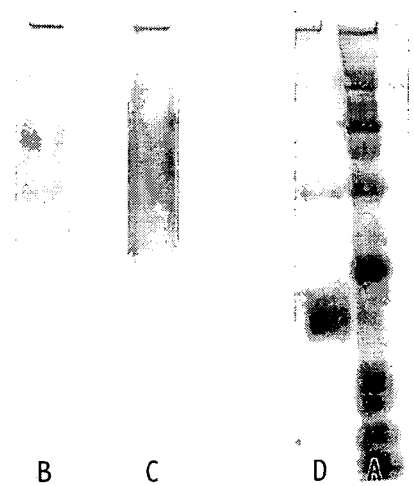

FIG. 6 shows an SDS page analysis of HES-EPO conjugates, produced according to examples 19.1 and 19.4.
Lane A: Protein marker Roti®-Mark PRESTAINED (Carl Roth GmbH+Co, Karlsruhe, D); molecular weights (in kD) of the protein marker from top to bottom: 245, 123, 77, 42, 30, 25.4, and 17.
Lane B: Crude product after conjugation according to example 19.4.
Lane C: Crude product after conjugation according to example 19.1.
Lane D: EPO starting material.

FIG. 7

Figure 7:

FIG. 7 shows an SDS page analysis of HES-EPO conjugates, produced according to examples 19.2, 19.3, 19.5, and 19.6.

Lane A: Protein marker Roti®-Mark PRESTAINED (Carl Roth GmbH+Co, Karlsruhe, D); molecular weights (in kD) of the protein marker from top to bottom: 245, 123, 77, 42, 30, 25.4, and 17.
Lane B: Crude product after conjugation according to example 19.6, based on example 13.3 b)
Lane C: Crude product after conjugation according to example 19.5, based on example 13.1 b).
Lane D: Crude product after conjugation according to example 19.6, based on example 13.3 a).
Lane E: Crude product after conjugation according to example 19.5, based on example 13.1 a).
Lane F: Crude product after conjugation according to example 19.2.
Lane G: Crude product after conjugation according to example 19.3.
Lane K: EPO starting material.

FIG. 8

Figure 8:
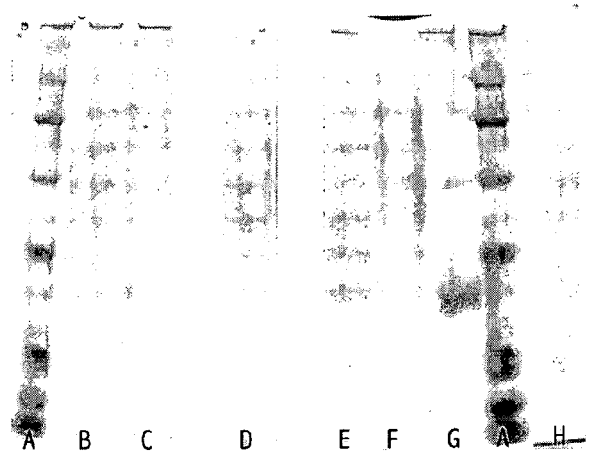

FIG. 8 shows an SDS page analysis of HES-EPO conjugates, produced according to examples 19.7, 19.8, 19.9, 19.10, 19.11, and 19.12.
Lane A: Protein marker Roti®-Mark PRESTAINED (Carl Roth GmbH+Co, Karlsruhe, D); molecular weights (in kD) of the protein marker from top to bottom: 245, 123, 77, 42, 30, 25.4, and 17.
Lane B: Crude product after conjugation according to example 19.11.
Lane C: Crude product after conjugation according to example 19.10.
Lane D: Crude product after conjugation according to example 19.7.
Lane E: Crude product after conjugation according to example 19.8.
Lane F: Crude product after conjugation according to example 19.12.
Lane G: EPO starting material.
Lane K: Crude product after conjugation according to example 19.9.

FIG. 9

SDS-PAGE analyses of EPO-GT-1 subjected to mild acid treatment for 5 min.=lane 2; 10 min.=lane 3; 60 min.=lane 4 and untreated EPO=lane 1; the mobility shift of EPO after removal of N-glycans is shown (+PNGASE).

FIG. 10

HPAEC-PAD pattern of oligosaccharides isolated from untreated EPO and from EPO incubated for 5 min., 10 min. and 60 min. under mild acid hydrolysis conditions. Roman numbers I-V indicate the elution position of I=desialylated diantennary structure, II=trisialylated triantennary structures (two isomers), III=tetrasialylated tetraantennary structure+2 N-acetyllactosamine repeats, IV=tetrasialylated tetraantennary structure+1 N-acetyllactosamine repeat; V=tetrasialylated tetraantennary structure+without N-acetyllactosamine repeat. The elution area of oligosaccharides structures without, with 1-4 sialic acid is indicated by brackets.

FIG. 11

HPAEC-PAD of N-linked oligosaccharides after desialylation; the elution position of N-acetylneuraminic acid is shown; numbers 1-9 indicate the elution position of standard oligosaccharides: 1=diantennary; 2=triantennary (2-4 isomer), 3=triantennary (2-6 isomer); 4=tetraantennary; 5=triantennary plus 1 repeat; 6=tetraantennary plus 1 repeat; 7=triantennary plus 2 repeats; 8=tetraantennary plus 2 repeats and 9=tetraantennary plus 3 repeats.

FIG. 12

SDS-PAGE analysis of mild treated and untreated EPO which were subjected to periodate oxidation of sialic acid residues. 1=periodate oxidized without acid treatment; 2=periodate oxidized 5 min. acid treatment; 3=periodate oxidized and acid treatment 10 min.; 4=periodate oxidized without acid treatment; 5=BRP EPO standard without periodate and without acid treatment.

FIG. 13

HPAEC-PAD pattern of native oligosaccharides isolated from untreated EPO and from EPO incubated for 5 min and 10 min under mild acid hydrolysis conditions and subsequent periodate treatment. The elution area of oligosaccharides structures without and with 1-4 sialic acid is indicated by brackets 1-5.

FIG. 14

SDS-PAGE analysis of the time course of HES-modification of EPO-GT-1-A: 20 µg aliquots of EPO-GT-1-A were reacted with hydroxylamine-modified HES derivative X for 30 min, 2, 4 and 17 hours. Lane 1=30 min reaction time; land 2=2 hour reaction time; land 3=4 hours reaction time; lane 4=17 hours reaction time; lane 5=EPO-GT-1-A without HES-modification. Left figure shows the shift in mobility of EPO-GT-1-A with increasing incubation time in the presence of the with hydroxylamine-modified HES derivative (flow rate: 1 ml·min$^{-1}$) X: Lane 1=30 min reaction time; lane 2=2 hours reaction time; lane 3=4 hours reaction time, land 4=17 hours reaction time; lane 5=EPO-GT-1-A with HES modification. The figure on the right shows analysis of the same samples after their treatment with N-glycosidase.

FIG. 15

SDS-PAGE analysis of Q-Sepharose fractions of HES-EPO conjugates. Each 1% of the flow-through and 1% of the fraction eluting at high salt concentrations were concentrated in a Speed Vac concentrator and were loaded onto the gels in sample buffer. EPO protein was stained by Coomassie Blue. A=sample I; B=sample II; C=sample III; K=control EPO-GT-1; A1, B1, C1 and K1 indicated the flow-through fraction; A2, B2, C2 and K2 indicates the fraction eluted with high salt concentration.

FIG. 16a

SDS-PAGE analysis of HES-modified EPO sample A2 (see FIG. 15), control EPO sample K2 and EPO-GT-1-A EPO preparation were digested in the presence of N-glycosidase in order to remove N-linked oligosaccharides. All EPO samples showed the mobility shift towards low molecular weight forms lacking or containing O-glycan. A lower ratio of the O-glycosylated and nonglycosylated protein band was observed for the HES-modified EPO sample A2 after de-N-glycosylation and a diffuse protein band was detected around 30 KDa, presumably representing HES-modification at the sialic acid of O-glycan residue (see arrow marked by an asterisk).

FIG. 16b

Figure 15:
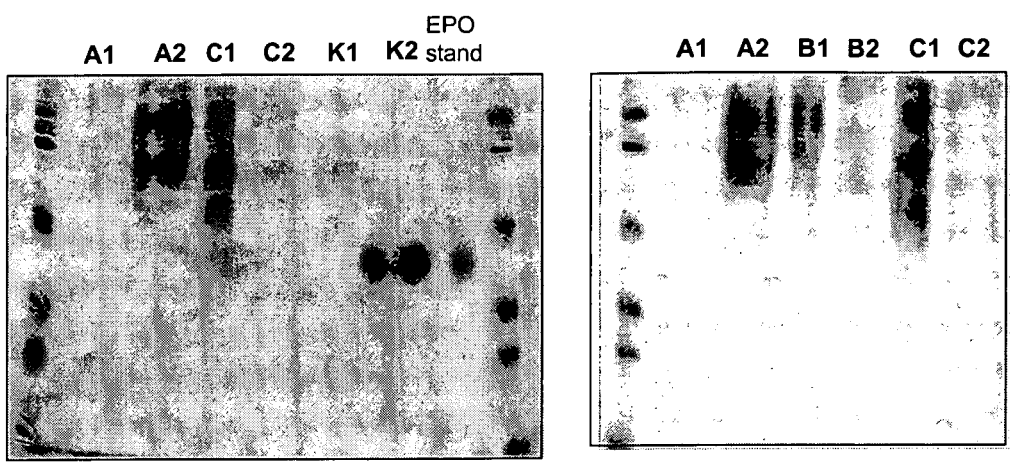
Figure 16A:
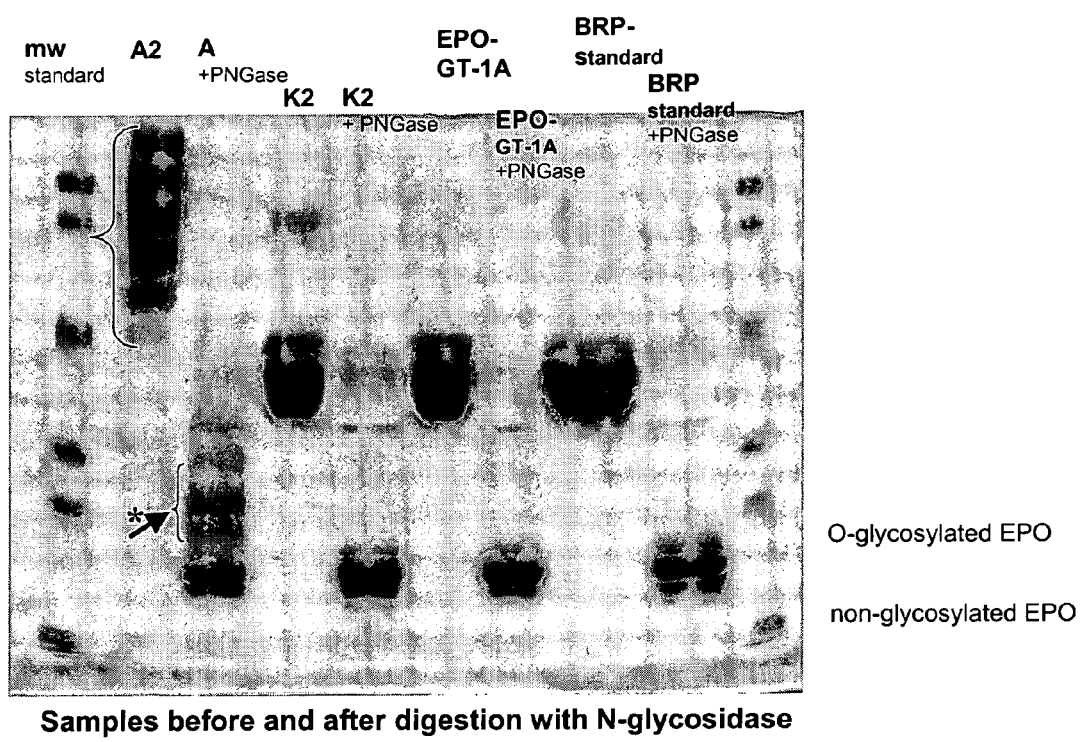

SDS-PAGE analysis after mild hydrolysis of HES-modified EPO sample A2 (see FIG. 15), control EPO sample K2 and EPO-GT-1A which were untreated or digested in the presence of N-glycosidase in order to remove N-linked oligosaccharides (see FIG. 16a). Both high molecular weight form of A2 before and A after N.glycosidase treatment (see brackets with and without arrow) disappeared upon acid treatment of the samples. The BRP EPO standard which was run for comparison was not subjected to mild acid treatment.

FIG. 17

HPAEC-PAD analysis of N-linked oligosaccharide material liberated from HES-modified sample A, from EPO-GT-1-A and from a control EPO sample incubated with unmodified HES (K). Roman numbers I-V indicate the elution position of I=disialylated diantennary structure, II=trisialylated triantennary structures (two isomers), III=tetrasialylated tetraantennary structure+2 N-acetyllactosamine repeats, IV=tetrasialylated tetraantennary structure+1 N-acetyllactosamine repeat, V=tetrasialylated tetraantennary structure+without N-acetyllactosamine repeat; brackets indicate the elution area of di-, tri- and tetrasialylated N-glycans as reported in the legends of FIGS. 10 and 13.

FIG. 18

HPAEC-PAD analysis of N-linked oligosaccharide material liberated from HES-modified sample A, from EPO-GT-1A and from a control EPO sample (K) incubated with unmodified HES. The retention times of a mixture of standard oligosaccharides is shown: numbers 1-9 indicate the elution position of standard oligosaccharides: 1=diantennary; 2=triantennary (2-4 isomer); 3=triantennary (2-6 isomer); 4=tetraantennary; 5=triantennary plus 1 repeat; 6=tetraantennary plus 1 repeat; 7=triantennary plus 2 repeats; 8=tetraantennary plus 2 repeats and 9=tetraantennary plus 3 repeats.

FIGS. 19 to 25

FIGS. 19 to 25 represent MALDI/TOF mass spectra of the enzymatically liberated and chemically desialylated N-glycans isolated from HES-modified EPO and control EPO preparations. Major signals at m/z 1809.7, 2174.8, 2539.9, 2905.0 and 3270.1 ([M+Na]$^+$) correspond to di- to tetraantennary complex-type N-glycan structures with no, one or two N-acetyllactosamine repeats accompanied by weak signals due to loss of fucose or galactose which are due to acid hydrolysis conditions employed for the desialylation of samples for MS analysis.

FIG. 19

MALDI/TOF spectrum: desialylated oligosaccharides of HES-modified EPO A2.

FIG. 20

MALDI/TOF spectrum: desialylated oligosaccharides of EPO GT-1-A.

FIG. 21

MALDI/TOF spectrum: desialylated oligosaccharides of EPO K2.

FIG. 22

MALDI/TOF spectrum: desialylated oligosaccharides of EPO-GT-1.

FIG. 23

MALDI/TOF spectrum: desialylated oligosaccharides of EPO-GT-1 subjected to acid hydrolysis for 5 min.

FIG. 24

MALDI/TOF spectrum: desialylated oligosaccharides of EPO-GT-1 subjected to acid hydrolysis for 10 min.

FIG. 25

MALDI/TOF spectrum: desialylated oligosaccharides of EPO-GT-1 subjected to acid hydrolysis for 60 min.

EXAMPLES

Example 1

Production of Recombinant EPO

A) Production in Mammalian Cells

Recombinant EPO was produced in CHO cells as follows
A plasmid harbouring the human EPO cDNA was cloned into the eukaryotic expression vector (pCR3 and named afterwards pCREPO). Site directed mutagenesis was performed using standard procedures as described (Grabenhorst, Nimtz, Costa et al., 1998, In vivo specificity of human alpha 1,3/4-fucosyltransferases III-VII in the biosynthesis of Lewis(x)

and sialyl Lewis(x) motifs on complex-type N-glycans-Co-expression studies from BHK-21 cells together with human beta-trace protein, J. Biol. Chem., 273(47), 30985-30994).

CHO cells stably expressing human EPO or amino acid variants (e.g. Cys-29→Ser/Ala, or Cys-33→Ser/Ala, Ser-126→Ala etc.) thereof were generated with the calcium phosphate precipitation method and selected with G418-sulfate as described (Grabenhorst et al.). Three days after transfection, the cells were subcultivated 1:5 and selected in DMEM containing 10% FBS and 1.5 g/liter G418 sulfate.

Using this selection procedure, usually 100-500 clones survived and where propagated in selection medium for a further time period of 2-3 weeks. Cell culture supernatants of confluently growing monolayers were then analyzed for EPO expression levels by Western blot analysis and by IEF/Western Blot analysis.

EPO was produced from stable subclones in spinner flasks or in 21 perfusion reactors. Different glycoforms of EPO with different amounts of NeuAc (e.g. 2-8, 4-10, 8-12 NeuAc residues) were isolated according to published protocols using combinations various chromatographic procedures as described below.

Literature:

Grabenhorst, Conradt, 1999, The cytoplasmic, transmembrane, and stem regions of glycosyltransferases specify their in vivo functional sublocalization and stability in the Golgi., J Biol. Chem., 274(51), 36107-16; Grabenhorst, Schlenke, Pohl, Nimtz, Conradt, 1999, Genetic engineering of recombinant glycoproteins and the glycosylation pathway in mammalian host cells, Glycoconj J., 16(2), 81-97; Mueller, Schlenke, Nimtz, Conradt, Hauser, 1999, Recombinant glycoprotein product quality in proliferation-controlled BHK-21 cells, Biotechnology and bioengineering, 65(5), 529-536; Schlenke, Grabenhorst, Nimtz, Conradt, 1999, Construction and characterization of stably transfected BHK-21 cells with human-type sialylation characteristic, Cytotechnology, 30(1-3), 17-25.

B) Production in Insect Cells

Recombinant human EPO is produced from insect cell lines SF9 and SF 21 after infection of cells with recombinant baculovirus vector containing the human EPO cDNA under control of the polyhedrin promoter as described in the literature.

Cells grown in serum-free culture medium are infected at cell density of $2\times10^6$ or $\times10^7$ cells per mL and EPO titers are determined every day in the cell culture supernatants. EPO is purified by Blue sepharose chromatography, ion-exchange chromatography on Q-Sepharose and finally RP-HPLC on $C_4$-Phase.

Purity of the product is checked by SDS-PAGE and N-terminal sequencing. Detailed carbohydrate structural analysis (N- and O-glycosylation) may be performed according to published procedures.

Literature:

Grabenhorst, Hofer, Nimtz, Jager, Conradt, 1993, Biosynthesis and secretion of human interleukin 2 glycoprotein variants from baculovirus-infected Sf21 cells. Characterization of polypeptides and posttranslational modifications, Eur J. Biochem., 215(1), 189-97; Quelle, Caslake, Burkert, Wojchowski, 1989, High-level expression and purification of a recombinant human erythropoietin produced using a baculovirus vector, Blood, 74(2), 652-7

Example 2A

Formation of Reactive HES Derivatives

1. SH-Reactive HES 1.1 Reaction of EMCH with Oxo-HES12KD to form SH-Reactive HES12KD B 0.144 g (0.012 mmol) of Oxo-HES12KD (Fresenius German Patent DE 196 28 705 A1)

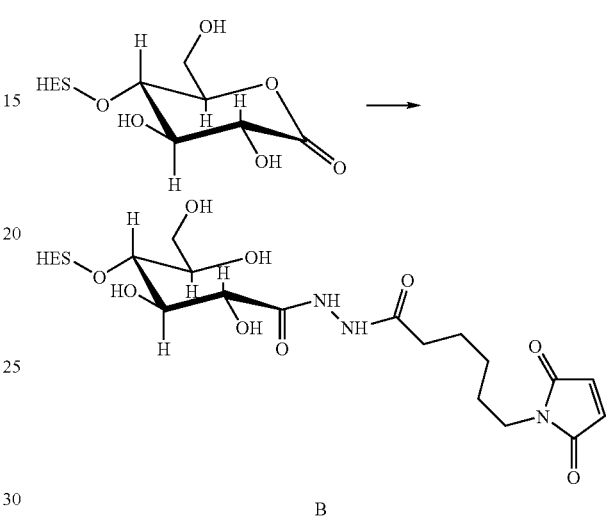

B are dissolved in 0.3 mL absolute dimethyl sulfoxide (DMSO) and are added dropwise under nitrogen to a mixture of 34 mg (0.15 mmol) EMCH (Perbio Science, Deutschland GmbH, Bonn, Germany) in 1.5 mL DMSO. After stirring for 19 h at 60° C. the reaction mixture is added to 16 mL of a 1:1 mixture of ethanol and acetone. The precipitate is collected by centrifugation, redissolved in 3 mL DMSO and again precipitated as described. The SH-reactiv-HES12KD B is obtained by centrifugation and drying in vaccuo. The conjugation reaction with Thio-EPO is described in Example 3, 2.2.

Alternatives:

In this reaction, all cross-linkers can be used, which exhibit a hydrazide- and a maleimide function, separated by a spacer. Further examples for molecules of that group; available from Perbio Science, Deutschland GmbH, Bonn, Germany, are shown in table 2; marked with an "A". Furthermore, another group of cross-linkers exhibiting an activated disulfide function instead of a maleimide function could also be used.

1.2 Halogenacetamide-derivatives of HES Glycosylamines a) Glycosylamine-Formation 1

[1] Manger, Wong, Rademacher, Dwek, 1992, Biochemistry, 31, 10733-10740; Manger, Rademacher, Dwek, 1992, Biochemistry, 31, 10724-10732

A 1 mg sample of HES12KD is dissolved in 3 mL of saturated ammonium bicarbonate. Additional solid ammonium bicarbonate is then added to maintain saturation of the solution during incubation for 120 h at 30° C. The Amino-HES12KD C is desalted by direct lyophilization of the reaction mixture.

b) Acylation of the Glycosylamine C with Chloroacetic Acid Anhydride

A 1 mg sample of Amino-HES12KD C is dissolved in 1 mL of 1 M sodium bicarbonate and cooled on ice. To this is added a crystal of solid chloroacetic acid anhydride (~5 mg), and the reaction mixture is allowed to warm to room temperature. The pH is monitored and additional base is added if the pH dropped below 7.0. After two hours at room temperature a second aliquot of base and anhydride is added. After six hours the product Chloroacetamide-HES D1 (X=Cl) is desalted by passage over a mixed bed Amberlite MB-3(H)(OH) ion exchange resins.

c) Acylation of the Glycosylamine with Bromoacetic Anhydride[2]

[2] Black, Kiss, Tull, Withers, 1993, *Carbohydr. Res.*, 250, 195

Bromoacetic anhydride is prepared as described by Thomas.[3] A 1 mg sample of amino-HES12KD C is dissolved in 0.1 mL of dry DMF and cooled on ice and 5 mg bromoacetic anhydride is added. The reaction mixture is brought slowly to room temperature and the solution is stirred for 3 h. The reaction mixture is added to 1 mL of a 1:1 mixture of ethanol and acetone with −20° C. The precipitate is collected by centrifugation, redissolved in 0.1 mL DMF and again precipitated as described. The Bromoacetamide-HES D2 (X=Br) is obtained by centrifugation and drying in vaccuo. The conjugation reaction with Thio-EPO is described in Example 3, 1.2.

[3] Thomas, 1977, *Methodes Enzymol.*, 46, 362 d) The corresponding Iodo-derivative D3 (X=I) is synthesised as described for D2.

Instead bromoacetic anhydride N-succinimidyl iodoacetate is used and all steps are performed in the dark.

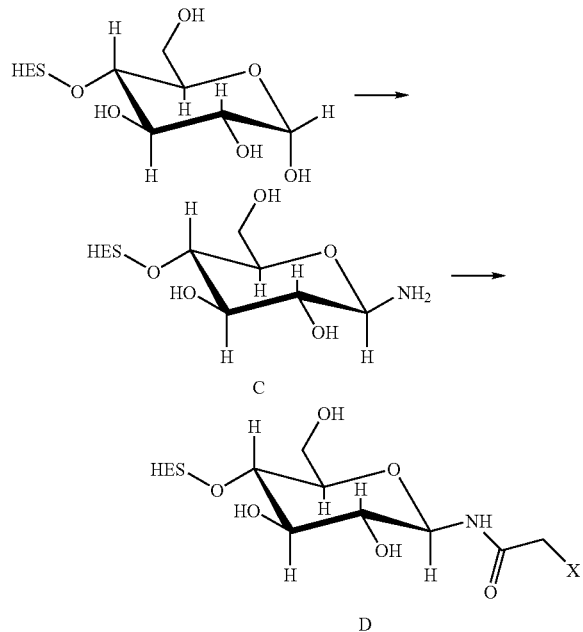

Alternatives:

For acylation of amino groups, other activated forms of halogen acidic acids can be used, e.g.
  -bromides or -chlorides
    esters, e.g. N-hydroxysuccinimide ester, esters with substituted phenoles (p-nitrophenole, pentafluorophenole, trichlorophenole etc)

Furthermore, all cross-linkers having an amino reactive group and a halogen acetyl function, separated by a spacer, could be used. An example thereof is SBAP. This molecule and others are available from Perbio Science Deutschland GmbH, Bonn, Germany. They are marked in table 2 with an "D". For the use as cross-linkers for the ligation of amino-HES with thio-EPO without isolation of the halogenacetamide-HES derivatives see remarks in example 3, 1.2.

1.3 Halogenacetamide-Derivatives of Amino-HES E[1]

a) Reaction of 1,4-diaminobutane with Oxo-HES12KD to amino-HES12KD E[4]

[4] S. Frie, Diplomarbeit, Fachhochschule Hamburg, 1998

1.44 g (0.12 mmol) of Oxo-HES12KD are dissolved in 3 mL dry dimethyl sulfoxide (DMSO) and are added dropwise under nitrogen to a mixture of 1.51 mL (15 mmol) 1,4-diaminobutane in 15 mL DMSO. After stirring for 19 h at 40° C. the reaction mixture is added to 160 mL of a 1:1 mixture of ethanol and acetone. The precipitate Amino-HES12KD E is collected by centrifugation, redissolved in 40 mL of water an dialysed for 4 days against water (SnakeSkin dialysis tubing, 3.5 KD cut off, Perbio Science Deutschland GmbH, Bonn, Germany) and lyophilized.

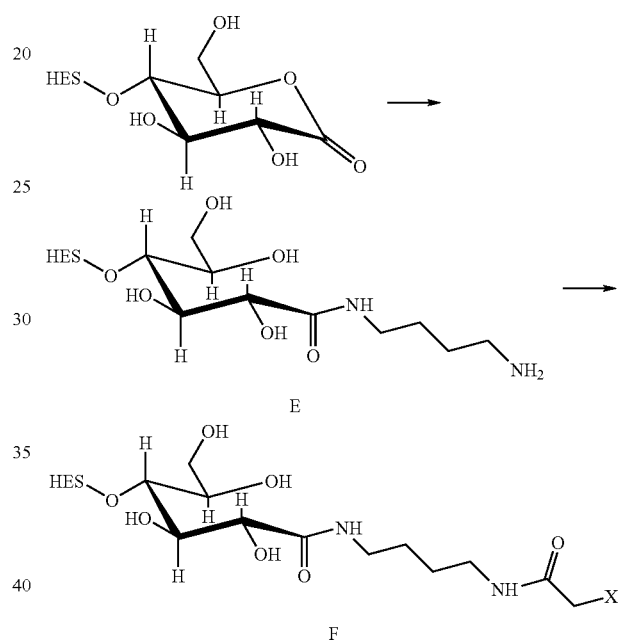

b) Chloroacetamide-HES12KD F1 is prepared as described for Chloroacetamide-HES12KD D1 in 1.3 above.

c) Bromoacetamide-HES12KD F2 (X=Br) is prepared as described for Bromoacetamide-HES12KD D2 in 1.3 above. The conjugation reaction with Thio-EPO is described in Example 3, 1.2.

d) The corresponding Iodo-derivative F3 (X=I) is not isolated before its reaction with Thio-EPO. The experiment is described in Example 3, 1.1.

Alternatives:

See 1.2 above

2. CHO-Reactive HES 2.1 Hydrazide-HES a) Reaction of Hydrazine with Oxo-HES12KD

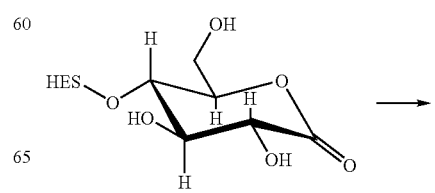

-continued

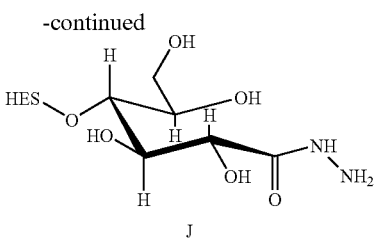

J 1.44 g (0.12 mmol) of Oxo-HES12KD are dissolved in 3 mL absolute dimethyl sulfoxide (DMSO) and are added dropwise under nitrogen to a mixture of 0.47 mL (15 mmol) hydrazine in 15 mL DMSO. After stirring for 19 h at 40° C. the reaction mixture is added to 160 mL of a 1:1 mixture of ethanol and acetone. The precipitated product J is collected by centrifugation, redissolved in 40 mL of water and dialysed for 2 days against a 0.5% (v/v) triethylamine in water solution and for 2 days against water (SnakeSkin dialysis tubing, 3.5 KD cut off, Perbio Science Deutschland GmbH, Bonn, Germany) and lyophilized. The conjugation reaction with oxidised Glyco-EPO is described in Example 4, 2.2.

b) Reaction of Adipic Dihydrazide with Oxo-HES12KD

L 1.74 g (15 mmol) adipic dihydrazide are dissolved in 20 mL absolute dimethyl sulfoxide (DMSO) at 65° C. and 1.44 g (0.12 mmol) of Oxo-HES12KD, dissolved in 3 mL absolute DMSO are added dropwise under nitrogen. After stirring for 68 h at 60° C. the reaction mixture is added to 200 mL of water The solution containing L is dialysed for 2 days against a 0.5% (v/v) triethylamine in water solution and for 2 days against water (SnakeSkin dialysis tubing, 3.5 KD cut off, Perbio Science Deutschland GmbH, Bonn, Germany) and lyophilized. The conjugation reaction with oxidised Glyco-EPO is described in Example 4, 2.2.

Alternatives:

Furthermore, derivatives can be used, wherein 2 hydrazide groups are separated by any spacer.

3. Further Amino-HES12KD derivatives I and H [1]

Ammonolysis of D or F is performed separately by dissolving a 1 mg sample of each halogenacetamide in 0.1 mL of saturated ammonium carbonate. Additional solid ammonium carbonate is then added to maintain saturation of the solution during incubation of 120 h at 30° C. The reaction mixture is added to 1 mL of a 1:1 mixture of ethanol and acetone with −20° C. The precipitate is collected by centrifugation, redissolved in 0.05 mL water and again precipitated as described.

The product amino-HES H or I is obtained by centrifugation and drying in vaccuo. The conjugation reaction with oxidised Glyco-EPO is described in Example 4, 4.1.

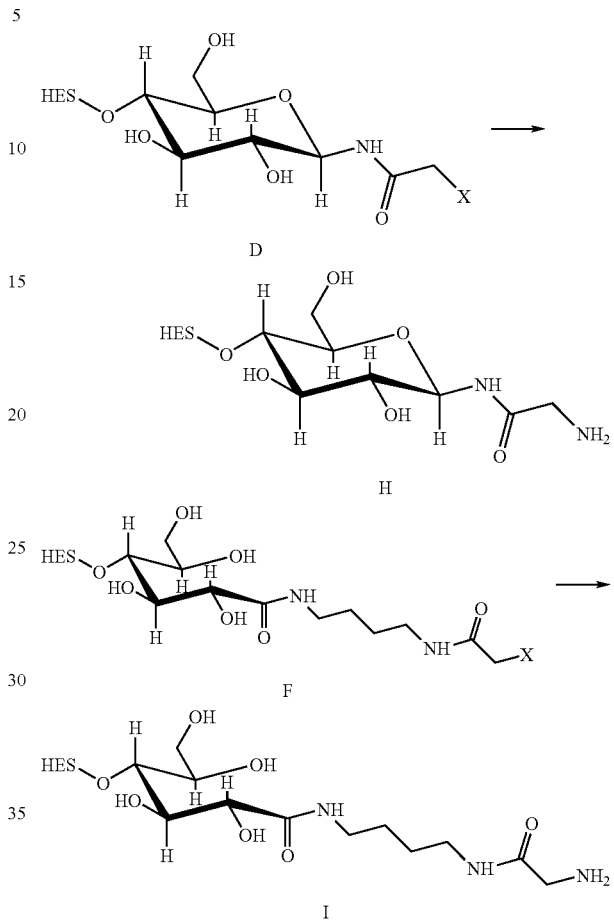

4. Hydroxylamine-Modified HES12KD K

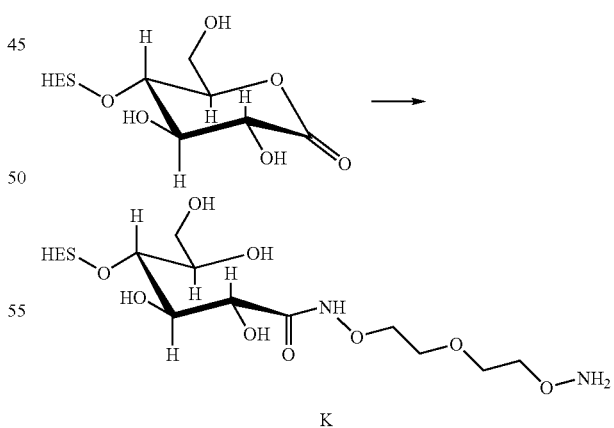

K

O-[2-(2-aminooxy-ethoxy)-ethyl]-hydroxylamine is synthesized as described by Boturyn et al in 2 steps from commercially available materials.[5] 1.44 g (0.12 mmol) of Oxo-HES12KD are dissolved in 3 mL absolute dimethyl sulfoxide (DMSO) and are added dropwise under nitrogen to a mixture of 2.04 g (15 mmol) O-[2-(2-aminooxy-ethoxy)-ethyl]-hydroxylamine in 15 mL DMSO. After stirring for 48 h at 65° C. the reaction mixture is added to 160 mL of a 1:1 mixture of ethanol and acetone. The precipitated product K is collected by centrifugation, redissolved in 40 mL of water and dialysed for 4 days against water (SnakeSkin dialysis tubing, 3.5 KD cut off, Perbio Science Deutschland GmbH, Bonn, Germany) and lyophilized. The conjugation reaction with oxidised Glyco-EPO is described in Example 4, 3.1.

[5]Boturyn, Boudali, Constant, Defrancq, Lhomme, 1997, *Tetrahedron*, 53, 5485

Alternatives:

Furthermore, derivatives could be used, wherein the two hydroxylamine groups are separated by any spacer.

5. Thio-HES12KD 5.1 Addition to Oxo-HES12KD

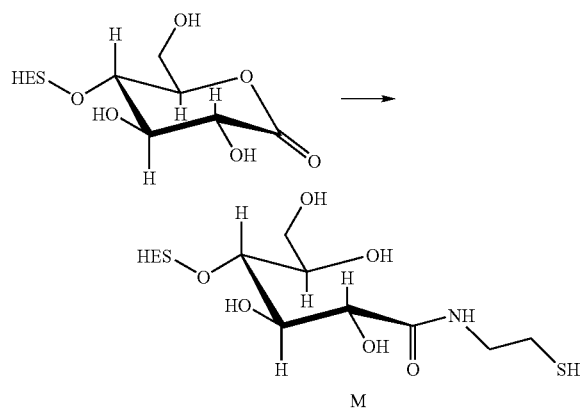

1.44 g (0.12 mmol) of Oxo-HES12KD are dissolved in 3 mL absolute dimethyl sulfoxide (DMSO) and are added to a mixture of 1.16 g (15 mmol) cysteamine in 15 mL DMSO under nitrogen dropwise. After stirring for 24 h at 40° C. the reaction mixture is added to 160 mL of a 1:1 mixture of ethanol and acetone. The precipitated product M is collected by centrifugation, redissolved in 40 mL of water and dialysed for 2 days against a 0.5% (v/v) triethylamine in water solution and for 2 days against water (SnakeSkin dialysis tubing, 3.5 KD cut off, Perbio Science Deutschland GmbH, Bonn, Germany) and lyophilized. The conjugation reaction with oxidised Glyco-EPO is described in Example 4, 2.1.

Alternatives:

Derivatives could be used, wherein the amino group and the thio-function are separated by any spacer. Furthermore, the amino group in the derivatives could be replaced by a hydrazine, a hydrazide or a hydroxylamine. The thio-function could be protected in the form of e.g. a disulfide or a trityl-derivative. However, in this case, a further deprotection step must be preformed before the conjugation, which would release a component being analogous to M.

5.2 Modification of Amino-HES12KD E, H or I a) Modification with SATA/SATP 1.44 g (0.12 mmol) of Amino-HES12KD E, H or I are dissolved in 3 mL absolute dimethyl sulfoxide (DMSO) and are added to a mixture of 139 mg (0.6 mmol) SATA in 5 mL DMSO under nitrogen dropwise. After stirring for 24 h at room temperature the reaction mixture is added to 160 mL of a 1:1 mixture of ethanol and acetone. The precipitated product N is collected by centrifugation, redissolved in 40 mL of water and dialysed for 2 days against water (SnakeSkin dialysis tubing, 3.5 KD cut off, Perbio Science Deutschland GmbH, Bonn, Germany) and lyophilized.

The deprotection is performed in a 50 mM sodium phosphate buffer, containing 25 mM EDTA and 0.5M hydroxylamine, pH7.5 for 2 hours at room temperature and the product O is purified by dialysis against a 0.1 M sodium acetate buffer pH 5.5, containing 1 mM EDTA. The deprotection reaction is performed immediately before the conjugation reaction which is described in Example 4, 2.1.

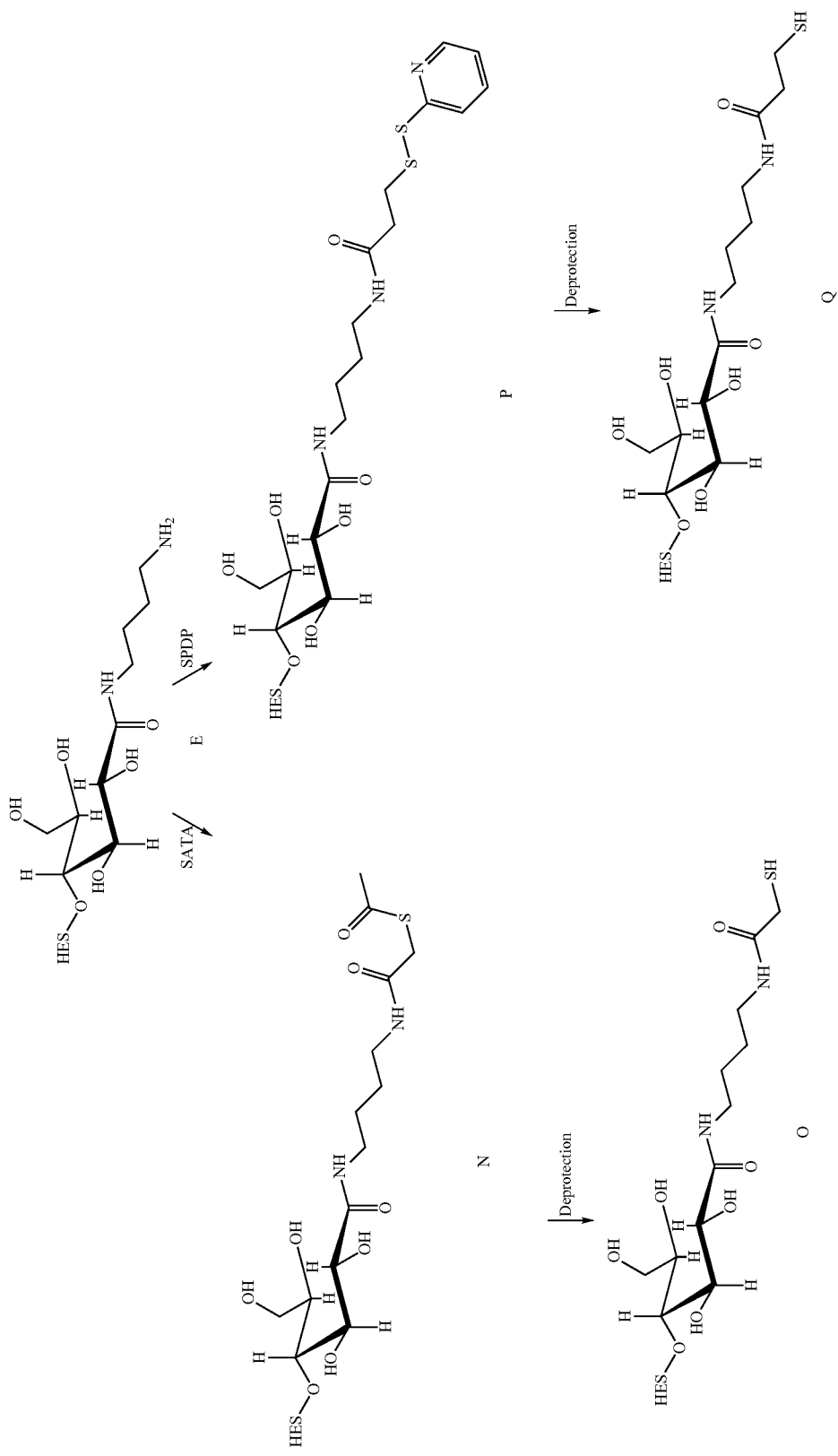

b) Modification with SPDP 1.44 g (0.12 mmol) of Amino-HES12KD E, H or I are dissolved in 3 mL absolute dimethyl sulfoxide (DMSO) and are dropwise added to a mixture of 187 mg (0.6 mmol) SPDP in 5 mL DMSO under nitrogen. After stirring for 24 h at room temperature the reaction mixture is added to 160 mL of a 1:1 mixture of ethanol and acetone. The precipitated product P is collected by centrifugation, redissolved in 40 mL of water and dialysed for 2 days against water (SnakeSkin dialysis tubing, 3.5 KD cut off, Perbio Science Deutschland GmbH, Bonn, Germany) and lyophilized.

The deprotection is performed in a solution of 12 mg dithiothreitol (DTT) per 0.5 mL 100 mM sodium acetate buffer, containing 100 mM sodium chloride at pH 4.5 for 30 min at room temperature and the product Q was purified by dialysis against a 0.1 M sodium acetate buffer pH 5.5, containing 1 mM EDTA. The deprotection reaction is performed immediately before the conjugation reaction which is described in Example 4, 2.1.

Alternatives:

For the conversion of amino- to thiol-groups, either in free form or protected, several reagents are available. After the modification, the products could be isolated. Alternatively, as accepted for the use of cross-linkers, they could be directly used for the conjugation reaction, preferably after a purification step. For the isolation and storage of thio-HES derivatives, the synthesis of thio-HES derivatives in a protected form may be useful. For this, all derivatives being analogous to SATA could be used, which have an active ester-function and a thioester-function, separated by any spacer. SATP, being a further member of this group, is found in table 2, marked with an "H". The derivatives being analogous to SPDP could have an active ester-function and a disulfide-function, separated by any spacer. Further members of these groups are found in table 2, marked with an "F". Further analogous derivatives could have an active ester-function and a thiol-function, protected as a trityl derivative, separated by any spacer.

Example 2B

Formation of Reactive HES Derivatives

1. Halogenacetamide-Derivatives of Amino-HES E [1]

Reaction of 1,4-diaminobutane with Oxo-HES18KD to amino-HES18KD E[6]

[6]S. Frie, Diplomarbeit, Fachhochschule Hamburg, 1998

1.44 g (0.12 mmol) of Oxo-HES18KD were dissolved in 3 mL dry dimethyl sulfoxide (DMSO) and were added dropwise under nitrogen to a mixture of 1.51 mL (15 mmol) 1,4-diaminobutane in 15 mL DMSO. After stirring for 19 h at 40° C. the reaction mixture was added to 160 mL of a 1:1 mixture of ethanol and acetone. The precipitate Amino-HES18KD E was collected by centrifugation, redissolved in 40 mL of water an dialysed for 4 days against water (Snake-Skin dialysis tubing, 3.5 KD cut off, Perbio Science Deutschland GmbH, Bonn, Germany) and lyophilized.

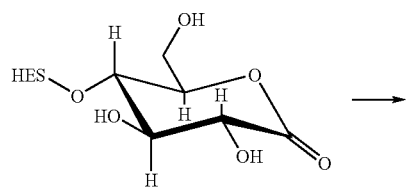

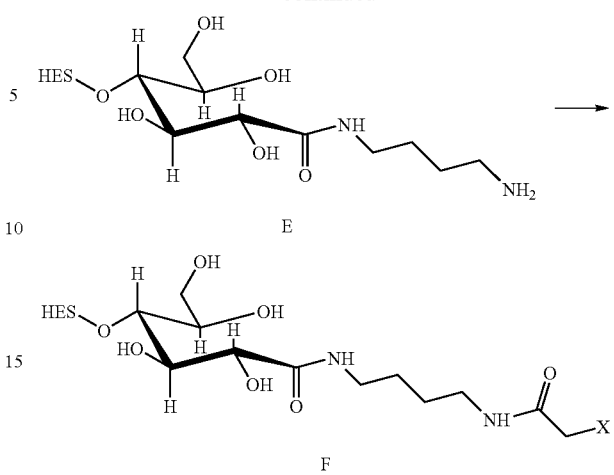

2. CHO-Reactive HES a. Hydrazide-HES a) Reaction of Hydrazine with Oxo-HES18KD

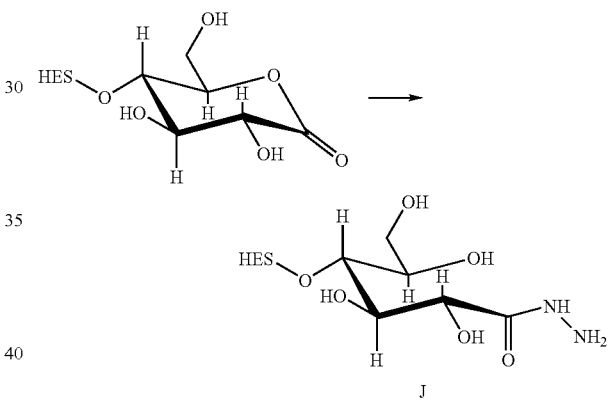

1.44 g (0.12 mmol) of Oxo-HES18KD were dissolved in 3 mL absolute dimethyl sulfoxide (DMSO) and were added dropwise under nitrogen to a mixture of 0.47 mL (15 mmol) hydrazine in 15 mL DMSO. After stirring for 19 h at 40° C. the reaction mixture was added to 160 mL of a 1:1 mixture of ethanol and acetone. The precipitated product J was collected by centrifugation, redissolved in 40 mL of water and dialysed for 2 days against a 0.5% (v/v) triethylamine in water solution and for 2 days against water (SnakeSkin dialysis tubing, 3.5 KD cut off, Perbio Science Deutschland GmbH, Bonn, Germany) and lyophilized. The conjugation reaction with oxidised Glyco-EPO is described in Example 4, 2.2.

b) Reaction of Adipic Dihydrazide with Oxo-HES18KD

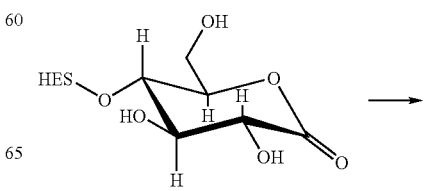

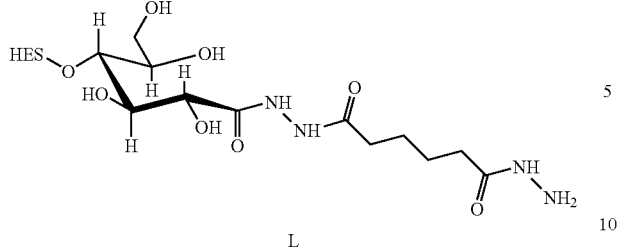

L 1.74 g (15 mmol) adipic dihydrazide were dissolved in 20 mL absolute dimethyl sulfoxide (DMSO) at 65° C. and 1.44 g (0.12 mmol) of Oxo-HES18KD, dissolved in 3 mL absolute DMSO were added dropwise under nitrogen. After stirring for 68 h at 60° C. the reaction mixture was added to 200 mL of water The solution containing L was dialysed for 2 days against a 0.5% (v/v) triethylamine in water solution and for 2 days against water (SnakeSkin dialysis tubing, 3.5 KD cut off, Perbio Science Deutschland GmbH, Bonn, Germany) and lyophilized. The conjugation reaction with oxidised Glyco-EPO is described in Example 4, 2.2.

3. Hydroxylamine-Modified HES18KD K

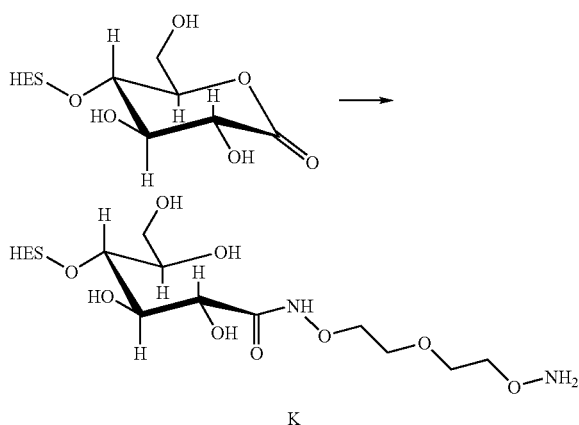

K

O-[2-(2-aminooxy-ethoxy)-ethyl]-hydroxylamine was synthesized as described by Boturyn et al in 2 steps from commercially available materials.[7] 1.44 g (0.12 mmol) of Oxo-HES18KD were dissolved in 3 mL absolute dimethyl sulfoxide (DMSO) and were added dropwise under nitrogen to a mixture of 2.04 g (15 mmol) O-[2-(2-aminooxy-ethoxy)-ethyl]-hydroxylamine in 15 mL DMSO. After stirring for 48 h at 65° C. the reaction mixture was added to 160 mL of a 1:1 mixture of ethanol and acetone. The precipitated product K was collected by centrifugation, redissolved in 40 mL of water and dialysed for 4 days against water (SnakeSkin dialysis tubing, 3.5 KD cut off, Perbio Science Deutschland GmbH, Bonn, Germany) and lyophilized. The conjugation reaction with oxidised Glyco-EPO is described in Example 4, 3.1.

[7]Boturyn, Boudali, Constant, Defrancq, Lhomme, 1997, *Tetrahedron*, 53, 5485

4. Thio-HES18KD a. Addition to Oxo-HES18KD

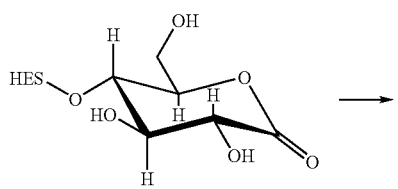

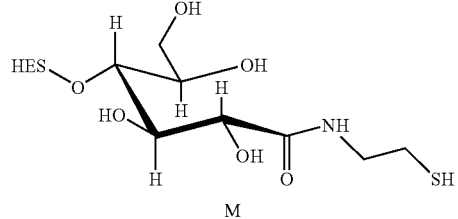

M 1.44 g (0.12 mmol) of Oxo-HES18KD were dissolved in 3 mL absolute dimethyl sulfoxide (DMSO) and were added to a mixture of 1.16 g (15 mmol) cysteamine in 15 mL DMSO under nitrogen dropwise. After stirring for 24 h at 40° C. the reaction mixture was added to 160 mL of a 1:1 mixture of ethanol and acetone. The precipitated product M was collected by centrifugation, redissolved in 40 mL of water and dialysed for 2 days against a 0.5% (v/v) triethylamine in water solution and for 2 days against water (SnakeSkin dialysis tubing, 3.5 KD cut off, Perbio Science Deutschland GmbH, Bonn, Germany) and lyophilized. The conjugation reaction with oxidised Glyco-EPO is described in Example 4, 2.1.

Example 3

Conjugation Reactions with Thio-EPO

1. Reaction of Thio-EPO with a Halogenacetamide-Modified SH-Reactive HES 1.1 Example Protocol 1

Conjugation of ThioEPO to Amino-HES12KD (E, H or I) with a Cross-Linker Containing a NHS-Active-Ester and an Iodoacetamide Group, e.g. SIA.[8]

[8]Cumber, Forrester, Foxwell, Ross, Thorpe, 1985, *Methods Enzymol.*, 112, 207

Materials

A. Borate buffer. Composition is 50 mM sodium borate, pH 8.3, 5 mM EDTA.

B. PBS, phosphate buffered saline: 10 mM sodium phosphate, 150 mM NaCl, pH 7.4.

C. AminoHES12KD E, H or I. Prepared at 1 mg/mL in borate buffer.

D. Crosslinker stock solution: 14 mg SIA were dissolved in 1 mL DMSO

E. D-Salt™ Dextran Desalting Columns, 2×5 mL bed volume (Perbio Science Deutschland GmbH, Bonn, Germany)

F. Coomassie® Protein Assay Reagent (Perbio Science Deutschland GmbH, Bonn, Germany)

G. ThioEPO solution: 5 mg/mL of ThioEPO 1 in borate buffer.

H. Microconcentrator: Microcon YM-3 (amicon, Milipore GmbH, Eschborn, Germany)

Method

100 μL SIA solution is added to 400 μL of the aminoHES12KD E solution and is allowed to react with agitation for 0.5 hours at room temperature. The excess crosslinker is removed by centrifuging the sample at 14000×g for 60 minutes using a microconcentrator. After centrifuging the sample is brought up to its original volume in borate buffer and this process is repeated two more times. The residual solution is added to 1 mL of ThioEPO solution and the reaction mixture is incubated for 16 hour at room temperature. Reactivity of the excess iodoacetamide is quenched at the end of the incubation period by the addition of cysteine to a final concentration of 10 mM. The reaction mixture is applied to a desalting column equilibrated with PBS buffer and the protein content of the fractions are monitored with a Coomassie protein assay reagent. All fractions containing the protein conjugate are pooled and the conjugate was obtained by lyophylisation after dialysis against water over night.

Alternatives:

In this reaction, all cross-linkers could be used, which have a succinimide- or a sulfosuccinimide function and a iodoacetamide function separated by a spacer. Further examples are found in table 2. They are marked with a "C" and are available from Perbio Science Deutschland GmbH, Bonn, Germany.

1.2 Example Protocol 2

Conjugation of ThioEPO 1 to SH reactiveHES12KD Bromoacetamide D2, F2 or Iodoacetamide D3.[9]

[9] de Valasco, Merkus, Anderton, Verheul, Lizzio, Van der Zee, van Eden, Hoffmann, Verhoef, Snippe, 1995, *Infect. Immun.*, 63, 961

Materials

A. Phosphate buffer. Composition is 100 mM sodium phosphate, pH 6.1, 5 mM EDTA.
B. PBS, phosphate buffered saline: 10 mM sodium phosphate, 150 mM NaCl, pH 7.4.
C. SH reactiveHES12KD bromoacetamide D2. Prepared at 10 mg/mL in phosphate buffer.
D. D-Salt™ Dextran Desalting Columns, 2×5 mL bed volume (Perbio Science Deutschland GmbH, Bonn, Germany)
E. Coomassie® Protein Assay Reagent (Perbio Science Deutschland GmbH, Bonn, Germany)
F. ThioEPO solution: 5 mg/mL of ThioEPO 1 in phosphate buffer.

Method 1 mL SH reactiveHES12KD bromoacetamide D2 solution and 1 mL of ThioEPO solution are combined and the reaction mixture is incubated for 48 hours at room temperature. Reactivity of the excess bromoacetamide is quenched at the end of the incubation period by the addition of cysteine to a final concentration of 10 mM. The reaction mixture is applied to a desalting column, equilibrated with PBS buffer. The protein content of the fractions are monitored with a Coomassie protein assay reagent, all fractions containing the protein conjugate are pooled and the conjugate is obtained by lyophylisation after dialysis against water over night.

Alternatives:

Instead of the isolation of the SH reactive HES12KD-bromoacetamid D2, amino HES12KD (E, H, I) could be linked with a cross-linker via a succinimide- and a bromoacetamide function (see 1.1 above). SBAP is a member of this group of cross-linkers and is found in table 2, marked with a "D".

2. Reaction of Thio-EPO with a Maleimide-Modified SH-Reactive HES 2.1 Example Protocol 3

Conjugation of ThioEPO to HES12KD with a Cross-Linker Containing a Hydrazide and a Maleimide Functional Group, e.g. $M_2C_2H$.

Materials

A. $M_2C_2H$ stock: 10 mg/mL M2C2H in DMSO, prepared fresh
B. HES12KD: 10 mg/mL in 0.1 M sodium acetate buffer, pH 5.5
C. ThioEPO solution: 5 mg/mL of ThioEPO in phosphate/NaCl-buffer
D. Phosphate/NaCl: 0.1 M sodium phosphate, 50 mM NaCl, pH 7.0
E. Microconcentrator: Microcon YM-3 (amicon, Milipore GmbH, Eschborn, Germany)
F. Gel filtration column: for example, Sephadex® G-200 (1.5×45 cm)
G. Coomassie® Protein Assay Reagent (Perbio Science Deutschland GmbH, Bonn, Germany)
H. PBS, phosphate buffered saline: 10 mM sodium phosphate, 150 mM NaCl, pH 7.4.

Method $M_2C_2H$ solution is added to 400 μL of the HES12KD solution to a final concentration of 1 mM and is allowed to react with agitation for 2 hours at room temperature. The excess cross-linker is removed by centrifuging the sample at 14000×g for 60 minutes using a microconcentrator. After centrifuging the sample is brought up to its original volume in phosphate/NaCl buffer and this process is repeated two more times. To the $M_2C_2H$-modified HES12KD 0.5 mL of ThioEPO solution is added and the reaction mixture is incubated for 2 hours at room temperature. Reactivity of the excess maleimides is quenched at the end of the incubation period by the addition of cysteine to a final concentration of 10 mM. The reaction mixture is applied to Sephadex® G-200 (1.5×45 cm) equilibrated with PBS buffer and 1 mL fractions are collected. The protein content of the fractions is monitored with a Coomassie protein assay reagent. All fractions containing the protein conjugate are pooled and the conjugate was obtained by lyophylisation after dialysis against water over night.

Procedural Notes

The hydrazone adduct is slightly less stable at extremes of pH. For applications that may involve treatment at low pH, we reduced the hydrazone by treatment with 30 mM sodium cyanoborohydride in PBS buffer to a hydrazine. For most applications, this extra step is unnecessary.

2.2 Example Protocol 4

Conjugation of ThioEPO to Maleimido-HES12KD B.

Materials

A. Maleimido-HES12KD B: 10 mg/mL in 0.1 M sodium acetate buffer, pH 5.5
B. ThioEPO solution: 5 mg/mL of ThioEPO in phosphate/NaCl-buffer
C. Phosphate/NaCl: 0.1 M sodium phosphate, 50 mM NaCl, pH 7.0
D. Gel filtration column: for example, Sephadex® G-200 (1.5×45 cm)
E. Coomassie® Protein Assay Reagent (Perbio Science Deutschland GmbH, Bonn, Germany)
F. PBS, phosphate buffered saline: 10 mM sodium phosphate, 150 mM NaCl, pH 7.4.

Method 1 mL SH-reactive-HES12KD B solution and 1 mL of ThioEPO 1 solution are combined and the reaction mixture is incubated for 2 hours at room temperature. Reactivity of the excess maleimides is quenched at the end of the incubation period by the addition of cysteine to a final concentration of 10 mM. The reaction mixture is applied to Sephadex® G-200 (1.5×45 cm) equilibrated with PBS buffer and 1 mL fractions are collected. The protein content of the fractions is monitored with a Coomassie protein assay reagent. All fractions containing the protein conjugate are pooled and the conjugate is obtained by lyophylisation after dialysis against water over night.

2.3 Example Protocol 12

Conjugation of ThioEPO to aminoHES12KD (E, H, I) with a Cross-Linker Containing a NHS-Active-Ester and a Maleimide Group, e.g. SMCC Materials A: Microconcentrator: Microcon YM-10 (amicon, Milipore GmbH, Eschborn, Germany).
B. PBS, phosphate buffered saline: 10 mM sodium phosphate, 150 mM NaCl, pH 7.4.
C. AminoHES12KD E, H or I. Prepared at 10 mg/mL in PBS buffer.

D. SMCC solution: 1 mg SMCC were dissolved in 50 µL DMSO
E. D-Salt™ Dextran Desalting Columns, 2×5 mL bed volume (Perbio Science Deutschland GmbH, Bonn, Germany)
F. Coomassie® Protein Assay Reagent (Perbio Science Deutschland GmbH, Bonn, Germany)
G. ThioEPO 1 solution: 5 mg/mL of ThioEPO 1 in PBS buffer.

Method

To 50 µL SMCC solution 400 µL of the aminoHES12KD E solution is added and the reaction mixture is allowed to react with agitation for 80 min at room temperature and for 10 min at 46° C. The excess crosslinker is removed by centrifugation of the reaction mixture through a microconcentrator at 14000×g for 60 min. The volume is brought up to 450 µL with PBS buffer and the process is repeated two more times. After the last centrifugation, the residual solution is brought up to 450 µL with PBS and is added to 1 mL of ThioEPO solution and the reaction mixture are incubated for 16 hours at room temperature. Reactivity of the excess maleimide is quenched at the end of the incubation period by the addition of cysteine to a final concentration of 10 mM. The reaction mixture is applied to a desalting column equilibrated with PBS buffer. The protein content of the fractions are monitored with a Coomassie protein assay reagent, all fractions containing the protein conjugate are pooled and the conjugate is obtained by lyophylisation after dialysis against water over night.

Alternatives:

In this reaction, all cross-linkers could be used which have a succinimide- or a sulfosuccinimide function and a maleimide-function, separated by a spacer. Further examples for this group of molecules, available from Perbio Science Deutschland GmbH, Bonn, Germany, are found in table, 2, marked with an "E". There is a further group of cross-linkers, which have instead of a maleimide function an activated disulfide function. These cross-linkers could also be used for the conjugation. However, the disulfide bond of the conjugate is cleavable under reductive conditions. Members of this group are marked in table 2 with a "F". A third group of cross-linkers uses instead of a maleimide function a vinylsulfone function as a SH-reactive group. A member of this group "SVSB" is marked in table 2 with a "G".

Example 4

Conjugation Reactions with Oxidized EPO

1. Oxidation of Glyco-EPO
1.1 Oxidation of Glyco-EPO with Sodium Meta-Periodate: Example Protocol 5

Materials
A. Glyco-EPO solution: 10 mg/mL of Glyco-EPO in acetate buffer
B. Sodium meta-periodate solution: 10 mM or 100 mM sodium periodate in acetate buffer, prepared fresh. Keep in dark. Using these solutions, the final concentration of sodium periodate in the oxidation mixture is 1 mM or 10 mM, respectively.
C. acetate buffer: 0.1 M sodium acetate buffer, pH 5.5
D. Glycerol
E. Microconcentrator: Microcon YM-3 (amicon, Milipore GmbH, Eschborn, Germany)

Method

All steps were performed in the dark.

To 1 mL of cold Glyco-EPO solution 0.1 mL of cold sodium meta-periodate solution were added and the oxidation reaction was allowed to proceed for 1 hour in the dark. If the Glyco-EPO to be oxidized contained sialic acid residues, then the oxidation conditions were 1 mM sodium periodate, 0° C. Otherwise, 10 mM sodium periodate at room temperature was used. To stop the oxidation glycerol was added to a final concentration of 15 mM and incubated for 5 minutes at 0° C. The excess reagents and byproducts were remove by centrifuging of the product at 14000×g for 60 minutes using a microconcentrator. After centrifuging, sample was brought up to its original volume in the buffer used in the next modification step, e.g. in the acetate buffer. This process was repeated two more times.

1.2 Enzymatic Oxidation of Glyco-EPO: Example Protocol 6

The enzymatic oxidation of EPO is described elsewhere (Chamow et al., 1992, J. Biol. Chem., 267, 15916-15922).

2. Conjugation with Hydrazine/Hydrazide-Derivatives
2.1 Example Protocol 7

Conjugation of oxidised Glyco-EPO to Thio-HES12KD M, O or Q with a Cross-linker containing a hydrazide and a maleimide functional group, e.g. $M_2C_2H$ (Perbio Science, Deutschland GmbH, Bonn, Germany).

Materials
A. $M_2C_2H$ stock: 10 mg/mL $M_2C_2H$ in DMSO, prepared fresh
B. Oxidised Glyco-EPO solution from 6.1.1: 5 mg/mL of Glyco-EPO in acetate buffer
C. Thio-HES12KD M, 0 or Q: 10 mg/mL in phosphate/NaCl buffer
D. Acetate buffer: 0.1 M sodium acetate buffer, pH 5.5
E. Phosphate/NaCl: 0.1 M sodium phosphate, 50 mM NaCl, pH 7.0
F. Microconcentrator: Microcon YM-3 (amicon, Milipore GmbH, Eschborn, Germany)
G. Gel filtration column: for example, Sephadex® G-200 (1.5×45 cm)
H. Coomassie® Protein Assay Reagent (Perbio Science Deutschland GmbH, Bonn, Germany)
I. PBS, phosphate buffered saline: 10 mM sodium phosphate, 150 mM NaCl, pH 7.4

Method $M_2C_2H$ stock solution is added to 1 mL of oxidized Glyco-EPO to a final concentration of 1 mM and is allowed to react with agitation for 2 hours at room temperature. The excess crosslinker is removed by centrifuging the sample at 14000×g for 60 minutes using a microconcentrator. After centrifuging the sample is brought up to its original volume in phosphate/NaCl buffer and this process was repeated two more times. To the $M_2C_2H$-modified Glyco-EPO 1 mL of Thio-HES12KD M, 0 or Q solution is added and the reaction mixture is incubated for 16 hours at room temperature. Reactivity of the excess maleimides is quenched at the end of the incubation period by the addition of cysteine. The reaction mixture is applied to Sephadex® G-200 (1.5×45 cm) equilibrated with PBS and 1 mL fractions are collected. The protein content of the fractions is monitored with a Coomassie protein assay reagent, all fractions containing the protein conjugate are pooled and the conjugate is obtained by lyophylisation after dialysis against water over night.

Procedural Notes

The hydrazone adduct is slightly less stable at extremes of pH. For applications that may involve treatment at low pH, we reduced the hydrazone by treatment with 30 mM sodium cyanoborohydride in PBS buffer to a hydrazine. For most applications, this extra step was unnecessary.

2.2 Example Protocol 8A

Direct conjugation of oxidised Glyco-EPO to Hydrazido-HES12KD L or J.

Materials

A. Oxidised Glyco-EPO solution from 6.1.1: 5 mg/mL of Glyco-EPO in acetate buffer
B. Hydrazido-HES12KD L or J: 10 mg/mL in acetate buffer
C. Acetate buffer: 0.1 M sodium acetate buffer, pH 5.5
D. Gel filtration column: for example, Sephadex® G-200 (1.5×45 cm)
E. Coomassie® Protein Assay Reagent (Perbio Science Deutschland GmbH, Bonn, Germany)
F. PBS, phosphate buffered saline:10 mM sodium phosphate, 150 mM NaCl, pH 7.4

Method 1 mL of Hydrazido-HES12KD L or J solution and 1 mL of oxidized Glyco-EPO solution are combined and the reaction mixture is allowed to react with agitation for 16 hours at room temperature. The reaction mixture is applied to Sephadex® G-200 (1.5×45 cm) equilibrated with PBS and 1 mL fractions are collected. The protein content of the fractions are monitored with a Coomassie protein assay reagent, all fractions containing the protein conjugate are pooled and the conjugate is obtained by lyophylisation after dialysis against water over night.

Procedural Notes

The hydrazone adduct is slightly less stable at extremes of pH. For applications that may involve treatment at low pH, the hydrazone may be reduced by treatment with 30 mM sodium cyanoborohydride in PBS buffer to a hydrazine. For most applications, this extra step is unnecessary.

2.3 Example Protocol 8B

To 100 μl of a 0.5 mg/ml solution of oxidized EPO in a buffer containing 0.1 M sodium acetate and 150 mM sodium chloride at a pH of 5.2, 50 μL of a 20 mg/ml solution of HES18/0.5 L dissolved in a 0.1 M sodium acetate buffer, pH 5.2 (synthesised corresponding to Example 2 2.1b) were added and the mixture was incubated at 22° C. for 14.5 h. The crude reaction mixture was analysed by SDS gel electrophoresis and stained with Coomassie. The result of the conjugation is shown in FIG. 1. The observed molecular shift demonstrates that the conjugation was successful. The smear results from the heterogeneity of HES. FIG. 2 demonstrates that HES is conjugated to a carbohydrate moiety of a carbohydrate side chain.

3. Conjugation with Hydroxylamine-Derivatives[10]

[10]Rose, 1994, *Am. Chem. Soc.*, 116, 30

3.1 Example Protocol 9A

Conjugation of Oxidized Glyco-EPO to Hydroxylamino-HES12KD K

Materials

A. Oxidised Glyco-EPO solution from 6.1.1: 5 mg/mL of Glyco-EPO in acetate buffer
B. Hydroxylamino-HES12KD K: 10 mg/mL in acetate buffer
C. Acetate buffer: 0.1 M sodium acetate buffer, pH 5.5
D. Gel filtration column: for example, Sephadex® G-200 (1.5×45 cm)
E. Coomassie® Protein Assay Reagent (Perbio Science Deutschland GmbH, Bonn, Germany)
F. PBS, phosphate buffered saline:10 mM sodium phosphate, 150 mM NaCl, pH 7.4

Method 1 mL of Hydroxylamino-HES12KD K solution and 1 mL of oxidized Glyco-EPO solution are combined and the reaction mixture is allowed to react with agitation for 16 hours at room temperature. The reaction mixture is applied to Sephadex® G-200 (1.5×45 cm) equilibrated with PBS and 1 mL fractions were collected. The protein content of the fractions are monitored with a Coomassie protein assay reagent, all fractions containing the protein conjugate are pooled and the conjugate is obtained by lyophylisation after dialysis against water over night.

3.2 Example Protocol 9B

To 100 μl of a 0.5 mg/ml solution of oxidized EPO in a buffer containing 0.1 M sodium acetate and 150 mM sodium chloride at a pH of 5.2, 50 μL of a 20 mg/ml solution of HES18/0.5 K dissolved in a 0.1 M sodium acetate buffer, pH 5.2 (synthesised corresponding to Example 2. 4) were added and the mixture was incubated at 22° C. for 14.5 h. The crude reaction mixture was analysed by SDS gel electrophoresis and stained with Coomassie. The result of the conjugation is shown in FIG. 1. The observed molecular shift demonstrates that the conjugation was successful. The smear results from the heterogeneity of HES. FIG. 2 demonstrates that HES is conjugated to a carbohydrate moiety of a carbohydrate side chain.

Example 5

Characterization of Galactose Oxidase Treated EPO N-Glycans

Recombinant EPO or partially desialylated EPO forms (generated by limited mild acid hydrolysis) were incubated with galactose oxidase in the presence of catalase at 37° C. from 30 min-4 hours at 37° C. in 0.05 M Na-phosphate buffer pH 7.0. Progress of the reaction was monitored by removal of 50 μg aliquots of the EPO and subsequent treatment of the protein with polypeptide N-glycanase.

Liberated N-linked oligosaccharides (monitored by SDS-PAGE detection of the de-N-glycosylated polypeptide) were subjected to HPAEC-PAD mapping as described (Grabenhorst et al., 1999, Nimtz et al., 1993/1994; Schlenke et al., 1999) before and after removal of sialic acids. Quantitation of oxidised galactose residues in individual EPO oligosaccharides was performed by the typical shift observed in HPAEC-PAD and was also verified by MALDI/TOF MS of the oligosaccharide mixtures.

Example 6

Characterization of HAS Modified EPO

Separation of HAS modified EPO forms from nonreacted EPO and HAS-precursor molecules was achieved by gel filtration using e.g. Ultrogel AcA 44/54 or similar gel filtration media. Alternatively, nonreacted HAS was removed by immuno affinity isolation of EPO on a 4 mL column containing a monoclonal antibody coupled to Affigel (BioRad) and subsequent separation of unmodified EPO by gel filtration (e.g. using a matrix enabling the separation of globular proteins of a relative molecular mass between 20 kDa and 200 kDa).

HAS modified EPOs were identified by SDS-PAGE analysis (using 12.5 or 10% acrylamide gels) through detection of their higher molecular weight compared to unmodified EPO upon staining of gels with Coomassie Brilliant Blue. The higher molecular weight of HAS modified EPO polypeptides was also identified by Western Blot analysis of samples using a polyclonal antibody raised against recombinant human EPO.

N-glycan modification of EPO forms was demonstrated by their successful removal from the EPO protein with polypeptide N-glycanase (recombinant N-glycosidase from Roche, Germany employing 25 units/mg EPO protein at 37° C. for 16 hours); analysis by SDS-PAGE resulted in a typical shift of the EPO protein to a migration position of the N-glycosidase treated unmodified EPO of approximately 20 KDa.

Modification of the single desialylated and galactose oxidase treated EPO O-glycan at Ser 126 was demonstrated by SDS-PAGE migration of the de-N-glycosylated product by detection of its migration position compared to nonreacted de-N-glycosylated EPO. If required, modified EPO was fractionated by RP-HPLC on a C8-phase before SDS-PAGE analysis. HAS O-glycan modification of EPO was also analysed by β-elimination of the O-glycan and detection of the de-O-glycosylated form of EPO in Western blots using a polyclonal antibody raised against recombinant human EPO.

Example 7

Quantitation of EPO and Modified EPO Forms

EPO forms where quantitated by UV measurements as described in Ph. Eur (2000, Erythropoietini solutio concentrata, 1316, 780-785) and compared to the international BRP reference EPO standard. Alternatively, EPO concentrations were determined by a RP-HPLC assay using a RP-C4-column and absorption at 254 nm employing 20, 40, 80 and 120 µg of the BRP standard EPO reference preparation for calibration.

Example 8

In-Vitro Biological Activity of HES-Modified Recombinant Human EPO

Purified HES-modified EPO is tested for activity using the erythropoietin bioactivity assay as described by Krystal [Krystal, 1984, Exp. Heamatol., 11, 649-660].

Anemia is induced in NMRI mice by treatment with phenylhydrazine hydrochloride and spleen cells are collected and used as described in [Fibi et al., 1991, Blood, 77, 1203 ff.]. Dilutions of EPO are incubated with $3 \times 10^5$ cells/well in 96-well microtiter plates. After 24 hours at 37° C. in a humidified atmosphere (5% $CO_2$) cells are labeled for 4 hours with 1 µCi of $^3$H-thymidine per well. Incorporated radioactivity is determined by liquid scintillation counting. The International reference EPO standard (BRP-standard) is used for comparison.

Alternatively, EPO bioactivity may be measured by an in vitro assay using the EPO-sensitive cell line TF-1 (Kitamura et. al., [J. cell Phys., 140. 323-334]. Exponentially growing cells are washed free of growth factors and are incubated in the presence of serial dilutions of the EPO for further 48 hours. Proliferation of the cells is assessed by using the MTT reduction assay as described by Mosmann [Mosmann, 1983, J. Immunol. Methods, 65, 55-63].

Example 9

In-Vivo Activity Determination of EPO and HAS-Modified EPO Forms: (HCO Fragen)

In vivo activity determinations are performed in normocythemic mice by measuring the increase of reticulocytes after 4 days after animals received the foreseen dose of EPO or modified EPO forms. Assays are performed using the BRP EPO standard which is calibrated against the WHO EPO standard in the polycythemic mouse assay. EPO samples are diluted in phosphate buffered saline containing 1 mg/ml of bovine serum albumin (Sigma).

0.5 ml of the EPO test solution in Dulbecco's buffered saline (corresponding to an EPO protein equivalent of a 100, 80, 40 or 20 IU/ml of the BRP standard EPO) are infected subcutaneously per animal. Blood samples are taken after 4 days after injection and reticulocytes are stained with acridine orange; quantitation of reticulocytes is performed by flow-cytometry by counting a total of 30,000 blood cells within 5 hours after the blood sample was taken (see Ph. Eur, 2000, Erythropoietini solutio concentrata, 1316, pages 780-785) and European Pharmacopoeia (1996/2000, attachment 2002).

Example 10

In-Vivo Half-Life Determinations

Rabbits are injected intravenously with specified amounts of unmodified or HAS-modified EPO forms. Blood samples are obtained at specified times, and serum is prepared. Serum erythropoietin levels are determined by in vitro bioassay or by an EPO-specific commercial ELISA.

Example 11

In Vivo Pharmacokinetics

In mice: Each animal receive 300 IU EPO/kg subcutaneously. Seven days after the post-treatment hematocrit of each animal is determined. A substantial increase in hematocrit is observed in all animals treated with modified EPO.

In rabbits: Rabbits are treated with a single dose of unmodified or HAS-modified EPO corresponding to 200 or up to 800 ng/kg body weight. After 2, 6, 16, 24 and 48 hours blood samples are analyzed by using a commercial EPO-specific ELISA for determination of plasma concentrations. Mean plasma EPO concentrations are determined and the average initial half-lives (α-phase) and the terminal half-lives (β-phase) are calculated from the ELISA values as described: (Zettlmissl et al., 1989, J. Biol. Chem., 264, 21153-21159).

Literature:

Sytkowski, Lunn, Risinger, and Davis, 1999, An Erythropoietin Fusion Protein Comprised of Identical Repeating Domains Exhibits Enhanced Biological Properties, J. Biol. Chem., 274, 24773-24778.

Example 12

Assessment of the In Vitro Biological Activity of HES-Modified Recombinant Human IL-2

Modified IL2 is recovered by gel filtration on Ultrogel AcA 54. Aliquots of corresponding fraction are sterile filtrated and IL2 bioactivity is determined by using the IL2 dependent murine CTLL-2 cell line [Gillis, Ferm, On, and Smith, 1978, J. Immunol., 120, 2027-2032]. Activity is related to the international reference IL2 standard preparation.

In the context of the present invention, the degree of substitution, denoted as DS, relates to the molar substitution, as described above (see also Sommermeyer et al., 1987, Krankenhauspharmazie, 8(8), 271-278, in particular p. 273). Throughout the invention, the DS of the HES18/04 when

Example 13

Formation of Hydroxyethyl Starch Derivatives by Reductive Amination of the Non-Oxidised Reducing End

Example 13.1

Reaction of Hydroxyethyl Starch with 1,3-diamino-2-hydroxy propane

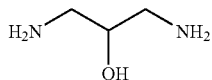

a) To a solution of 200 mg hydroxyethyl starch (HES18/0.4 (MW=18,000 D, DS=0.4)) in 5 ml water, 0.83 mmol 1,3-diamino-2-hydroxy propane and 50 mg sodium cyanoborohydrate $NaCNBH_3$ were added. The resulting mixture was incubated at 80° C. for 17 h. The reaction mixture was added to 160 ml of a cold 1:1 mixture of acetone and ethanol (v/v). The precipitate was collected by centrifugation and dialysed for 4 d against water (SnakeSkin dialysis tubing, 3.5 KD cut off, Perbio Science Deutschland GmbH, Bonn, D), and lyophilized.

b) Incubation of the mixture resulting from adding 0.83 mmol 1,3-diamino-2-hydroxy propane and 50 mg sodium cyanoborohydrate $NaCNBH_3$ to the solution of 200 mg hydroxyethyl starch was also possible and carried out at 25° C. for 3 d.

Example 13.2

Reaction of Hydroxyethyl Starch with 1,2-dihydroxy-3-amino propane

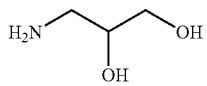

a) To a solution of 200 mg hydroxyethyl starch (HES18/0.4 (MW=18,000 D, DS=0.4)) in 5 ml water, 0.83 mmol 1,2-dihydroxy-3-amino propane and 50 mg sodium cyanoborohydrate $NaCNBH_3$ were added. The resulting mixture was incubated at 80° C. for 17 h. The reaction mixture was added to 160 ml of a cold 1:1 mixture of acetone and ethanol (v/v). The precipitate was collected by centrifugation and dialysed for 4 d against water (SnakeSkin dialysis tubing, 3.5 KD cut off, Perbio Science Deutschland GmbH, Bonn, D), and lyophilized.

The reaction of 1,2-dihydroxy-3-amino propane with HES was confirmed indirectly by quantification of formaldehyde, resulting from the oxidative cleavage of the 1,2-diole in the reaction product by periodate as described by G. Avigad, Anal. Biochem. 134 (1983) 449-504.

b) Incubation of the mixture resulting from adding 0.83 mmol 1,2-dihydroxy-3-amino propane and 50 mg sodium cyanoborohydrate $NaCNBH_3$ to the solution of 200 mg hydroxyethyl starch was also possible and carried out at 25° C. for 3 d.

Example 13.3

Reaction of Hydroxyethyl Starch with 1,4-diamino butane

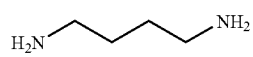

a) To a solution of 200 mg hydroxyethyl starch (HES18/0.4 (MW=18,000 D, DS=0.4)) in 5 ml water, 0.83 mmol 1,4-diamino butane and 50 mg sodium cyanoborohydrate $NaCNBH_3$ were added. The resulting mixture was incubated at 80° C. for 17 h. The reaction mixture was added to 160 ml of a cold 1:1 mixture of acetone and ethanol (v/v). The precipitate was collected by centrifugation and dialysed for 4 d against water (SnakeSkin dialysis tubing, 3.5 KD cut off, Perbio Science Deutschland GmbH, Bonn, D), and lyophilized.

b) Incubation of the mixture resulting from adding 0.83 mmol 1,4-diamino butane and 50 mg sodium cyanoborohydrate $NaCNBH_3$ to the solution of 200 mg hydroxyethyl starch was also possible and carried out at 25° C. for 3 d.

Example 13.4

Reaction of Hydroxyethyl Starch with 1-mercapto-2-amino ethane

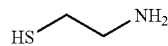

a) To a solution of 200 mg hydroxyethyl starch (HES18/0.4 (MW=18,000 D, DS=0.4)) in 5 ml water, 0.83 mmol 1-mercapto-2-amino ethane and 50 mg sodium cyanoborohydrate $NaCNBH_3$ were added. The resulting mixture was incubated at 80° C. for 17 h. The reaction mixture was added to 160 ml of a cold 1:1 mixture of acetone and ethanol (v/v). The precipitate was collected by centrifugation and dialysed for 4 d against water (SnakeSkin dialysis tubing, 3.5 KD cut off, Perbio Science Deutschland GmbH, Bonn, D), and lyophilized.

b) Incubation of the mixture resulting from adding 0.83 mmol 1-mercapto-2-amino ethane and 50 mg sodium cyanoborohydrate $NaCNBH_3$ to the solution of 200 mg hydroxyethyl starch was also possible and carried out at 25° C. for 3 d.

Example 14

Formation of Hydroxyethyl Starch Derivatives by Conjugation with the Non-Oxidised Reducing End

Example 14.1

Reaction of Hydroxyethyl Starch with Carbohydrazide

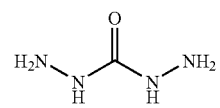

0.96 g of HES18/0.4 (MW=18,000 D, DS=0.4) were dissolved in 8 ml aqueous 0.1 M sodium acetate buffer, pH 5.2, and 8 mmol carbohydrazide (Sigma Aldrich, Taufkirchen, D) were added. After stirring for 18 h at 25° C., the reaction mixture was added to 160 ml of a cold 1:1 mixture of acetone and ethanol (v/v). The precipitated product was collected by centrifugation, re-dissolved in 40 ml water, and dialysed for 3 d against water (SnakeSkin dialysis tubing, 3.5 KD cut off, Perbio Science Deutschland GmbH, Bonn, D), and lyophilized.

Example 14.2

Reaction of Hydroxyethyl Starch with Adepic Dihydrazide

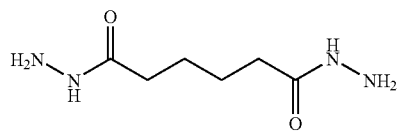 [SMILES: NNC(=O)CCCCC(=O)NN]

0.96 g of HES18/0.4 (MW=18,000 D, DS=0.4) were dissolved in 8 ml aqueous 0.1 M sodium acetate buffer, pH 5.2, and 8 mmol adepic dihydrazide (Lancaster Synthesis, Frankfurt/Main, D) were added. After stirring for 18 h at 25° C., the reaction mixture was added to 160 ml of a cold 1:1 mixture of acetone and ethanol (v/v). The precipitated product was collected by centrifugation, re-dissolved in 40 ml water, and dialysed for 3 d against water (SnakeSkin dialysis tubing, 3.5 KD cut off, Perbio Science Deutschland GmbH, Bonn, D), and lyophilized.

Example 14.3

Reaction of Hydroxyethyl Starch with 1,4-phenylene-bis-3-thiosemicarbazide

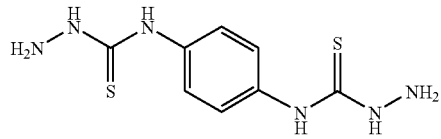 [SMILES: NNC(=S)Nc1ccc(NC(=S)NN)cc1]

0.96 g of HES18/0.4 (MW=18,000 D, DS=0.4) were dissolved in 8 ml aqueous 0.1 M sodium acetate buffer, pH 5.2, and 8 mmol 1,4-phenylene-bis-3-thiosemicarbazide (Lancaster Synthesis, Frankfurt/Main, D) were added. After stirring for 18 h at 25° C., 8 ml water was added to the reaction mixture, and the suspension was centrifuged for 15 min at 4,500 rpm. The clear supernatant was decanted and subsequently added to 160 ml of a cold 1:1 mixture of acetone and ethanol (v/v). The precipitated product was collected by centrifugation, re-dissolved in 40 ml water, and centrifugated for 15 min at 4,500 rpm. The clear supernatant was dialysed for 3 d against water (SnakeSkin dialysis tubing, 3.5 KD cut off, Perbio Science Deutschland GmbH, Bonn, D), and lyophilized.

Example 14.4

Reaction of Hydroxyethyl Starch with O-[2-(2-aminooxy-ethoxy)-ethyl]-hydroxylamine

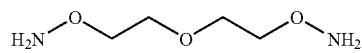

O-[2-(2-aminooxy-ethoxy)-ethyl]-hydroxylamine was synthesized as described in Boturyn et al. Tetrahedron 53 (1997) p. 5485-5492 in 2 steps from commercially available materials.

0.96 g of HES18/0.4 (MW=18,000 D, DS=0.4) were dissolved in 8 ml aqueous 0.1 M sodium acetate buffer, pH 5.2, and 8 mmol O-[2-(2-aminooxy-ethoxy)ethyl]-hydroxylamine were added. After stirring for 18 h at 25° C., the reaction mixture was added to 160 ml of a cold 1:1 mixture of acetone and ethanol (v/v). The precipitated product was collected by centrifugation, re-dissolved in 40 ml water, and dialysed for 3 d against water (SnakeSkin dialysis tubing, 3.5 KD cut off, Perbio Science Deutschland GmbH, Bonn, D), and lyophilized.

Example 15

Formation of Hydroxyethyl Starch Derivatives by Reaction with the Oxidised Reducing End

Example 15.1

Reaction of Hydroxyethyl Starch with Carbohydrazide

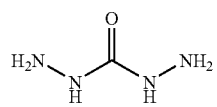

0.12 mmol Oxo-HES 10/0.4 (MW=10,000 D, DS=0.4, prepared according to DE 196 28 705 A1) were dissolved in 3 ml absolute dimethyl sulfoxide (DMSO) and added dropwise under nitrogen to a mixture of 15 mmol of carbohydrazide (Sigma Aldrich, Taufkirchen, D) in 15 ml. DMSO. After stirring for 88 h at 65° C., the reaction mixture was added to 160 ml of a cold 1:1 mixture of acetone and ethanol (v/v). The precipitate was collected by centrifugation and was dialysed for 4 d against water (SnakeSkin dialysis tubing, 3.5 KD cut off, Perbio Science Deutschland GmbH, Bonn, D) and lyophilized.

Example 15.2

Reaction of Hydroxyethyl Starch with 1,4-phenylene-bis-3-thiosemicarbazide

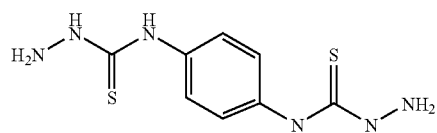

0.12 mmol Oxo-HES 10/0.4 (MW=10,000 D, DS=0.4, prepared according to DE 196 28 705 A1) were dissolved in 3 ml absolute dimethyl sulfoxide (DMSO) and added dropwise under nitrogen to a mixture of 15 mmol of 1,4-phenylene-bis-3-thiosemicarbazide (Lancaster Synthesis, Frankfurt/Main, D) in 15 ml DMSO. After stirring for 88 h at 65° C., the reaction mixture was added to 160 ml of a cold 1:1 mixture of acetone and ethanol (v/v). The precipitate was collected by centrifugation and was dialysed for 4 d against water (SnakeSkin dialysis tubing, 3.5 KD cut off, Perbio Science Deutschland GmbH, Bonn, D) and lyophilized.

Example 15.3

Reaction of Hydroxyethyl Starch with Hydrazine

1.44 g (0.12 mmol) of Oxo-HES 10/0.4 (MW=10,000 D, DS=0.4, prepared according to DE 196 28 705 A1) were dissolved in 3 ml absolute dimethyl sulfoxide (DMSO) and were added dropwise under nitrogen to a mixture of 0.47 ml (15 mmol) hydrazine in 15 ml DMSO. After stirring for 19 h at 40° C. the reaction mixture was added to 160 ml of a 1:1 mixture of ethanol and acetone (v/v). The precipitated product was collected by centrifugation, redissolved in 40 mL of water and dialysed for 2 days against a 0.5% (v/v) triethylamine in water solution and for 2 days against water (SnakeSkin dialysis tubing, 3.5 KD cut off, Perbio Science Deutschland GmbH, Bonn, Germany) and lyophilized.

Example 15.4

Reaction of Hydroxyethyl Starch with Hydroxylamine

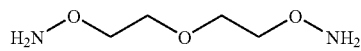

O-[2-(2-aminooxy-ethoxy)-ethyl]-hydroxylamine was synthesized as described by Boturyn et al in 2 steps from commercially available materials (Boturyn, Boudali, Constant, Defrancq, Lhomme, 1997, *Tetrahedron*, 53, 5485).

1.44 g (0.12 mmol) of Oxo-HES 10/0.4 (MW=10,000 D, DS=0.4, prepared according to DE 196 28 705 A1) were dissolved in 3 ml absolute dimethyl sulfoxide (DMSO) and were added dropwise under nitrogen to a mixture of 2.04 g (15 mmol) O-[2-(2-aminooxy-ethoxy)-ethyl]-hydroxylamine in 15 ml DMSO. After stirring for 48 h at 65° C. the reaction mixture was added to 160 ml of a 1:1 mixture of ethanol and acetone (v/v). The precipitated product was collected by centrifugation, redissolved in 40 ml of water and dialysed for 4 days against water (SnakeSkin dialysis tubing, 3.5 KD cut off, Perbio Science Deutschland GmbH, Bonn, Germany) and lyophilized.

Example 15.5

Reaction of Hydroxyethyl Starch with Adepic Dihydrazide

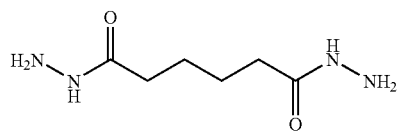 [SMILES: NNC(=O)CCCCC(=O)NN]

1.74 g (15 mmol) adepic dihydrazide were dissolved in 20 ml absolute dimethyl sulfoxide (DMSO) at 65° C. and 1.44 g (0.12 mmol) of Oxo-HES 10/0.4 (MW=10,000 D, DS=0.4, prepared according to DE 196 28 705 A1), dissolved in 3 ml absolute DMSO were added dropwise under nitrogen. After stirring for 68 h at 60° C. the reaction mixture was added to 200 ml of water The solution containing the reaction product was dialysed for 2 days against a 0.5% (v/v) triethylamine in water solution and for 2 days against water (SnakeSkin dialysis tubing, 3.5 KD cut off, Perbio Science Deutschland GmbH, Bonn, Germany) and lyophilized.

Example 15.6

Reaction of Hydroxyethyl Starch with 1,4-diamino butane

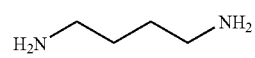

1.44 g (0.12 mmol) of Oxo-HES 10/0.4 (MW=10,000 D, DS=0.4, prepared according to DE 196 28 705 A1) were dissolved in 3 ml dry dimethyl sulfoxide (DMSO) and were added dropwise under nitrogen to a mixture of 1.51 ml (15 mmol) 1,4-diaminobutane in 15 ml DMSO. After stirring for 19 h at 40° C. the reaction mixture was added to 160 ml of a 1:1 mixture of ethanol and acetone (v/v). The precipitate Amino-HES10KD/0.4 was collected by centrifugation, redissolved in 40 ml of water and dialysed for 4 days against water (SnakeSkin dialysis tubing, 3.5 KD cut off, Perbio Science Deutschland GmbH, Bonn, Germany) and lyophilized.

Example 16

Oxidation of Erythropoietin

Oxidized erythropoietin was produced as described in Example 20. As oxidized erythropoietin, EPO-GT-1-A as described in Example 20.11(c) was used (EPO-GT-1 without acid hydroylsis, treated with mild periodate oxidation).

Example 17

Conjugation of Hydroxyethyl Starch Derivatives with Oxidized Erythropoietin of Example 4

Example 17.1

Reaction of Oxidized Erythropoietin with the Reaction Product of Example 14.1

Oxidized EPO (1.055 µg/µl) in 20 mM PBS buffer was adjusted to pH 5.3 with 5 M sodium acetate buffer, pH 5.2. To 19 µl of the EPO solution, 18 µl of a solution of the HES derivate as produced according to example 14.1 (MW 18 kD; 18.7 µg/µl in 0.1 M sodium acetate buffer, pH 5.2) was added, and the mixture was incubated for 16 h at 25° C. After lyophilisation, the crude product was analyzed by SDS-Page with NuPAGE 10% Bis-Tris Gels/MOPS buffer (Invitrogen, Carlsbad, Calif., USA) as described in the instructions given by Invitrogen. The gel is stained with Roti-Blue Coomassie staining reagent (Roth, Karlsruhe, D) overnight.

The experimental result is shown in FIG. 3. A successful conjugation is indicated by the migration of the protein band to higher molecular weights. The increased bandwidth is due to the molecular weight distribution of the HES derivatives used and the number of HES derivatives linked to the protein.

Example 17.2

Reaction of Oxidized Erythropoietin with the Reaction Product of Example 14.3

Oxidized EPO (1.055 μg/μl) in 20 mM PBS buffer was adjusted to pH 5.3 with 5 M sodium acetate buffer, pH 5.2. To 19 μl of the EPO solution, 18 μl of a solution of the HES derivate as produced according to example 14.3 (MW 18 kD; 18.7 μg/μl in 0.1 M sodium acetate buffer, pH 5.2) was added, and the mixture was incubated for 16 h at 25° C. After lyophilisation, the crude product was analyzed by SDS-Page with NuPAGE 10% Bis-Tris Gels/MOPS buffer (Invitrogen; Carlsbad, Calif., USA) as described in the instructions given by Invitrogen.

Example 17.3

Reaction of Oxidized Erythropoietin with the Reaction Product of Example 14.4

Oxidized EPO (1.055 μg/μl) in 20 mM PBS buffer was adjusted to pH 5.3 with 5 M sodium acetate buffer, pH 5.2. To 19 μl of the EPO solution, 18 μl of a solution of the HES derivate as produced according to example 14.4 (MW 18 kD; 18.7 μg/μl in 0.1 M sodium acetate buffer, pH 5.2) was added, and the mixture was incubated for 16 h at 25° C. After lyophilisation, the crude product was analyzed by SDS-Page with NuPAGE 10% Bis-Tris Gels/MOPS buffer (Invitrogen, Carlsbad, Calif., USA) as described in the instructions given by Invitrogen. The gel is stained with Roti-Blue Coomassie staining reagent (Roth, Karlsruhe, D) overnight.

The experimental result is shown in FIG. 4. A successful conjugation is indicated by the migration of the protein band to higher molecular weights. The increased bandwidth is due to the molecular weight distribution of the HES derivatives used and the number of HES derivatives linked to the protein.

Example 17.4

Reaction of Oxidized Erythropoietin with the Reaction Product of Example 15.1

Oxidized EPO (1.055 μg/μl) in 20 mM PBS buffer was adjusted to pH 5.3 with 5 M sodium acetate buffer, pH 5.2. To 19 μl of the EPO solution, 18 μl of a solution of the HES derivate as produced according to example 15.1 (MW 10 kD; 18.7 μg/μl in 0.1 M sodium acetate buffer, pH 5.2) was added, and the mixture was incubated for 16 h at 25° C. After lyophilisation, the crude product was analyzed by SDS-Page with NuPAGE 10% Bis-Tris Gels/MOPS buffer (Invitrogen, Carlsbad, Calif., USA) as described in the instructions given by Invitrogen. The gel is stained with Roti-Blue Coomassie staining reagent (Roth, Karlsruhe, D) overnight.

The experimental result is shown in FIG. 5. A successful conjugation is indicated by the migration of the protein band to higher molecular weights. The increased bandwidth is due to the molecular weight distribution of the HES derivatives used and the number of HES derivatives linked to the protein.

Example 17.5

Reaction of Oxidized Erythropoietin with the Reaction Product of Example 15.2

Oxidized EPO (1.055 μg/μl) in 20 mM PBS buffer was adjusted to pH 5.3 with 5 M sodium acetate buffer, pH 5.2. To 19 μl of the EPO solution, 18 μl of a solution of the HES derivate as produced according to example 15.1 (MW 10 kD; 18.7 μg/μl in 0.1 M sodium acetate buffer, pH 5.2) was added, and the mixture was incubated for 16 h at 25° C. After lyophilisation, the crude product was analyzed by SDS-Page with NuPAGE 10% Bis-Tris Gels/MOPS buffer (Invitrogen, Carlsbad, Calif., USA) as described in the instructions given by Invitrogen. The gel is stained with Roti-Blue Coomassie staining reagent (Roth, Karlsruhe, D) overnight.

The experimental result is shown in FIG. 5. successful conjugation is indicated by the migration of the protein band to higher molecular weights. The increased bandwidth is due to the molecular weight distribution of the HES derivatives used and the number of HES derivatives linked to the protein.

Example 18

Formation of Thio-EPO by Reduction of Erythropoietin 241.5 μg erythropoietin (EPO-GT-1, see Example 20) in 500 μl of a 0.1 M sodium borate buffer, 5 mM EDTA, 10 mM DTT (Lancaster, Morcambe, UK), pH 8.3, were incubated for 1 h at 37° C. The DTT was removed by centrifugal filtration with a VIVASPIN 0.5 ml concentrator, 10 KD MWCO (VIVASCIENCE, Hannover, D) at 13,000 rpm, subsequent washing 3 times with the borate buffer and twice with a phosphate buffer (0.1 M, 9.15 M NaCl, 50 mM EDTA, pH 7.2).

Example 19

Conjugation of Hydroxyethyl Starch Derivatives with Thio-Erythropoietin Using a Crosslinking Compound In each of the following examples, N-(alpha-maleimidoacetoxy) succinimide ester (AMAS)

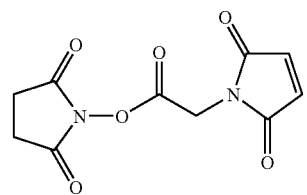 [SMILES: O=C(CN1C(=O)C=CC1=O)ON1C(=O)CCC1=O]

was used as crosslinking compound.

Example 19.1

Reaction of Thio-Erythropoietin with the Reaction Product of Example 14.1 and the Crosslinking Compound To 50 nmol HES derivate as produced according to example 14.1 and dissolved in 200 μl of a 0.1 M sodium phosphate buffer (0.1 M, 9.15 M NaCl, 50 mM EDTA, pH 7.2), 10 μl of a solution of 2.5 μmol AMAS (Sigma Aldrich, Taufkirchen, D) in DMSO were added. The clear solution was incubated for 80 min at 25° C. and 20 min at 40° C. Remaining AMAS was removed by centrifugal filtration with a VIVASPIN 0.5 ml concentrator, 5 KD MWCO (VIVASCIENCE, Hannover, D) at 13,000 rpm, washing 4 times and 30 min with the phosphate buffer.

To the residual solution, 15 μg of ThioEPO as produced according to example 18 (1 μg/μl in phosphate buffer) were added, and the mixture was incubated for 16 h at 25° C. After lyophilisation, the crude product was analysed by SDS-Page with NuPAGE 10% Bis-Tris Gels/MOPS buffer (Invitrogen, Carlsbad, USA) as described in the instructions given by Invitrogen. The gel is stained with Roti-Blue Coomassie staining reagent (Roth, Karlsruhe, D) overnight.

The experimental result is shown in FIG. 6. A successful conjugation is indicated by the migration of the protein band to higher molecular weights. The increased bandwidth is due to the molecular weight distribution of the HES derivatives used and the number of HES derivatives linked to the protein.

Example 19.2

Reaction of Thio-Erythropoietin with the Reaction Product of Example 14.2 and the Crosslinking Compound To 50 mmol HES derivate as produced according to example 14.2 and dissolved in 200 μl of a 0.1 M sodium phosphate buffer (0.1 M, 9.15 M NaCl, 50 mm EDTA, pH 7.2), 10 μl of a solution of 2.5 μmol AMAS (Sigma Aldrich, Taufkirchen, D) in DMSO were added. The clear solution was incubated for 80 min at 25° C. and 20 min at 40° C. Remaining AMAS was removed by centrifugal filtration with a VIVASPIN 0.5 ml concentrator, 5 KD MWCO (VIVASCIENCE, Hannover, D) at 13,000 rpm, washing 4 times and 30 min with the phosphate buffer.

To the residual solution, 15 μg of ThioEPO as produced according to example 18 (1 μg/μl in phosphate buffer) were added, and the mixture was incubated for 16 h at 25° C. After lyophilisation, the crude product was analysed by SDS-Page with NuPAGE 10% Bis-Tris Gels/MOPS buffer (Invitrogen, Carlsbad, USA) as described in the instructions given by Invitrogen. The gel is stained with Roti-Blue Coomassie staining reagent (Roth, Karlsruhe, D) overnight.

The experimental result is shown in FIG. 7. A successful conjugation is indicated by the migration of the protein band to higher molecular weights. The increased bandwidth is due to the molecular weight distribution of the HES derivatives used and the number of HES derivatives linked to the protein.

Example 19.3

Reaction of Thio-Erythropoietin with the Reaction Product of Example 14.3 and the Crosslinking Compound To 50 nmol HES derivate as produced according to example 14.3 and dissolved in 200 μl of a 0.1 M sodium phosphate buffer (0.1 M, 9.15 M NaCl, 50 mM EDTA, pH 7.2), 10 μl of a solution of 2.5 μmol AMAS (Sigma Aldrich, Taufkirchen, D) in DMSO were added. The clear solution was incubated for 80 min at 25° C. and 20 min at 40° C. Remaining AMAS was removed by centrifugal filtration with a VIVASPIN 0.5 ml concentrator, 5 KD MWCO (VIVASCIENCE, Hannover, D) at 13,000 rpm, washing 4 times and 30 min with the phosphate buffer.

To the residual solution, 15 μg of ThioEPO as produced according to example 18 (1 μg/μl in phosphate buffer) were added, and the mixture was incubated for 16 h at 25° C. After lyophilisation, the crude product was analysed by SDS-Page with NuPAGE 10% Bis-Tris Gels/MOPS buffer (Invitrogen, Carlsbad, USA) as described in the instructions given by Invitrogen. The gel is stained with Roti-Blue Coomassie staining reagent (Roth, Karlsruhe, D) overnight.

The experimental result is shown in FIG. 7. A successful conjugation is indicated by the migration of the protein band to higher molecular weights. The increased bandwidth is due to the molecular weight distribution of the HES derivatives used and the number of HES derivatives linked to the protein.

Example 19.4

Reaction of Thio-Erythropoietin with the Reaction Product of Example 14.4 and the Crosslinking Compound To 50 nmol HES derivate as produced according to example 14.4 and dissolved in 200 μl of a 0.1 M sodium phosphate buffer (0.1 M, 9.15 M NaCl, 50 mM EDTA, pH 7.2), 10 μl of a solution of 2.5 μmol AMAS (Sigma Aldrich, Taufkirchen, D) in DMSO were added. The clear solution was incubated for 80 min at 25° C. and 20 min at 40° C. Remaining AMAS was removed by centrifugal filtration with a VIVASPIN 0.5 ml concentrator, 5 KD MWCO (VIVASCIENCE, Hannover, D) at 13,000 rpm, washing 4 times and 30 min with the phosphate buffer.

To the residual solution, 15 μg of ThioEPO as produced according to example 18 (1 μg/μl in phosphate buffer) were added, and the mixture was incubated for 16 h at 25° C. After lyophilisation, the crude product was analysed by SDS-Page with NuPAGE 10% Bis-Tris Gels/MOPS buffer (Invitrogen, Carlsbad, USA) as described in the instructions given by Invitrogen. The gel is stained with Roti-Blue Coomassie staining reagent (Roth, Karlsruhe, D) overnight.

The experimental result is shown in FIG. 6. A successful conjugation is indicated by the migration of the protein band to higher molecular weights. The increased bandwidth is due to the molecular weight distribution of the HES derivatives used and the number of HES derivatives linked to the protein.

Example 19.5

Reaction of Thio-Erythropoietin with the Reaction Product of Example 13.1 and the Crosslinking Compound To 50 nmol HES derivate as produced according to example 13.1, at incubation conditions of 80° C. and 17 h as well as of 25° C. and 3 d, and dissolved in 200 μl of a 0.1 M sodium phosphate buffer (0.1 M, 9.15 M NaCl, 50 mM EDTA, pH 7.2), 10 μl of a solution of 2.5 μmol AMAS (Sigma Aldrich, Taufkirchen, D) in DMSO were added. The clear solution was incubated for 80 min at 25° C. and 20 min at 40° C. Remaining AMAS was removed by centrifugal filtration with a VIVASPIN 0.5 ml concentrator, 5 KD MWCO (VIVA- SCIENCE, Hannover, D) at 13,000 rpm, washing 4 times and 30 min with the phosphate buffer.

To the residual solution, 15 µg of ThioEPO as produced according to example 18 (1 µg/µl in phosphate buffer) were added, and the mixture was incubated for 16 h at 25° C. After lyophilisation, the crude product was analysed by SDS-Page with NuPAGE 10% Bis-Tris Gels/MOPS buffer (Invitrogen, Carlsbad, USA) as described in the instructions given by Invitrogen. The gel is stained with Roti-Blue Coomassie staining reagent (Roth, Karlsruhe, D) overnight.

The experimental result is shown in FIG. 7. A successful conjugation is indicated by the migration of the protein band to higher molecular weights. The increased bandwidth is due to the molecular weight distribution of the HES derivatives used and the number of HES derivatives linked to the protein.

Example 19.6

Reaction of Thio-Erythropoietin with the Reaction Product of Example 13.3 and the Crosslinking Compound To 50 mmol HES derivate as produced according to example 13.3, at incubation conditions of 80° C. and 17 h as well as of 25° C. and 3 d, and dissolved in 200 µl of a 0.1 M sodium phosphate buffer (0.1 M, 9.15 M NaCl, 50 mM EDTA, pH 7.2), 10 µl of a solution of 2.5 µmol AMAS (Sigma Aldrich, Taufkirchen, D) in DMSO were added. The clear solution was incubated for 80 min at 25° C. and 20 min at 40° C. Remaining AMAS was removed by centrifugal filtration with a VIVASPIN 0.5 ml concentrator, 5 KD MWCO (VIVASCIENCE, Hannover, D) at 13,000 rpm, washing 4 times and 30 min with the phosphate buffer.

To the residual solution, 15 µg of ThioEPO as produced according to example 18 (1 µg/µl in phosphate buffer) were added, and the mixture was incubated for 16 h at 25° C. After lyophilisation, the crude product was analysed by SDS-Page with NuPAGE 10% Bis-Tris Gels/MOPS buffer (Invitrogen, Carlsbad, USA) as described in the instructions given by Invitrogen. The gel is stained with Roti-Blue Coomassie staining reagent (Roth, Karlsruhe, D) overnight.

The experimental result is shown in FIG. 7. A successful conjugation is indicated by the migration of the protein band to higher molecular weights. The increased bandwidth is due to the molecular weight distribution of the HES derivatives used and the number of HES derivatives linked to the protein.

Example 19.7

Reaction of Thio-Erythropoietin with the Reaction Product of Example 15.1 and the Crosslinking Compound To 50 nmol HES derivate, produced according to Example 15.1 and dissolved in 200 µl phosphate buffer (0.1 M, 9.15 M NaCl, 50 mM EDTA, pH 7.2), 10 µl of a solution of 2.5 µmol AMAS (Sigma Aldrich, Taufkirchen, D) in DMSO was added, and the clear solution was incubated for 80 min at 25° C. and 20 min at 40° C. The AMAS was removed by centrifugal filtration with a VIVASPIN 0.5 ml concentrator, 5 KD MWCO (VIVASCIENCE, Hannover, Germany) at 13,000 rpm and washing 4 times for 30 min with the phosphate buffer.

To the residual solution, 15 µg Thio-EPO as produced according to example 18 (1 µg/µl in phosphate buffer) were added, and the mixture was incubated for 16 h at 25° C. After lyophilisation, the crude product was analysed by SDS-Page with NuPAGE 10% Bis-Tris Gels/MOPS buffer (Invitrogen, Carlsbad, Calif., USA) as described in the instructions given by Invitrogen. The gel is stained with Roti-Blue Coomassie staining reagent (Roth, Karlsruhe, D) overnight.

The experimental result is shown in FIG. 8. A successful conjugation is indicated by the migration of the protein band to higher molecular weights. The increased bandwidth is due to the molecular weight distribution of the HES derivatives used and the number of HES derivatives linked to the protein.

Example 19.8

Reaction of Thio-Erythropoietin with the Reaction Product of Example 15.2 and the Crosslinking Compound To 50 mmol HES derivate, produced according to Example 15.2 and dissolved in 200 µl phosphate buffer (0.1 M, 9.15 M NaCl, 50 mM EDTA, pH 7.2), 10 µl of a solution of 2.5 µmol AMAS (Sigma Aldrich, Taufkirchen, D) in DMSO was added, and the clear solution was incubated for 80 min at 25° C. and 20 min at 40° C. The AMAS was removed by centrifugal filtration with a VIVASPIN 0.5 ml concentrator, 5 KD MWCO (VIVASCIENCE, Hannover, Germany) at 13,000 rpm and washing 4 times for 30 min with the phosphate buffer.

To the residual solution, 15 µg Thio-EPO as produced according to example 18 (1 µg/µl in phosphate buffer) were added, and the mixture was incubated for 16 h at 25° C. After lyophilisation, the crude product was analysed by SDS-Page with NuPAGE 10% Bis-Tris Gels/MOPS buffer (Invitrogen, Carlsbad, Calif., USA) as described in the instructions given by Invitrogen. The gel is stained with Roti-Blue Coomassie staining reagent (Roth, Karlsruhe, D) overnight.

The experimental result is shown in FIG. 8. A successful conjugation is indicated by the migration of the protein band to higher molecular weights. The increased bandwidth is due to the molecular weight distribution of the HES derivatives used and the number of HES derivatives linked to the protein.

Example 19.9

Reaction of Thio-Erythropoietin with the Reaction Product of Example 15.3 and the Crosslinking Compound To 50 mmol HES derivate, produced according to Example 15.3 and dissolved in 200 µl phosphate buffer (0.1 M, 9.15 M NaCl, 50 mM EDTA, pH 7.2), 10 µl of a solution of 2.5 mmol AMAS (Sigma Aldrich, Taufkirchen, D) in DMSO was added, and the clear solution was incubated for 80 min at 25° C. and 20 min at 40° C. The AMAS was removed by centrifugal filtration with a VIVASPIN 0.5 ml concentrator, 5 KD MWCO (VIVASCIENCE, Hannover, Germany) at 13,000 rpm and washing 4 times for 30 min with the phosphate buffer.

To the residual solution, 15 µg Thio-EPO as produced according to example 18 (1 µg/µl in phosphate buffer) were added, and the mixture was incubated for 16 h at 25° C. After lyophilisation, the crude product was analysed by SDS-Page with NuPAGE 10% Bis-Tris Gels/MOPS buffer (Invitrogen, Carlsbad, Calif., USA) as described in the instructions given by Invitrogen. The gel is stained with Roti-Blue Coomassie staining reagent (Roth, Karlsruhe, D) overnight.

The experimental result is shown in FIG. 8. A successful conjugation is indicated by the migration of the protein band to higher molecular weights. The increased bandwidth is due to the molecular weight distribution of the HES derivatives used and the number of HES derivatives linked to the protein.

Example 19.10

Reaction of Thio-Erythropoietin with the Reaction Product of Example 15.4 and the Crosslinking Compound To 50 nmol HES derivate, produced according to Example 15.4 and dissolved in 200 µl phosphate buffer (0.1 M, 9.15 M NaCl, 50 mM EDTA, pH 7.2), 10 µl of a solution of 2.5 µmol AMAS (Sigma Aldrich, Taufkirchen, D) in DMSO was added, and the clear solution was incubated for 80 min at 25° C. and 20 min at 40° C. The AMAS was removed by centrifugal filtration with a VIVASPIN 0.5 ml concentrator, 5 KD MWCO (VIVASCIENCE, Hannover, Germany) at 13,000 rpm and washing 4 times for 30 min with the phosphate buffer.

To the residual solution, 15 µg Thio-EPO as produced according to example 18 (1 µg/µl in phosphate buffer) were added, and the mixture was incubated for 16 h at 25° C. After lyophilisation, the crude product was analysed by SDS-Page with NuPAGE 10% Bis-Tris Gels/MOPS buffer (Invitrogen, Carlsbad, Calif., USA) as described in the instructions given by Invitrogen. The gel is stained with Roti-Blue Coomassie staining reagent (Roth, Karlsruhe, D) overnight.

The experimental result is shown in FIG. 8. A successful conjugation is indicated by the migration of the protein band to higher molecular weights. The increased bandwidth is due to the molecular weight distribution of the HES derivatives used and the number of HES derivatives linked to the protein.

Example 19.11

Reaction of Thio-Erythropoietin with the Reaction Product of Example 15.5 and the Crosslinking Compound To 50 mmol HES derivate, produced according to Example 15.5 and dissolved in 200 µl phosphate buffer (0.1 M, 9.15 M NaCl, 50 mM EDTA, pH 7.2), 10 µl of a solution of 2.5 µmol AMAS (Sigma Aldrich, Taufkirchen, D) in DMSO was added, and the clear solution was incubated for 80 min at 25° C. and 20 min at 40° C. The AMAS was removed by centrifugal filtration with a VIVASPIN 0.5 ml concentrator, 5 KD MWCO (VIVASCIENCE, Hannover, Germany) at 13,000 rpm and washing 4 times for 30 min with the phosphate buffer.

To the residual solution, 15 µg Thio-EPO as produced according to example 18 (1 µg/µl in phosphate buffer) were added, and the mixture was incubated for 16 h at 25° C. After lyophilisation, the crude product was analysed by SDS-Page with NuPAGE 10% Bis-Tris Gels/MOPS buffer (Invitrogen, Carlsbad, Calif., USA) as described in the instructions given by Invitrogen. The gel is stained with Roti-Blue Coomassie staining reagent (Roth, Karlsruhe, D) overnight.

The experimental result is shown in FIG. 8. A successful conjugation is indicated by the migration of the protein band to higher molecular weights. The increased bandwidth is due to the molecular weight distribution of the HES derivatives used and the number of HES derivatives linked to the protein.

Example 19.12

Reaction of Thio-Erythropoietin with the Reaction Product of Example 15.6 and the Crosslinking Compound To 50 mmol HES derivate, produced according to Example 15.6 and dissolved in 200 µl phosphate buffer (0.1 M, 9.15 M NaCl, 50 mM EDTA, pH 7.2), 10 µl of a solution of 2.5 µmol AMAS (Sigma Aldrich, Taufkirchen, D) in DMSO was added, and the clear solution was incubated for 80 min at 25° C. and 20 min at 40° C. The AMAS was removed by centrifugal filtration with a VIVASPIN 0.5 ml concentrator, 5 KD MWCO (VIVASCIENCE, Hannover, Germany) at 13,000 rpm and washing 4 times for 30 min with the phosphate buffer.

To the residual solution, 15 µg Thio-EPO as produced according to example 18 (1 µg/µl in phosphate buffer) were added, and the mixture was incubated for 16 h at 25° C. After lyophilisation, the crude product was analysed by SDS-Page with NuPAGE 10% Bis-Tris Gels/MOPS buffer (Invitrogen, Carlsbad, Calif., USA) as described in the instructions given by Invitrogen. The gel is stained with Roti-Blue Coomassie staining reagent (Roth, Karlsruhe, D) overnight.

The experimental result is shown in FIG. 8. A successful conjugation is indicated by the migration of the protein band to higher molecular weights. The increased bandwidth is due to the molecular weight distribution of the HES derivatives used and the number of HES derivatives linked to the protein.

Example 20

Preparative Production of HES-EPO Conjugates

Summary

HES-EPO conjugates were synthesized by coupling of HES derivatives (average mw of 18,000 Dalton; hydroxyethyl substitution degree of 0.4) to the partially (mild periodate) oxidized sialic acid residues on the oligosaccharide chains of recombinant human EPO. Based on carbohydrate structural analysis the modifications introduced did not affect the structural integrity of the core oligosaccharide chains since MALDI/TOF-MS of the mild acid treated HES-modified glycans revealed intact neutral N-acetyllactosamine-type chains which were indistinguishable from those observed in unmodified EPO product. The results obtained indicate that at least 3 modified HES-residues are attached per EPO molecule in the case of the EPO preparation which was subjected to modification without prior partial sialic acid removal. An EPO variant lacking about 50% of the sialic acid residues of the former protein showed a similar apparent high molecular weight mobility in SDS-PAGE (60-110 KDa vs 40 KDa for the BRP EPO standard). The HES modified EPO is stable under standard ion-exchange chromatography conditions at room temperature at pH 3-10.

The EPO-bioassay in the normocythaemic mouse system indicates that the HES-modified EPO has 2.5-3.0 fold higher specific activity (IU/mg) in this assay when compared to the International BRP EPO reference standard based on protein determination using the UV absorption value from the European Pharmacopeia and an RP-HPLC EPO protein determination method calibrated against the BRP EPO standard preparation.

Example 20.1

Materials and Methods (a) Liberation of N-linked Oligosaccharides by Digestion with N-Glycosidase Samples were incubated with 25 units (according to manufacturer's specification, Roche Diagnostics, Germany) of recombinant PNGase F over night at 37° C. Complete digestion was monitored by the specific mobility shift of the protein in SDS-PAGE. The released N-glycans were separated from the polypeptide by addition of 3 volumes of cold 100% ethanol and incubation at −20° C. for at least 2 hours (Schroeter S et al., 1999). The precipitated protein was removed by centrifugation for 10 minutes at 4° C. at 13000 rpm. The pellet was then subjected to two additional washes with 500 µl of ice-cold 75% ethanol. The oligosaccharides in the pooled supernatants were dried in a vacuum centrifuge (Speed Vac concentrator, Savant Instruments Inc., USA). The glycan samples were desalted using Hypercarb cartridges (25 mg or 100 mg of HyperCarb) as follows prior to use: the columns were washed with 3×500 µl of 80% acetonitrile (v/v) in 0.1% TFA followed by washes with 3×500 µl of water. The samples were diluted with water to a final volume of 300 µl-600 µl before loading onto the cartridge which then was rigorously washed with water. Oligosaccharides were eluted with 1.2 ml (25 mg cartridges; 1.8 ml in the case of 100 mg cartridges) 25% acetonitrile in water containing 0.1% trifluoroacetic acid (v/v). The eluted oligosaccharides were neutralized with 2 M $NH_4OH$ and were dried in a Speed Vac concentrator. In some cases desalting of N-glycosidase released oligosaccharides was performed by adsorption of the digestion mixture from samples <100 µg of total (glyco)protein onto 100 mg Hypercarb cartridges.

(b) Analysis of Oligosaccharides by Matrix-Assisted Laser Desorption/Ionization Time-of-Flight Mass-Spectrometry (MALDI/TOF/TOF-MS)

A Bruker ULTRAFLEX time-of-flight (TOF/TOF) instrument was used: native desialylated oligosaccharides were analyzed using 2,5-dihydroxybenzoic acid as UV-absorbing material in the positive as well as in the negative ion mode using the reflectron in both cases. For MS-MS analyses, selected parent ions were subjected to laser induced dissociation (LID) and the resulting fragment ions separated by the second TOF stage (LIFT) of the instrument. Sample solutions of 1 µl and an approximate concentration of 1-10 pmol·µl$^{-1}$ were mixed with equal amounts of the respective matrix. This mixture was spotted onto a stainless steel target and dried at room temperature before analysis.

Example 20.2

Preparation and Characterization of Recombinant Human EPO (EPO-GT-1)

EPO was expressed from recombinant CHO cells as described (Mueller P P et al., 1999, Dorner A J et al., 1984) and the preparations were characterized according to methods described in the Eur. Phar. (*Ph. Eur.* 4, *Monography* 01/2002:1316: Erythropoietin concentrated solution). The final product had a sialic acid content of 12 nMol (+/−1.5 nMol) per nMol of protein. The structures of N-linked oligosaccharides were determined by HPAEC-PAD and by MALDI/TOF-MS as described (Nimtz et al., 1999, Grabenhorst, 1999). The EPO preparations that were obtained contained di-, tri- and tetrasialylated oligosaccharides (2-12%, 15-28% and 60-80%, respectively, sulphated and pentasialylated chains were present in small amounts). The overall glycosylation characteristics of EPO preparations were similar to that of the international BRP EPO standard preparation.

The isoelectric focusing pattern of the recombinant EPO was comparable to that of the international BRP Reference EPO standard preparation showing the corresponding isoforms. 25% of the EPO protein lacked O-glycosylation at $Ser_{126}$ of the polypeptide chain.

Example 8.3

Preparation of Partially Desialylated EPO Forms

EPO GT-1 protein (2.84 mg/ml) was heated to 80° C. in 20 mM Na-phosphate buffer pH 7.0 and then 100 µl of 1 N $H_2SO_4$ was added per 1 ml of the EPO solution; incubation was continued for 5 min, 10 min and 60 min, respectively, yielding EPO preparations of different degree of sialylation. Quantitation of oligosaccharides with 0-4 sialic acids was performed after liberation of oligosaccharides with polypeptide N-glycosidase and isolation of N-linked chains was performed by desalting using Hypercarb cartridges (25 mg HyperSep Hypercarb; Thermo-Hypersil-Keystone, UK). EPO preparations were neutralized by addition of 1 N NaOH and were frozen in liquid $N_2$ and were stored at −20° C. until further use.

Example 20.4

Periodate Oxidation of Sialylated EPO Forms

To 10 mg of untreated or mild acid treated EPO dissolved in 3.5 ml of 20 mM Na-phosphate buffer pH 7.0 was added 1.5 ml of 0.1 M Na-acetate buffer pH 5.5 and the mixture was cooled to 0° C. in an ice-bath; 500 µl of 10 mM Na-periodate was added and the reaction mixture was kept in the dark for 60 min at 0° C. Then 10 µl of glycerol was added and incubation was continued for further 10 min in the dark. The partially oxidized EPO forms were separated from reagents by desalting using VIVASPIN concentrators (10,000. MWCO, PES Vivascience AG, Hannover, Germany) according to manufacturer's recommendation at 3000 rpm in a laboratory centrifuge equipped with a fixed angle rotor. After freezing in liquid nitrogen the EPO preparations were stored in a final volume of 4 ml at −20° C.

100 µg aliquots of the partially oxidized EPO preparation were subjected to N-glycosidase treatment and oligosaccharides were isolated using Hypercarb cartridges as described. Oligosaccharides were desialylated by mild acid treatment and were analyzed by HPAEC-PAD and their retention times were compared to those of authentic standard oligosaccharides as described (Nimtz et al., 1990 and 1993).

Example 20.5

Reduction of EPO Disulfides with Dithioerythritol 5 mg of EPO-GT-1 was incubated in 5 ml of 0.1 M Tris/HCl buffer pH 8.1 in the presence of 30 mM dithioerythritol (DTT) at 37° C. for 60 minutes; removal of DTT was achieved by using a Vivaspin concentrator at 4° C., 4 cycles of buffer exchange. The final reduced EPO preparation was frozen in liquid nitrogen and stored at −20° C. in 50 mM Na-acetate buffer pH 5.5.

Example 20.6

EPO Protein Determination

Quantitative determination of EPO protein was performed by measuring UV absorption at 280 nm according to the Eur. Phar. (European Pharmacopoeia 4, Monography 01/2002: 1316: erythropoietin concentrated solution) in a cuvette with 1 cm path length. In addition, EPO was quantitated by applying a RP-HPLC method using a RP-C4 column (Vydac Protein C4, Cat.# 214TP5410, Grace Vydac, Calif., US); the HPLC method was calibrated using the erythropoietin BRP 1 reference standard (European Pharmacopeia, Conseil de l'Europe B.P. 907-F67029, Strasbourg Cedex 1).

Example 20.7

Oxidation of Desialylated EPO with Galactose Oxidase 4.485 mg of completely desialylated EPO was incubated in 20 mM Na-phosphate buffer pH 6.8 in the presence of 16 µl catalase (6214 units/200 ml) and 80 µl of galactose oxidase (2250 units/ml from *Dactylium dendroides* (Sigma-Aldrich, Steinheim, Germany); incubation at 37° C. was over night; 2 times 20 µl of galactose oxidase was added after 4 hours and after 8 hours after starting of the incubation.

Example 20.8

Preparation of EPO Samples for Bioassays

Purification of EPO from Incubations of Periodate- or Galactose-Oxidase-Oxidized EPO Protein Preparations with Activated HES Purification of EPO samples (removal of unreacted HES derivatives) was carried out at room temperature. The EPO incubation mixtures (approximately 5 mg of EPO protein) were diluted 1:10 with buffer A (20 mM N-morpholine propane sulfonic acid [MOPS/NaOH] in H$_2$O bidest, pH 8.0) and were applied to a column containing 3 ml Q-Sepharose HP (Pharmacia Code no. 17-1014-03, Lot no. 220211) equilibrated with 10 column volumes (CV) of buffer A by using a flow rate of 0.5 ml/min. The column was washed with 6-8 CV of buffer A (flow rate 0.8 ml/min) and elution was performed by using buffer B (20 mM morpholine ethane sulfonic acid [MES/NaOH], 0.5 M NaCl in H$_2$O bidest, pH 6.5) at a flow rate of 0.5 ml/min. EPO was detected by UV absorption at 280 nm and eluted in about 6 ml. The column was regenerated by using 3 CV of buffer C (20 mM MES, 1.5 M NaCl in H$_2$O adjusted to pH 6.5) and was re-equilibrated by using 10 CV of buffer A (flow rate 0.7 ml/min).

Buffer exchange of EPO eluates obtained from the Q-Sepharose step was performed using Vivaspin concentrators and phosphate buffered saline (PBS) with each 3 centrifugation cycles per sample; samples were adjusted to 2 ml with PBS and were stored at −20° C.

Only <25% of the partially desialylated and subsequently mild periodate oxidized EPO forms that were subjected to HES-modification were obtained from the Q-Sepharose eluate since under the conditions employed the basic EPO forms did not bind Q-Sepharose and were found in the flow-through together with nonreacted HES derivatives.

Example 20.9

High-pH Anion-Exchange Chromatography with Pulsed Amperometric Detection (HPAEC-PAD)

Purified native and desialylated oligosaccharides were analyzed by high-pH anion-exchange (HPAE) chromatography using a Dionex BioLC system (Dionex, USA) equipped with a CarboPac PA1 column (0.4×25 cm) in combination with a pulsed amperometric detector (PAD) (Schröter et al., 1999; Nimtz et al., 1999). Detector potentials (E) and pulse durations (T) were: E1: +50 mV, T1: 480 ms; E2: +500 mV, T2: 120 ms; E3: −500 mV, T3: 60 ms, and the output range was 500-1500 nA. The oligosaccharides were then injected onto the CarboPac PA1 column which was equilibrated with 100% solvent A. For desialylated oligosaccharides elution (flow rate: 1 ml·min$^{-1}$) was performed by applying a linear gradient (0-20%) of solvent B over a period of 40 min followed by a linear increase from 20-100% solvent B over 5 min. Solvent A was 0.2 M NaOH in bidistilled H$_2$O, solvent B consisted of 0.6 M NaOAc in solvent A. For native oligosaccharides the column was equilibrated with 100% solvent C (0.1 M NaOH in bidistilled H$_2$O) and elution (flow rate: 1 ml·min$^{-1}$) was performed by applying a linear gradient (0-35%) of solvent D over a period of 48 min followed by a linear increase from 35-100% solvent D over 10 min. Solvent D consisted of 0.6 M NaAc in solvent C.

Example 20.10

Monosaccharide Compositional Analysis of N-Glycans, HES-Modified N-Glycans and EPO Protein by GC-MS Monosaccharides were analyzed as the corresponding methyl glycosides after methanolysis, N-reacetylation and trimethylsilylation by GC/MS [Chaplin, M. F. (1982) A rapid and sensitive method for the analysis of carbohydrate. *Anal. Biochem.* 123, 336-341]. The analyses were performed on a Finnigan GCQ ion trap mass spectrometer (Finnigan MAT corp., San Jose, Calif.) running in the positive ion EI mode equipped with a 30 m DB5 capillary column. Temperature program: 2 min isotherm at 80° C., then 10 degrees min$^{-1}$ to 300° C.

Monosaccharides were identified by their retention time and characteristic fragmentation pattern. The uncorrected results of electronic peak integration were used for quantification. Monosaccharides yielding more than one peak due to anomericity and/or the presence of furanoid and pyranoid forms were quantified by adding all major peaks. 0.5 µg of myo-inositol was used as an internal standard compound.

Example 20.11

Results

Example 20.11(a)

Characterization of N-Glycans of Mild Acid Treated (Partially Desialylated) EPO-GT-1

Figure 9:
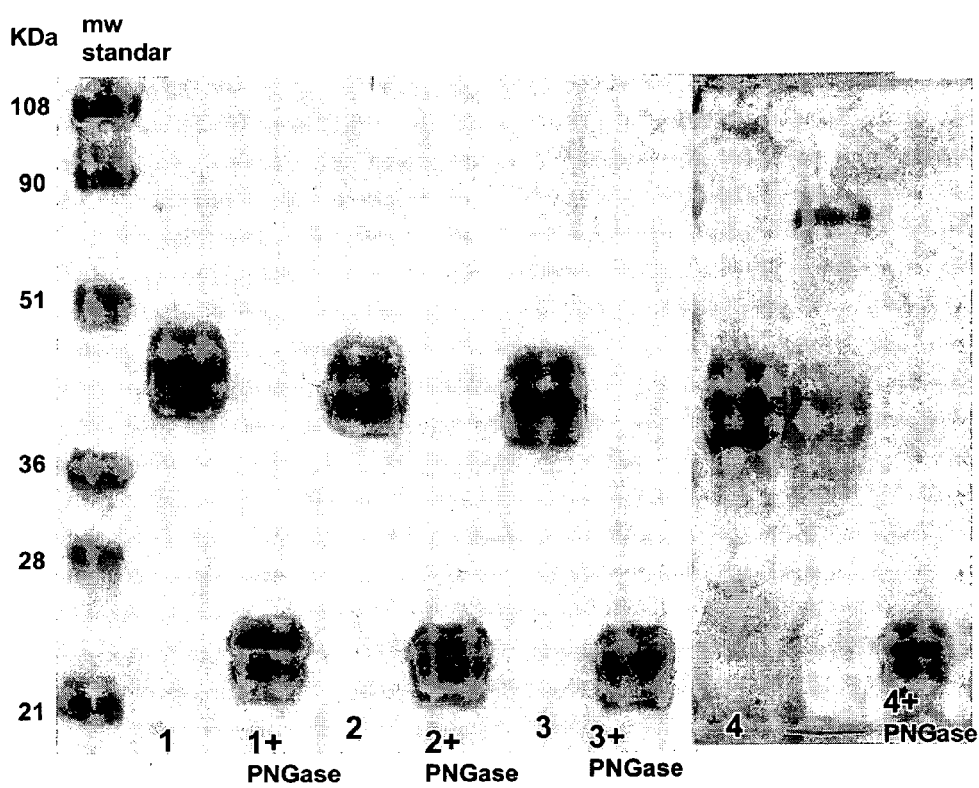
Figure 10:
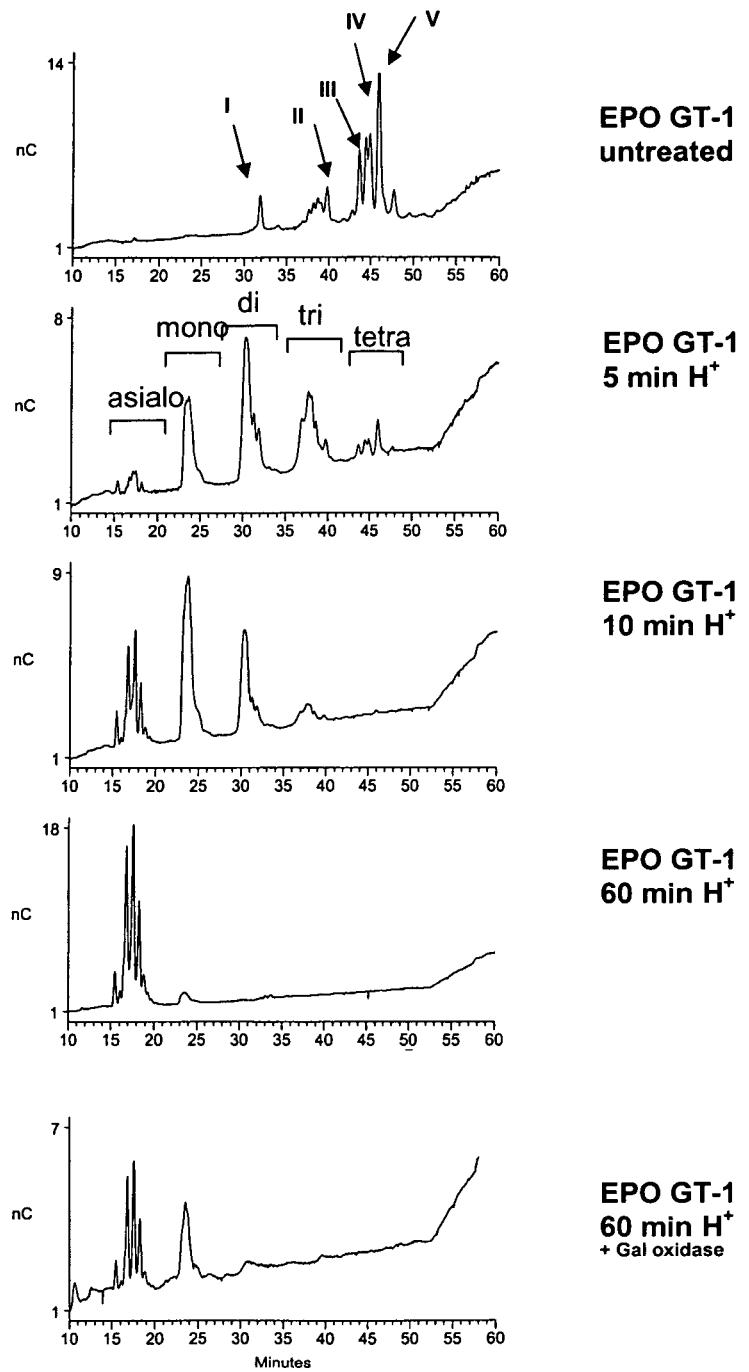
Figure 11:
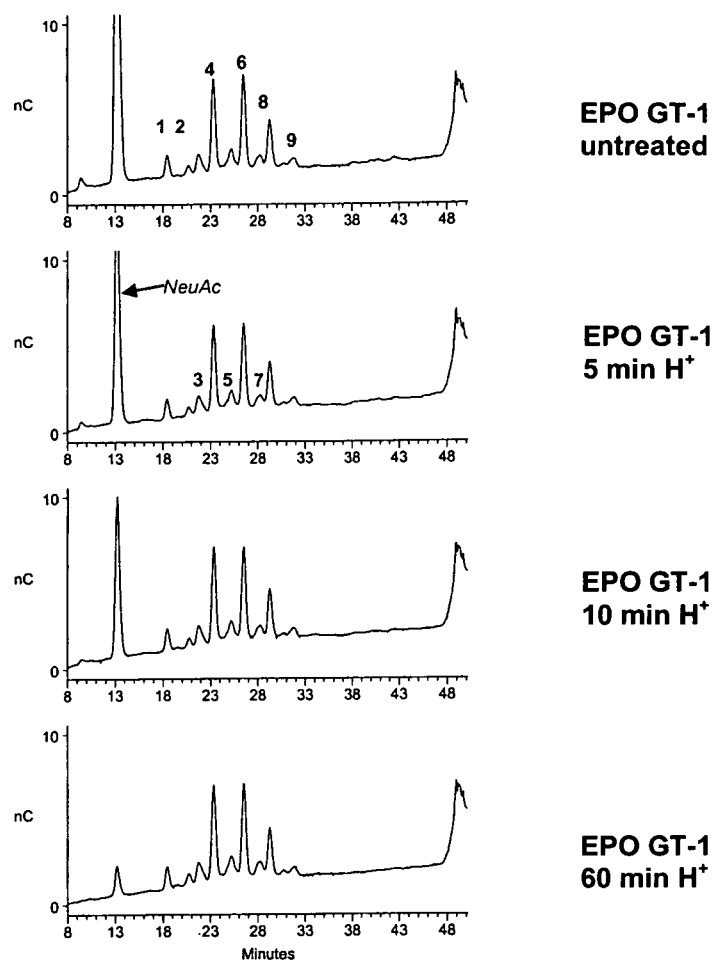

EPO-GT-1 preparations subjected to mild acid treatment for 5, 10 or 60 min. were analyzed by SDS-PAGE before and after liberation of N-linked oligosaccharides by incubation with N-glycosidase as shown in FIG. 9. N-linked oligosaccharides were subjected to HPAEC-PAD oligosaccharide mapping (FIG. 10). The untreated EPO-GT-1 contained >90% of N-linked oligosaccharides with 3 or 4 sialic acid residues whereas after 5 min. of incubation in the presence of mild acid <40% of carbohydrate chains had 3 or 4 sialic acid residues. HPAEC-PAD of the desialylated N-glycans revealed that the ratio of neutral oligosaccharides that were detected for the untreated EPO-GT-1 and remained stable in the preparations subjected to acid treatment for 5, 10 or 60 min. MALDI/TOF-MS of the desialylated glycans revealed that <90% of the proximal fucose was present after mild acid treatment of the protein.

Example 20.11(b)

Characterization of Periodate Treated EPO-GT-1

Figure 12:
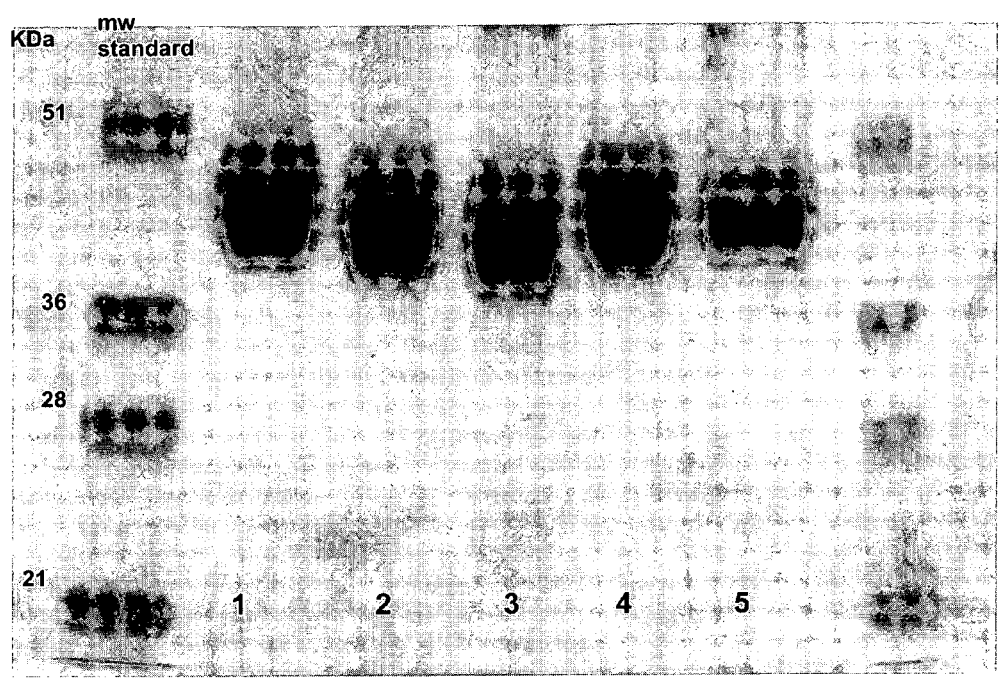

SDS-PAGE mobility of mild periodate treated EPO forms that were previously subjected to a 5 and 10 minute treatment with acid or were not treated are compared in FIG. 12. The conditions used for periodate oxidation of sialic acids did not change the SDS-PAGE pattern of EPO preparations (compare FIG. 9). Oxidation of sialic acids resulted in a shift of oligosaccharides in HPAEC-PAD analysis to earlier elution times (compare FIGS. 10 and 13).

Example 20.11(c)

Characterization of HES-Modified EPO Derivatives (aa) Time Course of HES Modification of EPO-GT-1-A with Hydroxylamine-Modified HES Derivative X, Produced According to Example 14.4

400 μg of hydroxylamine-modified HES derivative X was added to 20 μg of EPO-GT-1-A (mild periodate oxidized EPO, not acid hydrolyzed prior to mild periodate oxidation) in 20 μL of 0.5 M NaOAc buffer pH 5.5 and the reaction was stopped after 30 min, 2, 4, and 17 hours, respectively, by freezing samples in liquid nitrogen. Subsequently samples were stored at −20° C. until further analysis.

Figure 14:
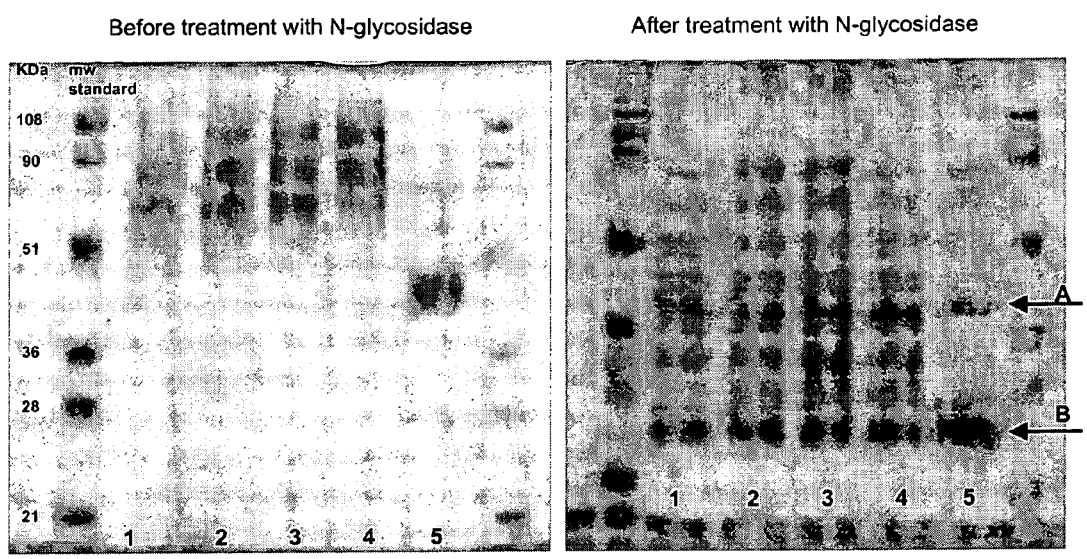

SDS-PAGE sample buffer was added and the samples were heated to 90° C. and applied onto SDS-gels. As shown in FIG. 14, increasing incubation times resulted in an increased shift towards higher molecular weight of the protein. After 17 hours of incubation in the presence of the hydroxylamine-modified HES derivative X a diffuse Coomassie stained protein band was detected migrating in an area between 60 and 11 KDa, based on the position of molecular weight standards (see left part of FIG. 14). Upon treatment with N-glycosidase most of the protein was shifted towards the position of de-N-glycosylated EPO (see FIG. 14, right gel; arrow A indicates migration position of N-glycosidase, arrow B indicates migration position of de-N-glycosylated EPO; the diffuse protein band visible in the region between the 28 KDa and 36 KDa molecular weight standards presumably represents EPO-forms which are modified by HES and the O-glycosylation site of the molecule. In view of the specificity of N-glycosidase we conclude from this result that in fact HES-modification occurs at the periodate oxidized sialic acid residues of glycans of the EPO protein.

(bb) Characterization of HES-EPO Conjugates

HES-EPO conjugates I (originating from EPO-GT-1 after mild periodate oxidation, i.e. from EPO-GT-1-A), II (resulting from EPO-GT-1 subjected to 5 min acid hydrolysis and mild periodate oxidation), III (resulting from EPO-GT-1 subjected to 10 min acid hydrolysis and mild periodate oxidation) were synthesized as described before. A control incubation (K) was included containing unmodified EPO-GT-1 under the same buffer conditions to which an equivalent amount of unmodified HES was added. The incubation mixtures were subjected to further purification for subsequent biochemical analysis of the HES-EPO derivatives.

Incubations HES-EPO conjugates I, II and III as well as the control incubation K were subjected to a Q-Sepharose purification step as described under "Material and Methods" (Example 20.8) in order to remove the excess of nonreacted HES-reagent which was expected in flow through of the ion-exchange column. Due to the high amounts of basic EPO forms contained in previously acid treated samples II and III we expected considerable amounts of modified EPO product from these incubations in the flow through. As is shown in FIG. 15, almost all of the EPO material from samples I was retained by Q-Sepharose column whereas only approximately 20-30% of the samples III and II was recovered in the fraction eluting with high salt concentration. All of the protein material from the incubations with HES derivative X, both in the flow-through and the fractions eluting with high salt, had apparent higher molecular weight in SDS-PAGE when compared to the control EPO.

Figure 16B:
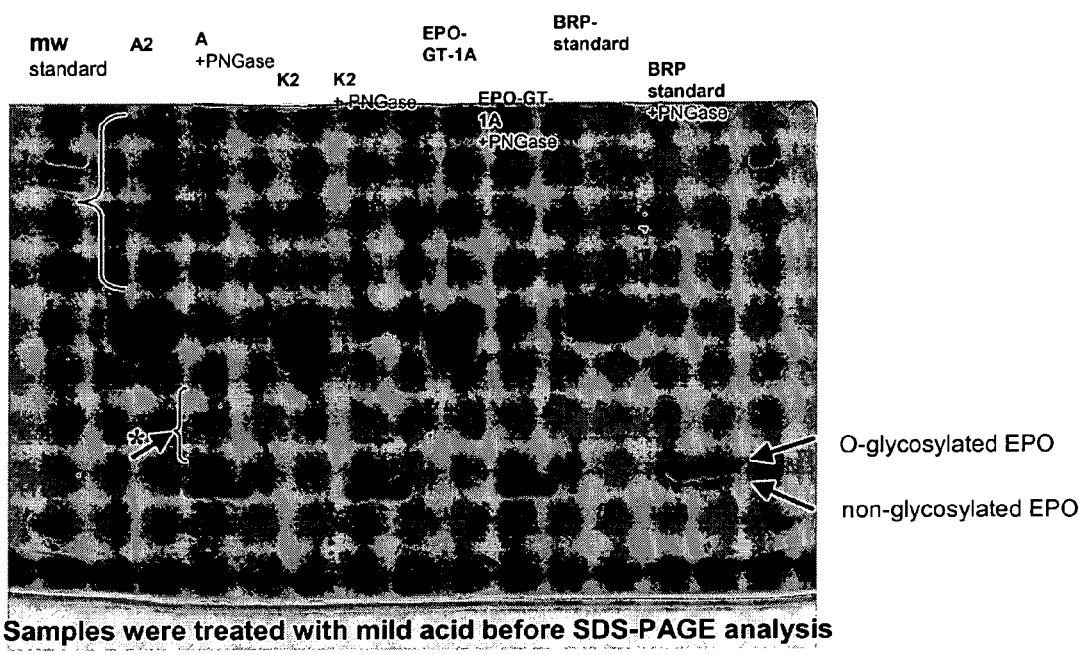

In order to characterize in more detail the HES-modified EPO sample A and K (see FIG. 13) were compared to periodate oxidized form EPO-GT-1-A. The samples were subjected to N-glycosidase treatment and as is depicted in FIGS. 16a and 16b the release of N-glycans resulted in the two low molecular weight bands at the position of the O-glycosylated and nonglycosylated EPO forms of the standard EPO preparation. In the case of sample A a further band migrating at the position of the 28 KDa mw standard was detected suggesting HES-modification at the O-glycan of this EPO variant (cf. Example 20.11(c)(aa)). This band (and also the heavily HES-modified high mw form of N-glycosylated EPO, see FIGS. 16a and 16b) disappeared after subjecting the samples to mild hydrolysis which is in agreement with the view that HES modification was achieved at the periodate oxidised sialic acid residues of erythropoietin.

Aliquots of the N-glycosidase incubation mixtures were hydrolyzed using conditions enabling the complete removal of sialic acids residues (and also the sialic acid linked HES derivative) from oligosaccharides; after neutralization, the mixtures were then absorbed onto small Hypercarb columns for their desalting. The columns were washed rigorously with water followed by elution of bound neutral oligosaccharides with 40% acetonitrile in $H_2O$ containing 0.1% of trifuluoacetic acid. The resulting oligosaccharides were subjected to MALDI/TOF-MS. The spectra of the desialylated oligosaccharide fractions from sample A, EPO-GT-1-A and sample K showed identical masses for complex type oligosaccharides at m/z=1810 Da (diantennary), 2175=triantennary, 2540=tetraantennary, 2906=tetraantennary plus 1 N-acetyllactosamine repeat and 3271=tetraantennary plus 2 N-acetyllactosamine repeats; small signals corresponding to lack of fucose (−146) and galactose (minus 162) were detected which are attributable to the acid hydrolysis conditions applied for sialic acid removal (see MALDI-FIGS. 19, 20 and 21).

Figure 17:
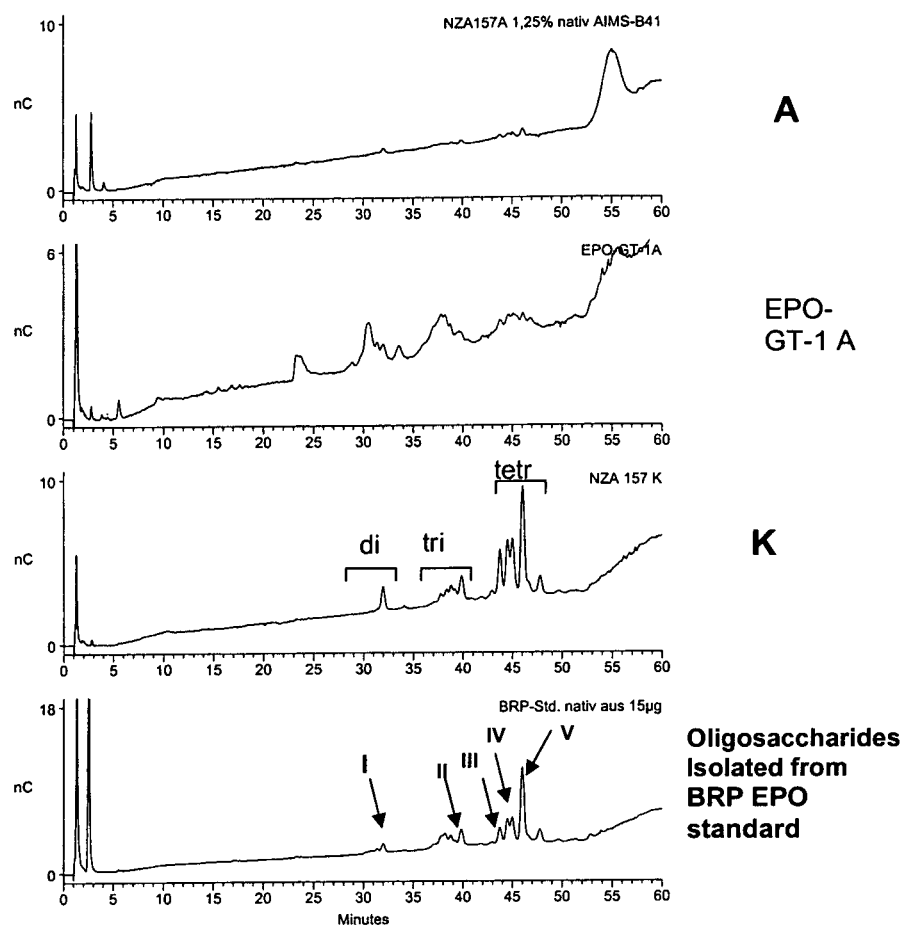
Figure 18:
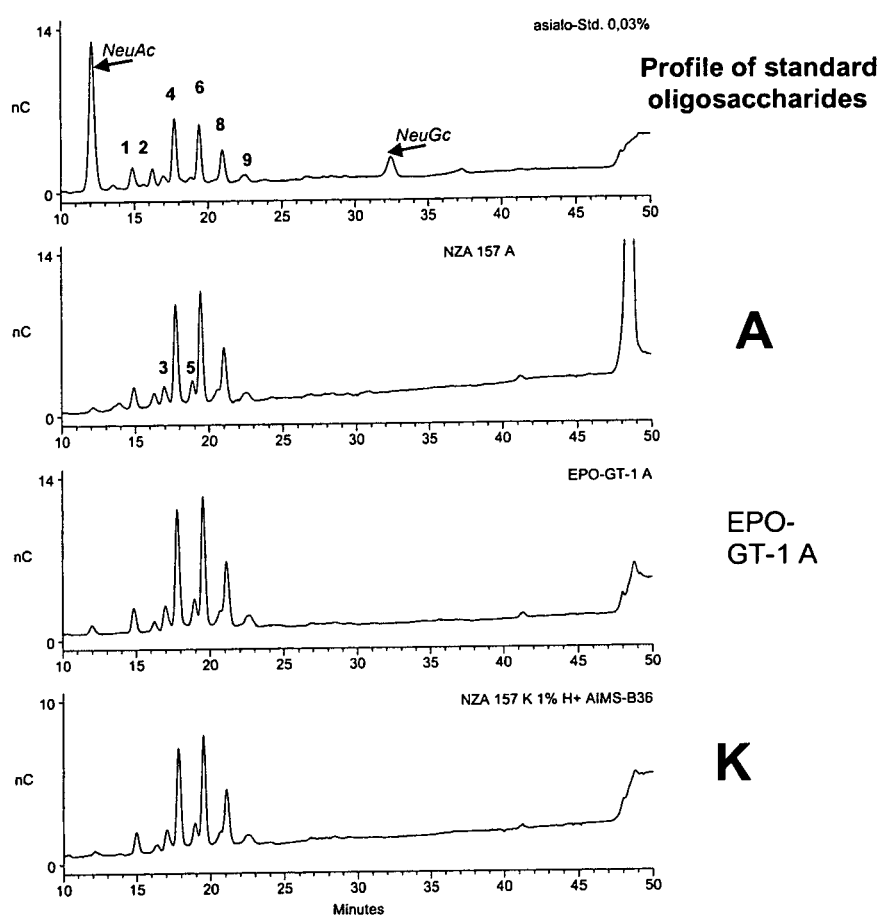
Figure 19:
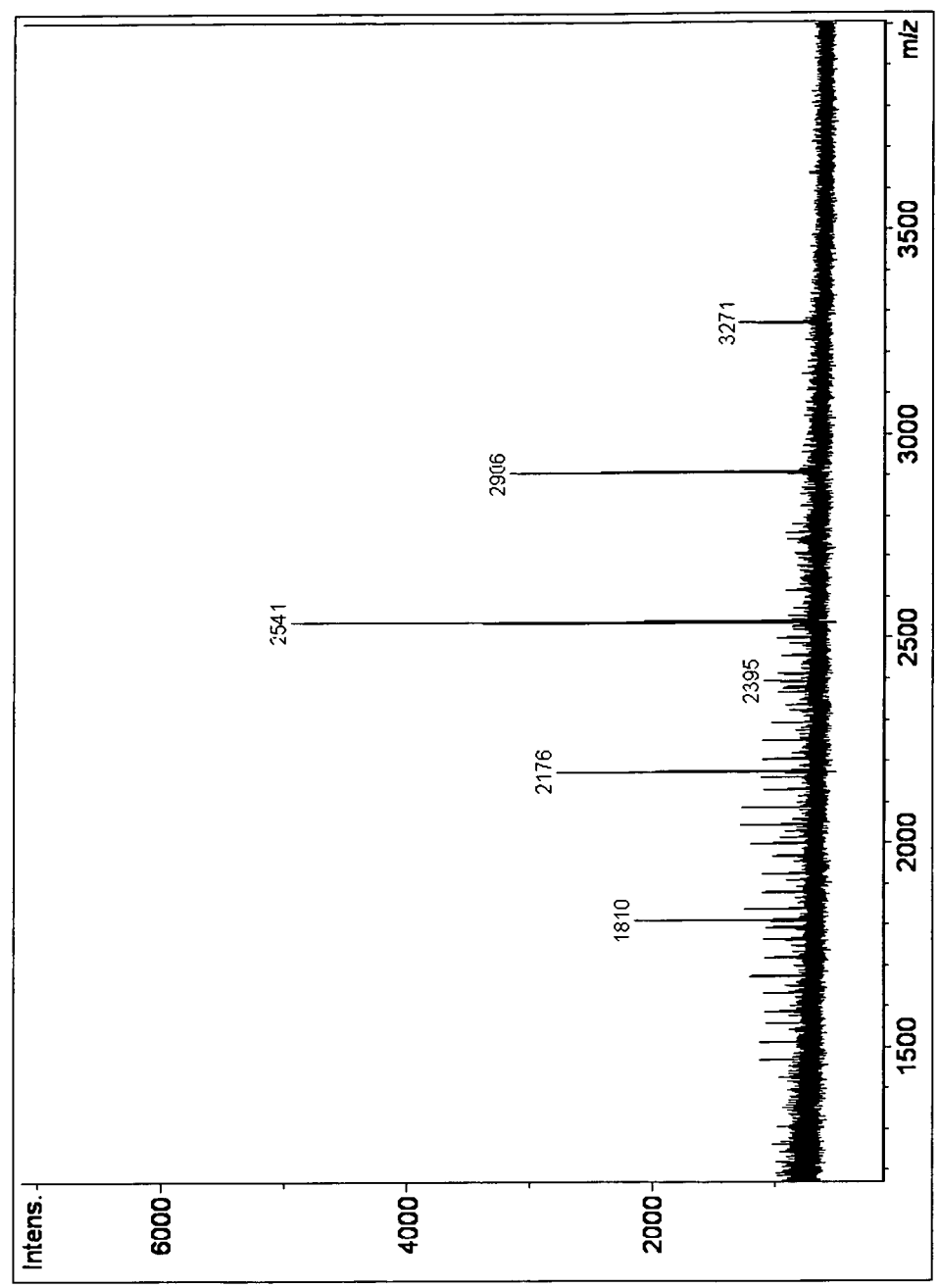
Figure 20:
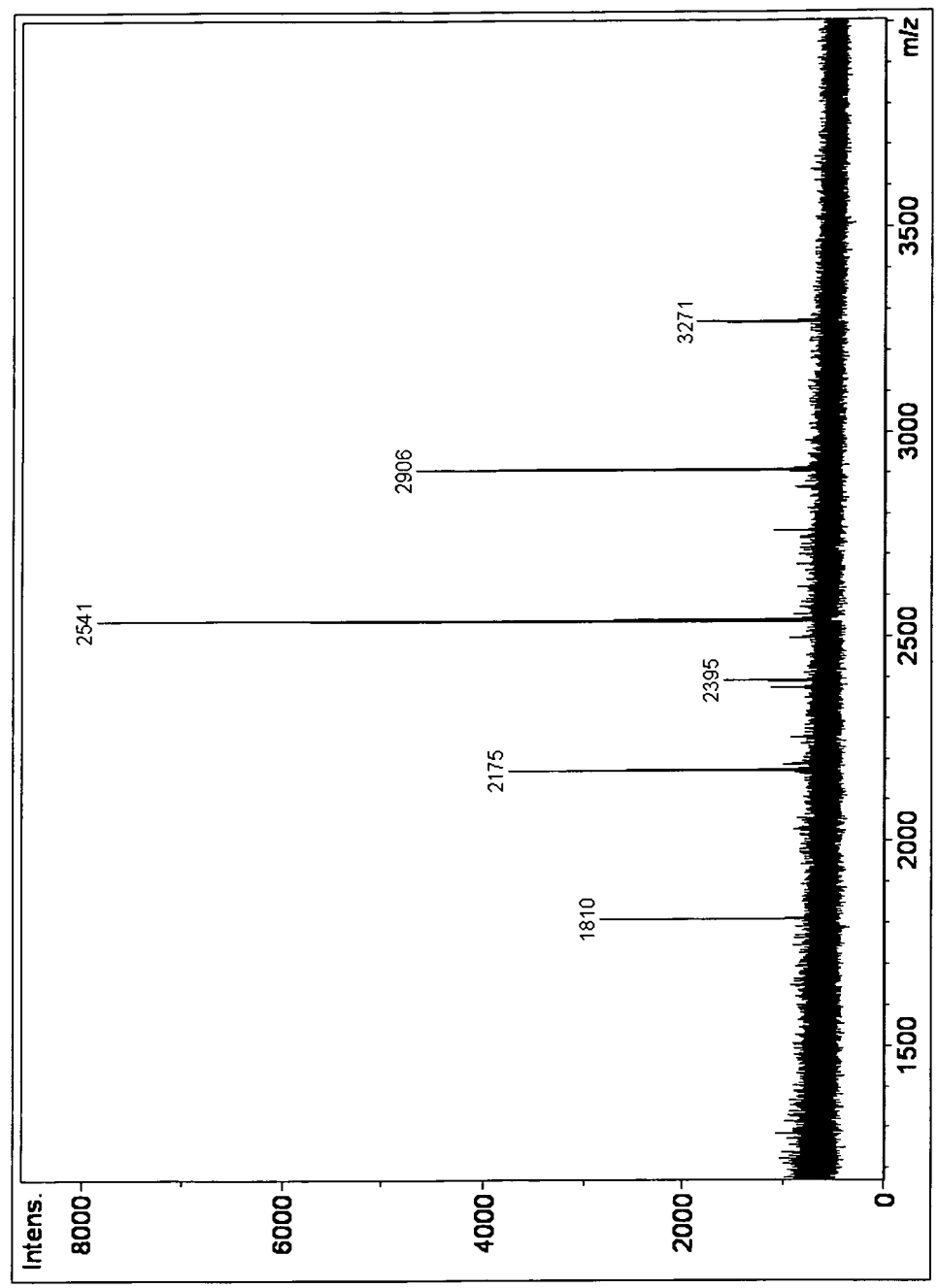
Figure 21:
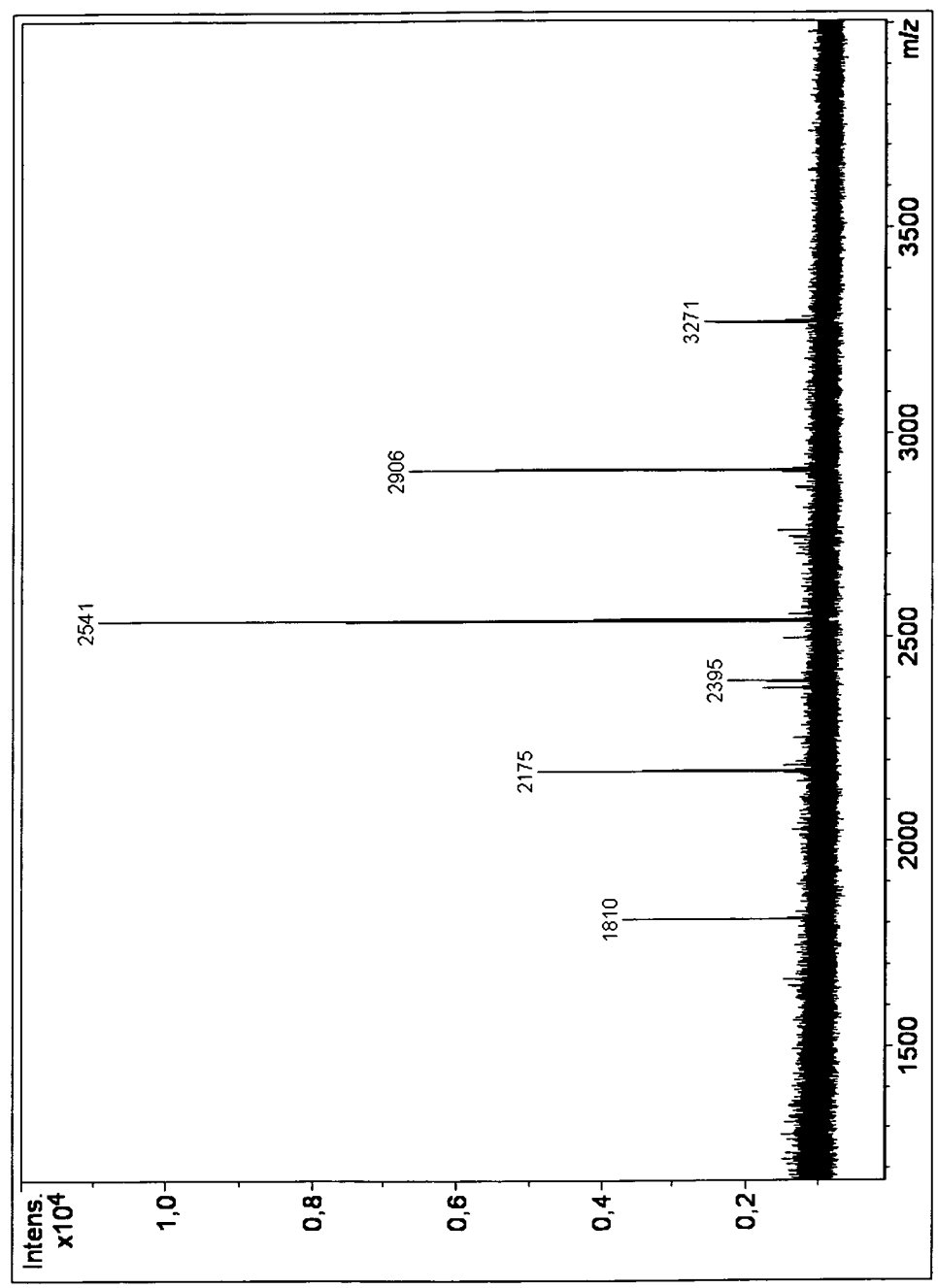
Figure 22:
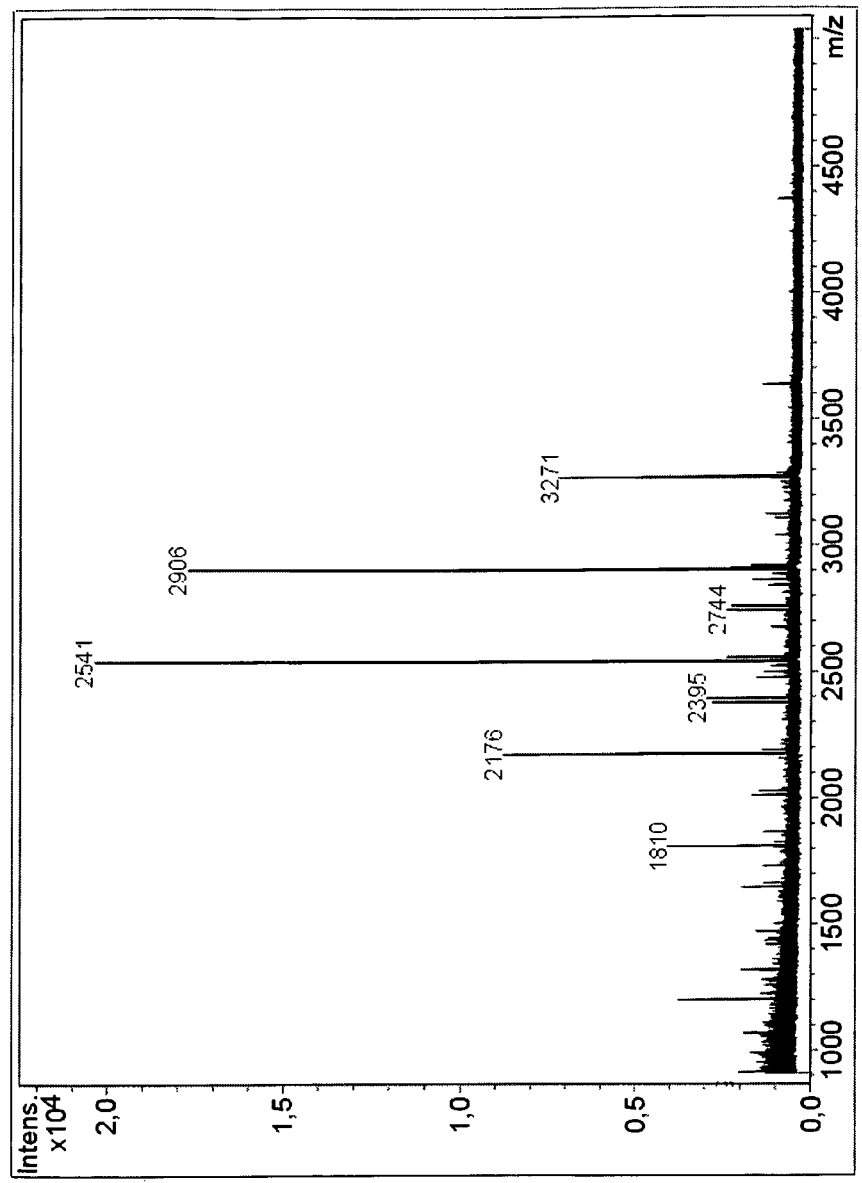
Figure 23:
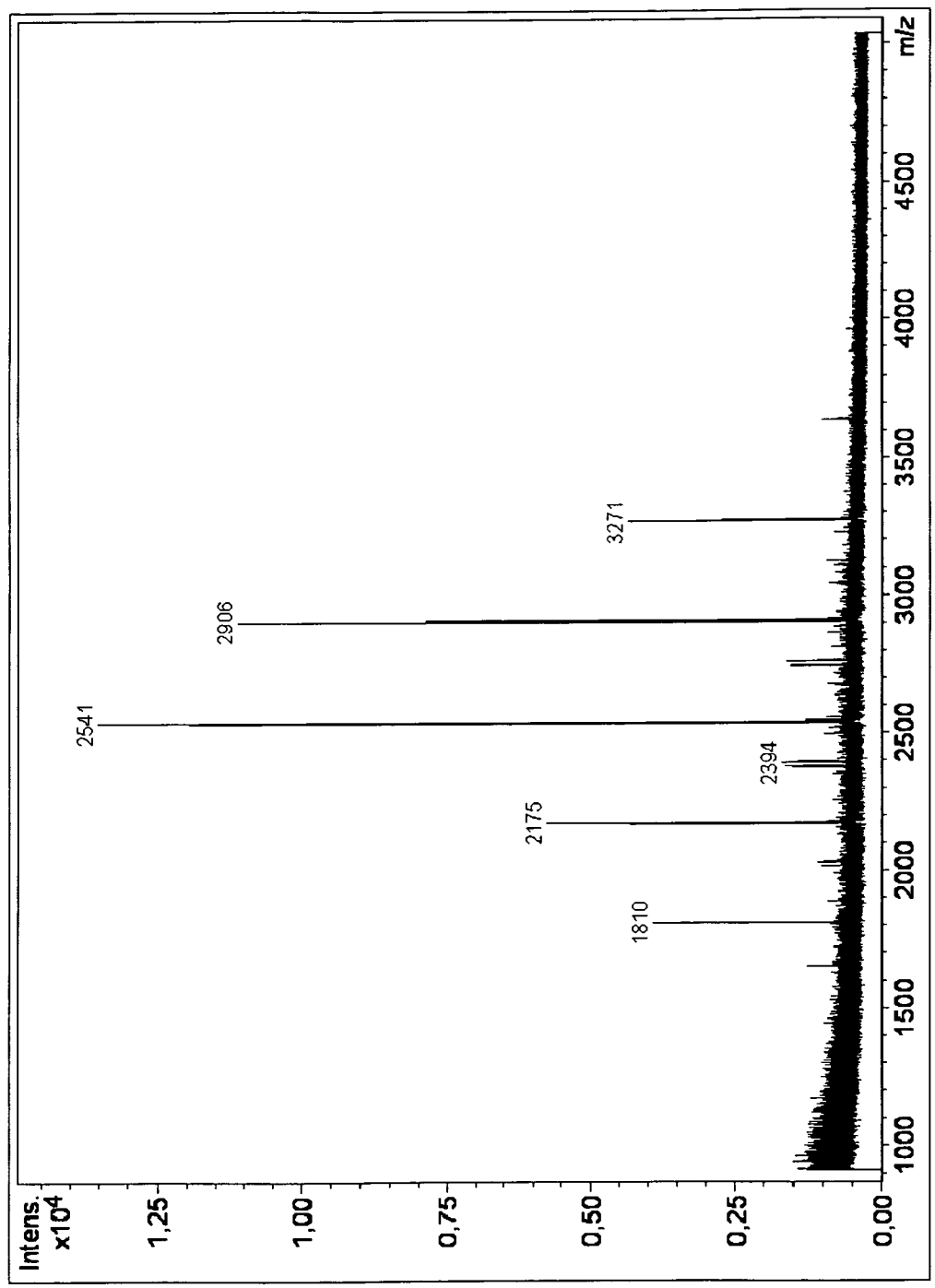
Figure 24:
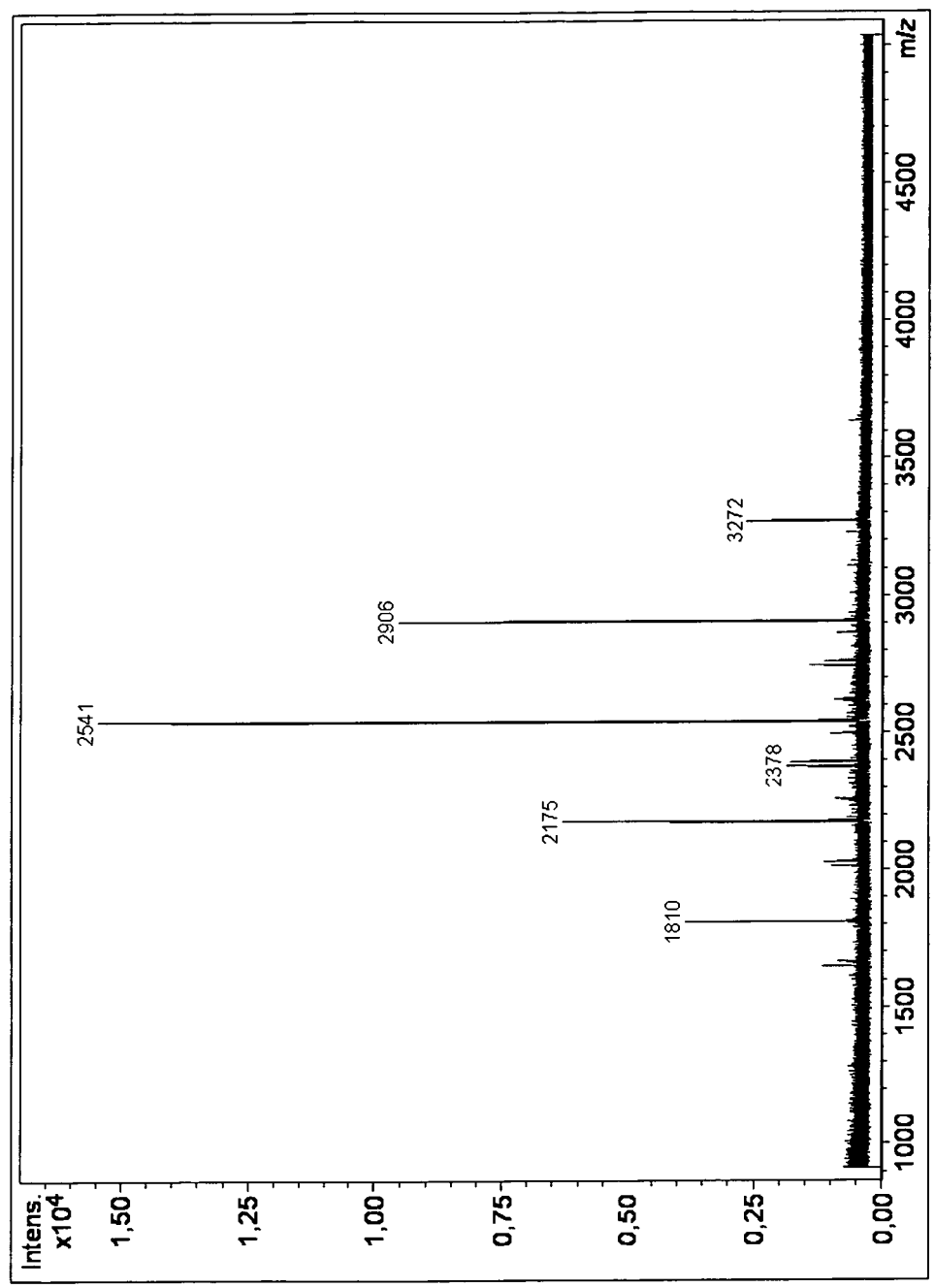
Figure 25:
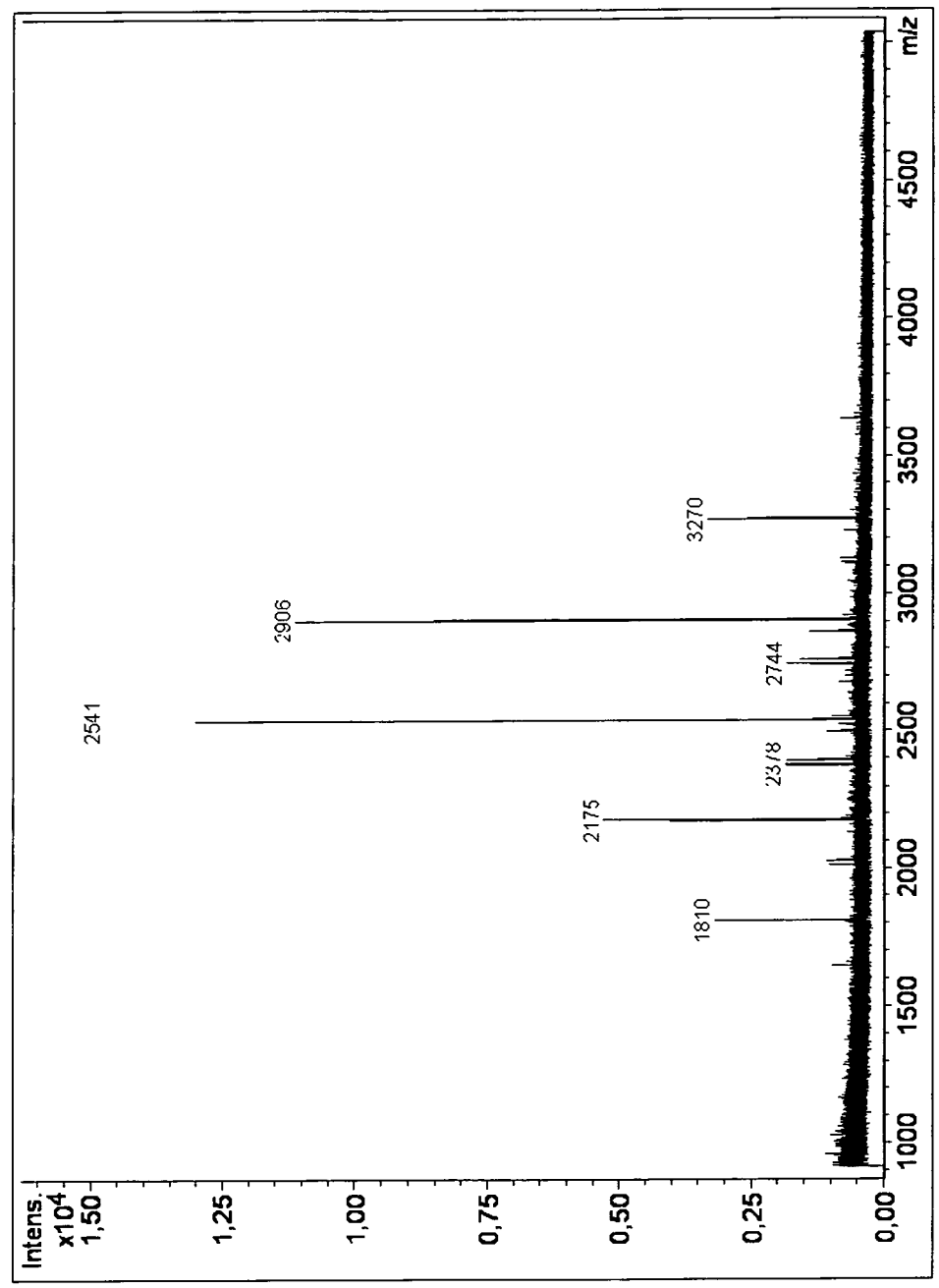

In a parallel experiment the N-glycosidase digestion mixture was absorbed onto 1 ml RP-C18 cartridge (without prior acid hydrolysis of oligosaccharides) and elution was performed with 5% acetonitrile in water containing 0.1% TFA; under these conditions the EPO protein was completely retained onto the RP-material and oligosaccharides were washed off from the column with 5% acetonitrile in $H_2O$ containing 0.1% TFA. The de-N-glycosylated EPO protein was eluted with 70% acetonitrile in $H_2O$ containing 0.1% TFA. The oligosaccharide fractions from the RP-C18 step of N-glycosidase-treated sample A, EPO GT-1-A and sample K were neutralized and subjected to desalting using Hypercarb cartridges as described before. The isolated oligosaccharides were subjected to HPAEC-PAD mapping before (see FIG. 17) and after mild acid treatment under conditions which enabled quantitative removal of sialic acids from glycans (see FIG. 18).

Figure 13:
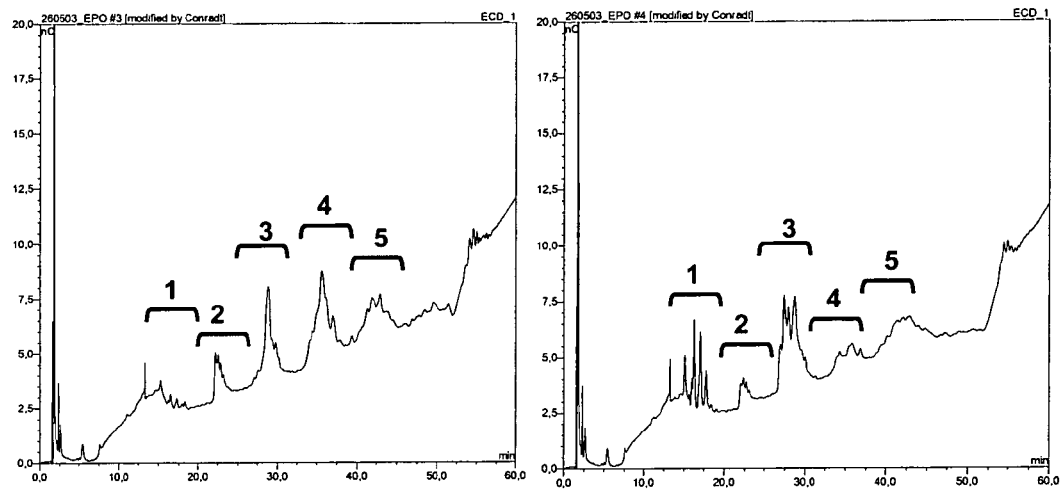
Figure 13:
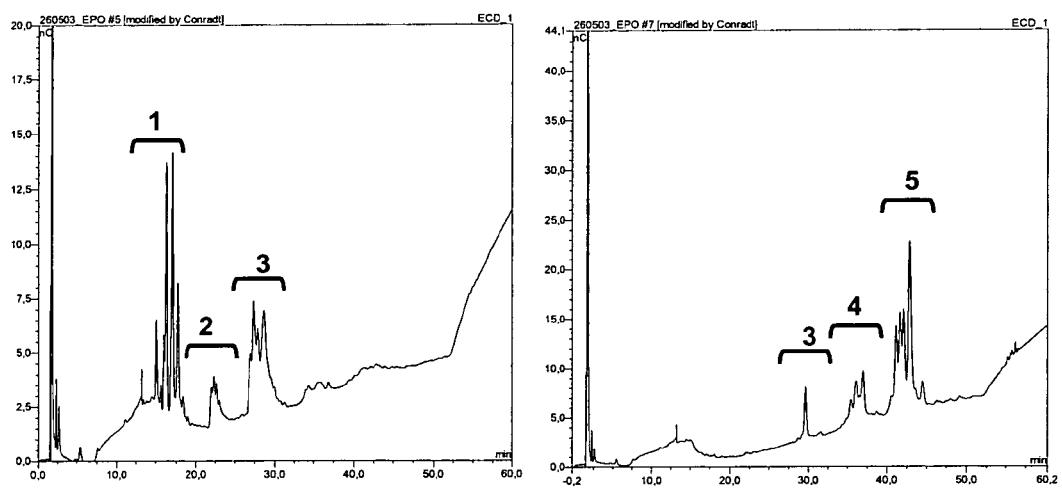

The HPAEC-PAD profile for the native material obtained from the HES-modified sample A showed only neglectable signals for oligosaccharides whereas EPO GT-1-A-derived oligosaccharides exhibited the same glycan profile as the one shown in FIG. 13 (sample named EPO-GT-1 after mild periodate treatment). The elution profile of oligosaccharides obtained from the control EPO sample (K) yielded the expected pattern (compare profile in FIG. 10). For comparison, the native oligosaccharide profile of the international BRP-EPO standard is included for comparison and as reference standard.

After mild acid hydrolysis, all oligosaccharide preparations showed an identical elution profile of neutral oligosaccharide structures (see FIG. 18) with the expected qualitative and quantitative composition of di-, tri- and tetraantennary complex-type carbohydrate chains as described in the methods section for the EPO preparation which was used as a starting material in the present study. This result demonstrates that the HES-modification of the EPO sample results in a covalent linkage of the HES derivative which is detached from the EPO-protein by N-glycosidase and is acid-labile since it is removed from the N-glycans using mild acid treatment conditions known to desialylate carbohydrates (see FIGS. 16a+b).

(cc) Monosaccharide Compositional Analysis of HES-EPO and HES-EPO N-Glycans by GC-MS In order to further confirm HES-modification of EPO at the N-glycans of the molecule, EPO samples were digested with N-glycosidase and the EPO protein was adsorbed onto RP-C18 cartridges whereas oligosaccharide material was washed off as described above. As shown in Table 3, glucose and hydroxyethylated glucose derivatives were detected only in the EPO protein which was subjected to HES-modification at cysteine residues and in oligosaccharide fractions of EPO sample A2.

Example 20.11(d)

In-Vivo Assay of the Biological Activity of HES-Modified EPO

The EPO-bioassay in the normocythaemic mouse system indicates was performed according to the procedures described in the European Pharmacopeia; the laboratory that carried out the EPO assay was using the International BRP EPO reference standard preparation. For the HES-modified EPO A2 preparation a mean value for the specific activity of 294,600 units per mg EPO of protein was determined indicating an approximately 3-fold higher specific activity when compared to the International BRP EPO reference standard preparation that was included in the samples sent for activity assays.

The results of the study are summarized in Table 4.

REFERENCES FOR EXAMPLES 13 TO 20

Nimtz M, Noll G, Paques E P, Conradt H S. Carbohydrate structures of a human tissue plasminogen activator expressed in recombinant Chinese hamster ovary cells. FEBS Lett. 1990 Oct. 1; 271(1-2):14-8

Dorner A J, Wasley L C, Kaufman R J. Increased synthesis of secreted proteins induces expression of glucose-regulated proteins in butyrate-treated Chinese hamster ovary cells. J Biol. Chem. 1989 Dec. 5; 264 (34):20602-7

Mueller P P, Schlenke P, Nimtz M, Conradt H S, Hauser H Recombinant glycoprotein quality in proliferation-controlled BHK-21 cells. Biotechnol Bioeng. 1999 Dec. 5; 65(5):529-36

Nimtz M, Martin W, Wray V, Kloppel K D, Augustin J, Conradt H S. Structures of sialylated oligosaccharides of human erythropoietin expressed in recombinant BHK-21 cells. Eur J. Biochem. 1993 Apr. 1; 213(1):39-56

Hermentin P, Witzel R, Vliegenthart J F, Kanerling J P, Nimtz M, Conradt H S. A strategy for the mapping of N-glycans by high-ph anion-exchange chromatography with pulsed amperometric detection. Anal Biochem. 1992 June; 203 (2):281-9

Schroter S, Derr P, Conradt H S, Nimtz M, Hale G, Kirchhoff C. Male specific modification of human CD52. J Biol. Chem. 1999 Oct. 15; 274(42):29862-73

TABLE 1

| Linker-type | Functional group 1: Reaction with polypeptide, especially EPO | Functional group 2: Reaction with HES |
|---|---|---|
| A | Hydrazide (aldehyde-reactive) | Maleimido (SH-reactive) |
| B | Hydrazide (aldeyde-reactive) | Pydridydithio (SH-reactive) |
| C | Iodoalkyl (SH-reactive) | N-succinimide ester (amine-reactive) |
| D | Bromoalkyl (SH-reactive) | N-succinimide ester (amine-reactive) |
| E | Maleimido (SH-reactive) | N-succinimide ester (amine-reactive) |
| F | Pydridyldithio (SH-reactive) | N-succinimide ester (amine-reactive) |
| G | Vinylsulfone (SH-reactive) | N-succinimide ester (amine-reactive) |

TABLE 2

| Abreviation | Chemical Name | Type | |
|---|---|---|---|
| AMAS | N-(α-Maleimidoacetoxy)succinimide ester | E | 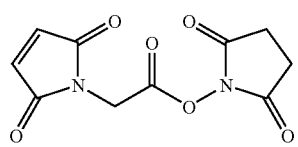 [SMILES: O=C(CN1C(=O)C=CC1=O)ON1C(=O)CCC1=O] |
| BMPH | N-(β-Maleimidopropionic acid)hydrazide TFA | A | 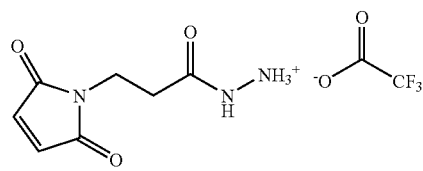 |

TABLE 2-continued

| Abreviation | Chemical Name | Type | |
|---|---|---|---|
| BMPS | N-(β-Maleimidopropyloxy)succinimide ester | E | 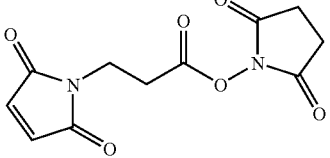 |
| EMCH | N-(ε-Maleimidocaproic acid)hydrazide | A | 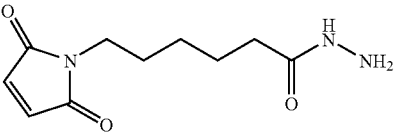 [SMILES: NNC(=O)CCCCCN1C(=O)C=CC1=O] |
| EMCS | N-(ε-Maleimidocaproyloxy)succinimide ester | E | 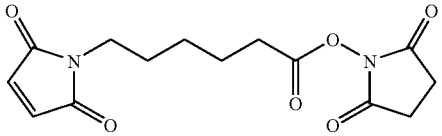 [SMILES: O=C(CCCCCN1C(=O)C=CC1=O)ON1C(=O)CCC1=O] |
| GMBS | N-γ-Maleimidobutyryloxy-succinimide ester | E | 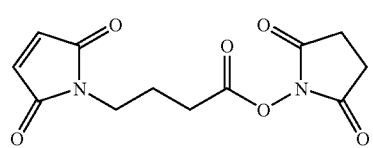 [SMILES: O=C(CCCN1C(=O)C=CC1=O)ON1C(=O)CCC1=O] |
| KMUH | N-(κ-Maleimidoundecanoic acid)hydrazide | A | 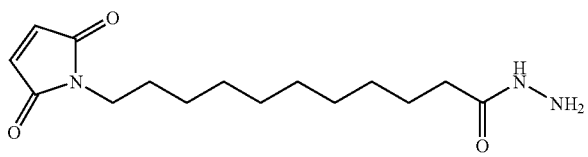 [SMILES: NNC(=O)CCCCCCCCCCN1C(=O)C=CC1=O] |
| LC-SMCC | Succinimidyl 4-(N-maleimidomethyl)cyclohexane-1-carboxy-(6-amido-caproate) | E | 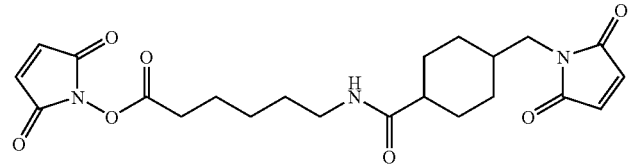 [SMILES: O=C(CCCCCNC(=O)C1CCC(CN2C(=O)C=CC2=O)CC1)ON1C(=O)C=CC1=O] |
| LC-SPDP | Succinimidyl 6-(3'-(2-pyridyl-dithiolpropionamido)hexanoate | F | 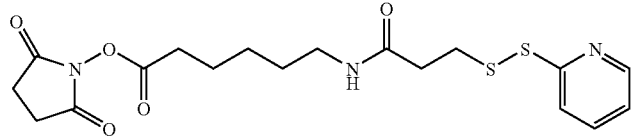 [SMILES: O=C(CCSSc1ccccn1)NCCCCCC(=O)ON1C(=O)CCC1=O] |
| MBS | m-Maleimidobenzoyl-N-hydroxysuccinimide ester | E | 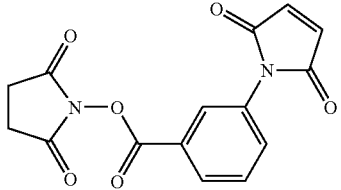 [SMILES: O=C(ON1C(=O)CCC1=O)c1cccc(N2C(=O)C=CC2=O)c1] |
| M₂C₂H | 4-(N-Maleimidomethyl)-cyclohexane-1-carboxyl-hydrazide.HCl.1 2 dioxane | A | 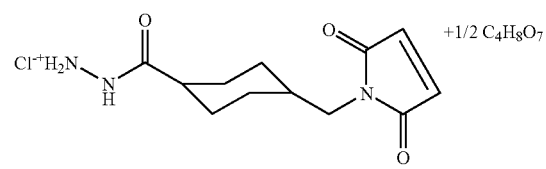 |

TABLE 2-continued

| Abreviation | Chemical Name | Type |
|---|---|---|
| MPBH | 4-(4-N-Maleimidophenyl)-butyric acid hydazide.HCl | A |
| SATA | N-Succinimidyl S-acetylthio-acetate | H |
| SATP | N-Succinimidyl S-acetylthio-propionate | H |
| SBAP | Succinimidyl 3-(bromoacetamido)propionate | D |
| SIA | N-Succinimidyl iodoacetate | C |
| SIAB | N-Succinimidyl(4-iodoacetyl)aminobenzoate | C |
| SMCC | Succinimidyl 4-(N-maleimidomethyl) cyclohexane-1-carboxylate | E |
| SMPB | Succinimidyl 4-(p-maleimidophenyl)butyrate | E |
| SMPH | Succinimidyl-6-(β-maleimidopropionamido) hexanoate | E |

TABLE 2-continued

| Abreviation | Chemical Name | Type |
|---|---|---|
| SMPT | 4-Succinimidyloxy-carbonyl-methyl-α-(2-pyridyldithio)toluene | F |
| SPDP | N-Succinimidyl 3-(2-pyridyldithio)propionate | F |
| Sulfo-EMCS | N-(6-Maleimidocaproyloxy)sulfosuccinimide ester | E |
| Sulfo-GMBS | N-γ-Maleimidobutryloxy-sulfosuccinimide ester | E |
| Sulfo-KMUS | N-(κ-Maleimidoundecanoyloxy)-sulfosuccinimide ester | E |
| Sulfo-LC-SPDP | Sulfosuccinimidyl 6-(3'-[2-pyridyl-dithio]propionamido)hexanoate | F |
| Sulfo-MBS | m-Maleimidobenzoyl-N-hydroxysulfosuccinimide ester | E |
| Sulfo-SIAB | Sulfosuccinimidyl(4-iodoacetyl)aminobenzoate | C |
| Sulfo-SMCC | Sulfosuccinimidyl 4-(N-maleimidomethyl)cyclohexane-1-carboxylate | E |

TABLE 2-continued

| Abreviation | Chemical Name | Type | |
|---|---|---|---|
| Sulfo-SMPB | Sulfosuccinimidyl 4-(p-maleimidophenyl) butyrate | E | 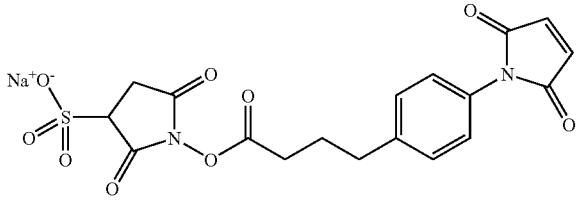 |
| Sulfo-LC-SMPT | Suflosuccinimidyl 6-(α-methyl-α-[2-pyridyldithio]-toluamido)hexanoate | F | 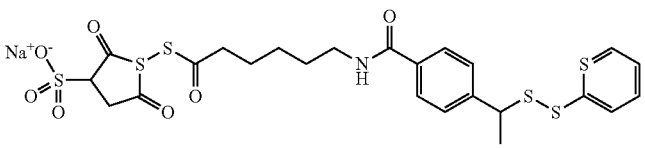 |
| SVSB | N-Succinimidyl-(4-vinylsulfonyl)benzoate | G | 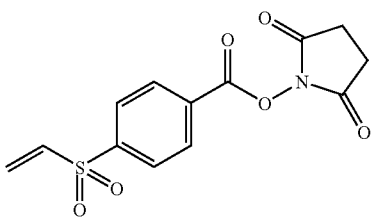 [SMILES: C=CS(=O)(=O)c1ccc(C(=O)ON2C(=O)CCC2=O)cc1] |

TABLE 3

Monosaccharide compositional analysis of glycans from HES-modified EPO and control samples

| **Monosaccharide | I. Glycans from A2 | II. Glycans from EPO-GT-1A | III. Glycans from K2 | III. Glycans from A2 | IV. Glycans from EPO-GT-1A | V. Glycans from K2 | VI. Cystein modified EPO protein* |
|---|---|---|---|---|---|---|---|
| fucose | 1,935 | 3,924 | 2,602 | 2,246 | 4,461 | 2,601 | 2,181 |
| mannose | 6,028 | 11,020 | 9,198 | 6,379 | 11,668 | 6,117 | 6,260 |
| galactose | 8,886 | 19,935 | 14,427 | 10,570 | 16,911 | 11,555 | 10,386 |
| glucose | 17,968 | — | — | 21,193 | trace | trace | 33,021 |
| GlcNAc | 7,839 | 21,310 | 14,440 | 11,360 | 15,953 | 10,503 | 10,498 |
| GlcHe1 | 5,583 | — | — | 5,926 | — | — | 14,857 |
| GlcHe2 | 1,380 | — | — | 1,552 | — | — | 3,775 |
| NeuNAc | 5,461 | 822 | 4,504 | 3,895 | 4,871 | 13,562 | 13,003 |
| inositol | 1,230 | 2,310 | 1,620 | 2,050 | 1,320 | 1,134 | 1,087 |

*the equivalent of Cys-HES-modified EPO protein was subjected to compositional analysis; the EPO protein was isolated from the HES-incubation mixture by chromatography on a Q-Sepharose column as described above and was desalted by centrifugation using a Vivaspin 5 separation device.
**Monosaccharide determinations were performed from single GC runs of the pertrimethylsilylated methylglycosides; the electronical integration values of peaks are given without correction for losses during the derivatisation procedure and recoveries of each compound.

TABLE 4

| Sample No. | Sample description | Calculated specific activity of EPO sample (based on A280 nm and RP-HPLC determination) |
|---|---|---|
| 850247 | 1. HES-modified EPO A2 | 344,000 U/mg |
| 850248 | 2. EPO-GT-1-A | 82,268 U/mg |
| 850249 | 3. Control EPO K2 | 121,410 U/mg |
| 850250 | 4. BRP EPO standard | 86,702 U/mg |
| 850251 | 1. diluted with 4 volume of PBS | 309,129 U/mg |
| 850252 | 2. diluted with 4 volume of PBS | 94,500 U/mg |
| 850253 | 3. diluted with 4 volume of PBS | 114,100 U/mg |
| 850254 | 4. diluted with 4 volume of PBS | 81,200 U/mg |
| 850255 | 1. diluted with 4 volume of PBS | 230,720 U/mg |

What is claimed is:

1. A hydroxyalkylstarch (HAS)-erythropoietin (EPO)-conjugate (HAS-EPO), comprising one or more HAS molecules, wherein the EPO comprises one or more carbohydrate side chains attached to the EPO via N-linked, O-linked, or N-linked and O-linked glycosylation, wherein each HAS is conjugated to the EPO via a carbohydrate moiety that is part of the carbohydrate side chains, wherein the HAS is conjugated to the EPO via O-[2-(2-aminooxy-ethoxy)-ethyl]-hydroxylamine, and wherein the reaction between the HAS and the O-[2-(2-aminooxy-ethoxy)-ethyl]-hydroxylamine takes place at the non-oxidized reducing end of the HAS.

2. The HAS-EPO of claim 1, wherein the EPO has the amino acid sequence of human EPO.

3. The HAS-EPO of claim 1, wherein the carbohydrate side chains have been attached to the EPO during production in mammalian, insect or yeast cells.

4. The HAS-EPO of claim 1, wherein the carbohydrate side chain is oxidized.

5. The HAS-EPO of claim 1, wherein the HAS is conjugated to a galactose or sialic acid residue of the carbohydrate side chains.

6. The HAS-EPO of claim 1, comprising 1-12 HAS molecules per EPO molecule.

7. The HAS-EPO of claim 1, wherein the HAS is selected from the group consisting of hydroxyethylstarch, hydroxypropylstarch and hydroxybutylstarch.

8. The HAS-EPO of claim 7, wherein the HAS is hydroxyethylstarch (HES).

9. The HAS-EPO of claim 8, wherein the HES has a molecular weight of 1 to 300 kDa.

10. The HAS-EPO of claim 8, wherein the HES exhibits a molar degree of substitution of 0.1 to 0.8 and a ratio between C2:C6-substitution in the range of 2-20, with respect to the hydroxyethyl groups.

11. A method for the production of a HAS-EPO, comprising the steps of:
 a) providing EPO being capable of reacting with modified HAS, wherein the EPO comprises one or more carbohydrate side chains attached to the EPO via N-linked, O-linked, or N-linked and O-linked glycosylation,
 b) providing modified HAS being capable of reacting with the EPO of step a), and
 c) reacting the EPO of step a) with the HAS of step b), whereby a HAS-EPO is produced comprising one or more HAS molecules, wherein each HAS is conjugated to the EPO via a carbohydrate moiety that is part of the carbohydrate side chains, wherein the HAS is conjugated to the EPO via O-[2-(2-aminooxy-ethoxy)-ethyl]-hydroxylamine, and wherein the reaction between the HAS and the O-[2-(2-aminooxy-ethoxy)-ethyl]-hydroxylamine takes place at the non-oxidized reducing end of the HAS.

12. The method of claim 11, wherein the EPO has the amino acid sequence of human EPO.

13. The method of claim 11, wherein the EPO is recombinantly produced.

14. The method of claim 11, wherein the carbohydrate side chains have been attached to the EPO during production in mammalian, insect, or yeast cells.

15. The method of claim 11, wherein in step a) the EPO is modified by oxidizing at least one carbohydrate moiety of the one or more carbohydrate side chains of the EPO.

16. The method of claim 15, wherein the terminal saccharide unit is oxidized after partial or complete removal of the terminal sialic acid.

17. The method of claim 16, wherein in step c) the modified HAS is conjugated to the oxidized terminal saccharide unit.

18. The method of claim 11, wherein the HAS is modified such that it comprises a hydroxylamine function.

19. The method of claim 11, wherein step c) is performed in a reaction medium comprising at least 10% per weight $H_2O$.

20. The method of claim 11, wherein the HAS is HES, hydroxypropylstarch or hydroxybutylstarch.

21. The method of claim 20, wherein the HAS is HES, and wherein the HES has a molecular weight of 1 to 300 kDa.

22. A HAS-EPO, obtainable by a method comprising the steps of:
 a) providing EPO being capable of reacting with modified HAS, wherein the EPO comprises one or more carbohydrate side chains attached to the EPO via N-linked, O-linked, or N-linked and O-linked glycosylation,
 b) providing modified HAS being capable of reacting with the EPO of step a), and
 c) reacting the EPO of step a) with the HAS of step b), whereby an HAS-EPO is produced comprising one or more HAS molecules, wherein each HAS is conjugated to the EPO via a carbohydrate moiety that is part of the carbohydrate side chains, wherein the HAS is conjugated to the EPO via O-[2-(2-aminooxy-ethoxy)-ethyl]-hydroxylamine, and wherein the reaction between the HAS and the O-[2-(2-aminooxy-ethoxy)-ethyl]-hydroxylamine takes place at the non-oxidized reducing end of the HAS.

23. A pharmaceutical composition comprising the HAS-EPO according to claim 1 or claim 22.

24. The pharmaceutical composition of claim 23, further comprising at least one pharmaceutically acceptable carrier.

25. A HAS-polypeptide-conjugate (HAS-polypeptide), comprising one or more HAS molecules, wherein the polypeptide comprises one or more carbohydrate side chains attached to the polypeptide via N-linked, O-linked, or N-linked and O-linked glycosylation, wherein each HAS is conjugated to the polypeptide via a carbohydrate moiety that is part of the carbohydrate side chains, wherein the HAS is conjugated to the polypeptide via O-[2-(2-aminooxy-ethoxy)-ethyl]-hydroxylamine, and wherein the reaction between the HAS and the crosslinking compound takes place at the non-oxidized reducing end of the HAS.

26. The HAS-polypeptide of claim 25, wherein the polypeptide is of human origin.

27. The HAS-polypeptide of claim 25, wherein the polypeptide is a cytokine or a therapeutic antibody.

28. The HAS-polypeptide of claim 27, wherein the cytokine is selected from the group consisting of antithrombin III (ATIII), interleukin-2 (IL-2), interleukin-6 (IL-6), interferon-alpha (IFN-α), interferon-beta (IFN-β), colony-stimulating factor (CSF), and granulocyte-colony stimulating factor (G-CSF).

29. The HAS-polypeptide of claim 25, wherein the carbohydrate side chains have been attached to the polypeptide during production in mammalian, insect or yeast cells.

30. The HAS-polypeptide of claim 25, wherein the carbohydrate moiety is oxidized.

31. The HAS-polypeptide of claim 25, wherein the HAS is conjugated to a galactose residue of the carbohydrate side chains.

32. The HAS-polypeptide of claim 25, comprising 1-12 HAS molecules per polypeptide molecule.

33. The HAS-polypeptide of claim 25, wherein the HAS is selected from the group consisting of hydroxyethylstarch (HES), hydroxypropylstarch and hydroxybutylstarch.

34. The HAS-polypeptide of claim 33, wherein the HAS is HES.

35. The HAS-polypeptide of claim 34, wherein the HES has a molecular weight of 1 to 300 kDa.

36. The HAS-polypeptide of claim 34, wherein the HES exhibits a molar degree of substitution of 0.1 to 0.8 and a ratio between C2:C6-substitution in the range of 2-20, with respect to the hydroxyethyl groups.

37. A method for the production of a HAS-polypeptide, comprising the steps of:
 a) providing a polypeptide being capable of reacting with modified HAS, wherein the polypeptide comprises one or more carbohydrate side chains attached to the polypeptide via N-linked, O-linked, or N-linked and O-linked glycosylation,
 b) providing modified HAS being capable of reacting with the polypeptide of step a), and c) reacting the polypeptide of step a) with the HAS of step b), whereby HAS-polypeptide is produced comprising one or more HAS molecules, wherein each HAS is conjugated to the polypeptide via a carbohydrate moiety that is part of the carbohydrate side chains, wherein the HAS is conjugated to the polypeptide via O-[2-(2-aminooxy-ethoxy)-ethyl]-hydroxylamine, and wherein the reaction between the HAS and the O-[2-(2-aminooxy-ethoxy)-ethyl]-hydroxylamine takes place at the non-oxidized reducing end of the HAS.

38. The method of claim 37, wherein the polypeptide is of human origin.

39. The method of claim 37, wherein the polypeptide is selected from the group comprising erythropoietin, interleukins, and therapeutic antibodies.

40. The method of claim 37, wherein the polypeptide is recombinantly produced.

41. The method of claim 37, wherein the carbohydrate side chains have been attached to the polypeptide during production in mammalian, insect or yeast cells.

42. The method of claim 37, wherein in step a) the polypeptide is modified by oxidizing at least one carbohydrate moiety of the one or more carbohydrate side chains of the polypeptide.

43. The method of claim 42, wherein the terminal saccharide unit is oxidized after partial or complete removal of the terminal sialic acid.

44. The method of claim 43, wherein in step c) the modified HAS is conjugated to the oxidized terminal saccharide unit.

45. The method of claim 37, wherein the HAS is modified such that it comprises a hydroxylamine function.

46. The method of claim 37, wherein step c) is performed in a reaction medium comprising at least 10% per weight $H_2O$.

47. The method of claim 37, wherein the HAS is HES, hydroxypropylstarch or hydroxybutylstarch.

48. The method of claim 47, wherein the HAS is HES having a molecular weight of 1 to 300 kDa.

49. A HAS-polypeptide, obtainable by a method comprising the steps of:
   a) providing a polypeptide being capable of reacting with modified HAS, wherein the polypeptide comprises one or more carbohydrate side chains attached to the polypeptide via N-linked, O-linked, or N-linked and O-linked glycosylation,
   b) providing modified HAS being capable of reacting with the polypeptide of step a), and
   c) reacting the polypeptide of step a) with the HAS of step b), whereby HAS-polypeptide is produced comprising one or more HAS molecules, wherein each HAS is conjugated to the polypeptide via a carbohydrate moiety that is part of the carbohydrate side chains, wherein the HAS is conjugated to the polypeptide via O-[2-(2-aminooxy-ethoxy)-ethyl]-hydroxylamine, and wherein the reaction between the HAS and the O-[2-(2-aminooxy-ethoxy)-ethyl]-hydroxylamine takes place at the non-oxidized reducing end of the HAS.

50. A pharmaceutical composition comprising the HAS-polypeptide according to claim 25 or claim 49, wherein the polypeptide is a cytokine or a therapeutic antibody.

51. The pharmaceutical composition of claim 50, further comprising at least one pharmaceutically acceptable carrier.

52. The pharmaceutical composition of claim 50, wherein the cytokine is selected from the group consisting of ATIII, IL-2, IL-6, IFN-α, IFN-β, CSF, and G-CSF.

\* \* \* \* \*